(12) United States Patent
DeLisa et al.

(10) Patent No.: US 8,999,668 B2
(45) Date of Patent: Apr. 7, 2015

(54) GLYCOSYLATED PROTEIN EXPRESSION IN PROKARYOTES

(75) Inventors: Matthew DeLisa, Ithaca, NY (US); Cassandra Guarino, Slaterville Springs, NY (US); Thomas Mansell, Ithaca, NY (US); Adam Fisher, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 12/811,788

(22) PCT Filed: Jan. 5, 2009

(86) PCT No.: PCT/US2009/030110
§ 371 (c)(1),
(2), (4) Date: Oct. 28, 2010

(87) PCT Pub. No.: WO2009/089154
PCT Pub. Date: Jul. 16, 2009

(65) Prior Publication Data
US 2011/0039729 A1   Feb. 17, 2011

Related U.S. Application Data

(60) Provisional application No. 61/018,772, filed on Jan. 3, 2008.

(51) Int. Cl.
| | |
|---|---|
| C40B 30/06 | (2006.01) |
| C12N 1/00 | (2006.01) |
| C12N 9/14 | (2006.01) |
| C07K 16/12 | (2006.01) |
| C12N 9/10 | (2006.01) |
| C12P 21/00 | (2006.01) |

(52) U.S. Cl.
CPC .............. *C12N 9/14* (2013.01); *C07K 16/1278* (2013.01); *C07K 2317/21* (2013.01); *C07K 2317/41* (2013.01); *C12N 9/1051* (2013.01); *C12P 21/005* (2013.01)

(58) Field of Classification Search
CPC .. C12N 9/14; C12N 14/1051; C07K 16/1278; C12P 21/005
USPC .................................. 435/69.1, 71.2, 85, 97
See application file for complete search history.

(56) References Cited

U.S. PATENT DOCUMENTS

| | | |
|---|---|---|
| 2005/0170452 A1 | 8/2005 | Wildt et al. |
| 2006/0211085 A1 | 9/2006 | Bobrowicz |
| 2006/0234345 A1 | 10/2006 | Schwartz et al. |
| 2006/0252672 A1 | 11/2006 | Betenbaugh et al. |
| 2006/0257399 A1 | 11/2006 | Gerngross et al. |
| 2006/0286637 A1 | 12/2006 | Hamilton |
| 2007/0026485 A1 | 2/2007 | DeFrees et al. |
| 2007/0178551 A1 | 8/2007 | Gerngross |

FOREIGN PATENT DOCUMENTS

| | | |
|---|---|---|
| JP | 2005-514021 A | 5/2005 |
| JP | 2005-518806 A | 6/2005 |
| WO | 03/056914 A1 | 7/2003 |
| WO | 03/074687 A1 | 9/2003 |
| WO | 2004/013151 A2 | 2/2004 |
| WO | 2004/035605 A2 | 4/2004 |
| WO | 2006/102652 A2 | 9/2006 |
| WO | 2006/119987 A2 | 11/2006 |
| WO | 2007/120932 A2 | 10/2007 |

OTHER PUBLICATIONS

Alaimo et al.; Two distinct but interchangeable mechanisms for flipping of lipid-linked oligosaccharides; The EMBO Journal (2006) 25, 967-976).*
International Preliminary Report on Patentability dated Oct. 30, 2009.
Supplementary European Search Report for European Application No. 09701421 dated Jun. 17, 2011.
European Search Opinion for European Patent Application No. 09701421 dated Jun. 17, 2011.
Weerapana et al., "Asparagine-Linked Protein Glycosylation: From Eukaryotic to Prokaryotic Systems," Glycobiol. 16 (6):91R-101R (2006).
Kowarik et al., "Definition of the Bacterial N-Glycosylation Site Consensus Sequence," Embo J. 25(9):1957-1966 (2006).
Wright et al., "Effect of Glycosylation on Antibody Function: Implications for Genetic Engineering," Trends Biotechnol. 15(1):26-32 (1997).
Wacker et al., "N-Linked Glycosylation in Campylobacter Jejuni and its Functional Transfer into *E. Coli*," Science 298:1790-1793 (2002).
O'Reilly et al., "In vitro Evidence for the Dual Function of Alg2 and Alg11: Essential Mannosyltransferases in N-linked Glycoprotein Biosynthesis," Biochem. 45(31):9593-9603 (2006).

(Continued)

*Primary Examiner* — Jim Ketter
*Assistant Examiner* — Antonio Galisteo Gonzalez
(74) *Attorney, Agent, or Firm* — LeClairRyan, a Professional Corporation

(57) ABSTRACT

The present invention relates to a prokaryotic host cell comprising eukaryotic glycosyltransferase activity, where the eukaryotic glycosyltransferase activity is eukaryotic dolichyl-linked UDP-GlcNAc transferase activity and eukaryotic mannosyl-transferase activity. Also disclosed is a method of producing a glycosylated protein by providing a prokaryotic host cell comprising the eukaryotic glycosyltransferase activity and culturing the prokaryotic host cell under conditions effective to produce a glycosylated protein. Another aspect of the present invention pertains to a method for screening bacteria or bacteriophages by expressing one or more glycans on the surface of a bacteria, attaching a label on the one or more glycans on the surface of the bacteria or on the surface of a bacteriophage derived from the bacteria, and analyzing the label in a high-throughput format. A glycosylated antibody comprising an Fv portion which recognizes and binds to a native antigen and an Fc portion which is glycosylated at a conserved asparagine residue is also disclosed.

11 Claims, 36 Drawing Sheets

(56) References Cited

OTHER PUBLICATIONS

Bickel et al., "Biosynthesis of Lipid-Linked Oligosaccharides in *Saccharomyces cerevisiae:* Alg13p and Alg14p form a Complex Required for the Formation of GlcNac 2-PP-dolichol," J. Biol. Chem. 280(41):34500-34506 (2005).

Couto et al., "Cloning and Expression in *Escherichia-coli* of a Yeast Mannosyltransferase from the Asparagine Linked Glycosylation Pathway," J. Biol. Chem. 259(1):378-382 (1984).

Averbeck et al., "Membrane Topology of the Alg14 Endoplasmic Reticulum UDP-GlcNAc Trnasferase Subunit," J Biol. Chem. 282(40):29081-8 (2007).

Burda et al., "The Dolichol Pathway of N-linked Glycosylation," Biochim. Biophys. Acta. 1426(2):239-57 (1999) (Abstract).

Gao et al., "Physical Interactions Between the Alg1, Alg2, and Alg11 Mannosyltransferases of the Endoplasmic Reticulum," Glycobiology 14(6):559-70 (2004).

Genbank Accession No. EF058387, Synthetic Construct *Saccharomyces cerevisiae* Clone FLH201719.01X Alg13, Complete Sequence, NCBI GenBank (online) http://www.ncbi.ntm.nih.gov/nuccore/116615602 (Oct. 13, 2009).

Helenius et al., "Transmembrane Movement of Dolichol Linked Carbohydrates During N-glycoprotein Biosynthesis in the Endoplasmic Reticulum," Semin. Cell Dev. Biol. 13(3):171-8 (2002) (Abstract).

Hu et al., "Approaching a Complete Repository of Sequence-Verified Protein-Encoding Clones for *Saccharomyces cerevisiae*," Genome Res. 17(4):536-43 (2007).

International Search Report for International Patent Application No. PCT/US2009/030110 (Oct. 30, 2009).

Kim et al., "Membrane Topology of the SST3 Subunit of the Oligosaccharyl Transferase Complex," J. Biol. Chem. 280 (21):20261-7 (2005).

Tannert et al., "Protein-mediated Transbilayers Movement of Lipids in Eukaryotes and Prokaryotes; The Relevance of ABC Transporters," Int. J. Antimicrob. Agents 22(3):177-87 (2003) (Abstract).

Helenius et al., "Translocation of Lipid-Linked Oligosaccharides Across the ER Membrane Requires Rft1 Protein," Nature 415(6870):447-450 (2002) (asbtract only).

Karamyshev et al., "Mapping the Interaction of the STT3 Subunit of the Oligosaccharyl Transferase Complex with Nascent Polypeptide Chains," J. Biol. Chem. 280(49):40489-40493 (2005).

Wilson et al., "Dolichol is Not a Necessary Moiety for Lipid-Linked Oligosaccharide Substrates of the Mannosyltransferases Involved in In Vitro N-Linked-Oligosaccharide Assembly," Biochem. J. 310:909-916 (1995).

Written Opinion and Search Report for corresponding Singapore Application No. 201004761-1 (Nov. 23, 2011).

Chen et al., "From Peptide to Protein: Comparative Analysis of the Substrate Specificity of N-Linked Glycosylation in *C. jejuni*," Biochemistry 46:5579-5585 (2007).

Rosenwald and Krag, "Lec9 CHO Glycosylation Mutants are Defective in the Synthesis of Dolichol," J. Lipid Res. 31:523-533 (1990).

Office Action for corresponding EP Application No. 09 701 421.1 (Feb. 18, 2013).

Notice of Reasons for Rejection for corresponding Japanese Patent Application No. 2010-541578 (Aug. 1, 2013).

Halenius & Aebi, "Transmembrane Movement of Dolichol Linked Carbohydrates During N-glycoprotein Biosynthesis in the Endoplasmic Reticulum," Cell Dev. Biol. 13:171-178 (2002).

Averbeck et al., "Membrane Topology of the Alg14 Endoplasmic Reticulum UDPGlcNAc Transferase Subunit," J. Biol. Chem. 282(40):29081-29088 (2007).

First Examination Report for corresponding Indian Application No. 4167/CHENP/2010 (Jun. 24, 2014).

Decision of Rejection and English Translation for corresponding Japanese Patent Application No. 2010-541578 (Apr. 2, 2014).

\* cited by examiner

ALIGNMENT

```
              10         20         30         40         50         60
          ....|....|....|....|....|....|....|....|....|....|....|....|
alg1      atgtttttggaaattcctcggtggttacttgccttaataatattataccttttccataccg
           M  F  L  E  I  P  R  W  L  L  A  L  I  I  L  Y  L  S  I  P
alg1 cOpt ATGTTCCTGGAAATCCCGCGTTGGCTGCTGGCTCTGATCATCCTGTACCTGTCTATCCCG
           M  F  L  E  I  P  R  W  L  L  A  L  I  I  L  Y  L  S  I  P 70         80         90        100        110        120
          ....|....|....|....|....|....|....|....|....|....|....|....|
alg1      ttagtggtttattatgttataccctactgttttatggcaacaagtcgaccaaaaaaagg
           L  V  V  Y  Y  V  I  P  Y  L  F  Y  G  N  K  S  T  K  K  R
alg1 cOpt CTGGTTGTTTACTACGTTATCCCGTACCTGTTCTACGGTAACAAATCTACCAAAAAACGT
           L  V  V  Y  Y  V  I  P  Y  L  F  Y  G  N  K  S  T  K  K  R 130        140        150        160        170        180
          ....|....|....|....|....|....|....|....|....|....|....|....|
alg1      atcatcatatttgtgctgggtgatgtaggacactctccaaggatatgctatcacgctata
           I  I  I  F  V  L  G  D  V  G  H  S  P  R  I  C  Y  H  A  I
alg1 cOpt ATCATCATCTTCGTTCTGGGTGACGTTGGTCACTCTCCGCGTATCTGCTACCACGCTATC
           I  I  I  F  V  L  G  D  V  G  H  S  P  R  I  C  Y  H  A  I 190        200        210        220        230        240
          ....|....|....|....|....|....|....|....|....|....|....|....|
alg1      agtttcagtaagttaggttggcaagtcgagctatgcggttatgtggaggacactctaccc
           S  F  S  K  L  G  W  Q  V  E  L  C  G  Y  V  E  D  T  L  P
alg1 cOpt TCTTTCTCTAAACTGGGTTGGCAGGTTGAACTGTGCGGTTACGTTGAAGACACCCTGCCG
           S  F  S  K  L  G  W  Q  V  E  L  C  G  Y  V  E  D  T  L  P 250        260        270        280        290        300
          ....|....|....|....|....|....|....|....|....|....|....|....|
alg1      aaaatatttccagtgatccaaatatcaccgtccatcatatgtcaaacttgaaaagaaag
           K  I  I  S  D  P  N  I  T  V  H  H  M  S  N  L  K  R  K
alg1 cOpt AAAATCATCTCTTCTGACCCGAACATCACCGTTCACCACATGTCTAACCTGAAACGTAAA
           K  I  I  S  D  P  N  I  T  V  H  H  M  S  N  L  K  R  K 310        320        330        340        350        360
          ....|....|....|....|....|....|....|....|....|....|....|....|
alg1      ggaggcggaacatcagttatatttatggtaaagaaggtgcttttcaagtttttaagtatt
           G  G  G  T  S  V  I  F  M  V  K  K  V  L  F  Q  V  L  S  I
alg1 cOpt GGTGGTGGTACCTCTGTTATCTTCATGGTAAAAAAAGTTCTGTTCCAGGTTCTGTCTATC
           G  G  G  T  S  V  I  F  M  V  K  K  V  L  F  Q  V  L  S  I 370        380        390        400        410        420
          ....|....|....|....|....|....|....|....|....|....|....|....|
alg1      ttcaaattactttgggaattgagaggaagcgattacatactagttcaaaatccaccgagc
           F  K  L  L  W  E  L  R  G  S  D  Y  I  L  V  Q  N  P  P  S
alg1 cOpt TTCAAACTGCTGTGGGAACTGCGTGGTTCTGACTACATCCTGGTTCAGAACCCGCCGTCT
           F  K  L  L  W  E  L  R  G  S  D  Y  I  L  V  Q  N  P  P  S
```

```
                  910       920       930       940       950       960
             ....|....|....|....|....|....|....|....|....|....|....|....|
alg1         ttgcctaagatcttgtgttttataacgggtaaaggaccactaaggagaaatatatgaag
              L  P  K  I  L  C  F  I  T  G  K  G  P  L  K  E  K  Y  M  K
alg1 COpt    CTGCCGAAAATCCTGTGCTTCATCACCGGTAAAGGTCCGCTGAAAGAAAAATACATGAAA
              L  P  K  I  L  C  F  I  T  G  K  G  P  L  K  E  K  Y  M  K 970       980       990      1000      1010      1020
             ....|....|....|....|....|....|....|....|....|....|....|....|
alg1         caaggagaagaatatgactggaagcgctgtcaaatcgaattgtgtggttgtcagcagag
              Q  V  E  E  Y  D  W  K  R  C  Q  I  E  F  V  W  L  S  A  E
alg1 COpt    CAGGTTGAAGAATACGACTGGAAACGTTGCCAGATCGAATTCGTTTGGCTGTCTGCTGAA
              Q  V  E  E  Y  D  W  K  R  C  Q  I  E  F  V  W  L  S  A  E 1030      1040      1050      1060      1070      1080
             ....|....|....|....|....|....|....|....|....|....|....|....|
alg1         gattacccaaagttattacaattatgcgattacggagtttccctgcatacttcaagttca
              D  Y  P  K  L  L  Q  L  C  D  Y  G  V  S  L  H  T  S  S  S
alg1 COpt    GACTACCCGAAACTGCTGCAGCTGTGCGACTACGGTGTTTCTCTGCACACCTCTTCTTCT
              D  Y  P  K  L  L  Q  L  C  D  Y  G  V  S  L  H  T  S  S  S 1090      1100      1110      1120      1130      1140
             ....|....|....|....|....|....|....|....|....|....|....|....|
alg1         gggttggacctgccaatgaaaattttagatatgtttggctcaggtcttcctgttattgca
              G  L  D  L  P  M  K  I  L  D  M  F  G  S  G  L  P  V  I  A
alg1 COpt    GGTCTGGACCTGCCGATGAAAATCCTGGACATGTTCGGTTCTGGTCTGCCGGTTATCGCT
              G  L  D  L  P  M  K  I  L  D  M  F  G  S  G  L  P  V  I  A 1150      1160      1170      1180      1190      1200
             ....|....|....|....|....|....|....|....|....|....|....|....|
alg1         atgaactatccagtgcttgacgaattagtacaacacaatgtaaatgggttaaaatttgtt
              M  N  Y  P  V  L  D  E  L  V  Q  H  N  V  N  G  L  K  F  V
alg1 COpt    ATGAACTACCCGGTTCTGGACGAACTGGTTCAGCACAACGTTAACGGTCTGAAATTCGTT
              M  N  Y  P  V  L  D  E  L  V  Q  H  N  V  N  G  L  K  F  V 1210      1220      1230      1240      1250      1260
             ....|....|....|....|....|....|....|....|....|....|....|....|
alg1         gatagaagggagcttcatgaatctctgattttttgctatgaaagatgctgatttataccaa
              D  R  R  E  L  H  E  S  L  I  F  A  M  K  D  A  D  L  Y  Q
alg1 COpt    GACCGTCGTGAACTGCACGAATCTCTGATCTTCGCTATGAAAGACGCTGACCTGTACCAG
              D  R  R  E  L  H  E  S  L  I  F  A  M  K  D  A  D  L  Y  Q 1270      1280      1290      1300      1310      1320
             ....|....|....|....|....|....|....|....|....|....|....|....|
alg1         aaattgaagaaaaatgtaacgcaggaagctgagaacagatggcaatcaaattgggaacga
              K  L  K  K  N  V  T  Q  E  A  E  N  R  W  Q  S  N  W  E  R
alg1 COpt    AAACTGAAAAAAAACGTTACCCAGGAAGCTGAAAACCGTTGGCAGTCTAACTGGGAACGT
              K  L  K  K  N  V  T  Q  E  A  E  N  R  W  Q  S  N  W  E  R 1330      1340      1350
             ....|....|....|....|....|....|
alg1         acaatgagagatttgaagctaattcattga
              T  M  R  D  L  K  L  I  H  *
alg1 COpt    ACCATGCGTGACCTGAAACTGATCCACTAA
              T  M  R  D  L  K  L  I  H  *
```

Figure 13 (continued)

ALIGNMENT

```
                   10         20         30         40         50         60
            ....|....|....|....|....|....|....|....|....|....|....|....|
alg2        atgattgaaaaggataaaagaacgattgcttttattcatccagacctaggtattgggggc
             M  I  E  K  D  K  R  T  I  A  F  I  H  P  D  L  G  I  G  G
alg2 copt   ATGATCGAAAAAGACAAACGTACCATCGCTTTCATCCACCGGACCTGGGTATCGGTGGT
             M  I  E  K  D  K  R  T  I  A  F  I  H  P  D  L  G  I  G  G 70         80         90        100        110        120
            ....|....|....|....|....|....|....|....|....|....|....|....|
alg2        gctgaaaggttagtcgtcgatgcagcattaggtctacaacaacaaggacatagtgtaatc
             A  E  R  L  V  V  D  A  A  L  G  L  Q  Q  Q  G  H  S  V  I
alg2 copt   GCTGAACGTCTGGTTGTTGACGCTGCTCTGGGTCTGCAGCAGCAGGGTCACTCTGTTATC
             A  E  R  L  V  V  D  A  A  L  G  L  Q  Q  Q  G  H  S  V  I 130        140        150        160        170        180
            ....|....|....|....|....|....|....|....|....|....|....|....|
alg2        atctatactagtcactgtgataaatcacattgtttcgaagaagttaaaaacggccaatta
             I  Y  T  S  H  C  D  K  S  H  C  F  E  E  V  K  N  G  Q  L
alg2 copt   ATCTACACCTCTCACTGCGACAAATCTCACTGCTTCGAAGAAGTTAAAAACGGTCAGCTG
             I  Y  T  S  H  C  D  K  S  H  C  F  E  E  V  K  N  G  Q  L 190        200        210        220        230        240
            ....|....|....|....|....|....|....|....|....|....|....|....|
alg2        aaagtcgaagtttatggtgatttcttaccgacaaacttttgggtcgttttttttattgtt
             K  V  E  V  Y  G  D  F  L  P  T  N  F  L  G  R  F  F  I  V
alg2 copt   AAAGTTGAAGTTTACGGTGACTTCCTGCCGACCAACTTCCTGGGTCGTTTCTTCATCGTT
             K  V  E  V  Y  G  D  F  L  P  T  N  F  L  G  R  F  F  I  V 250        260        270        280        290        300
            ....|....|....|....|....|....|....|....|....|....|....|....|
alg2        ttcgcaacaattagacagctttatttagttattcaattgatcctacagaaaaaagtgaat
             F  A  T  I  R  Q  L  Y  L  V  I  Q  L  I  L  Q  K  K  V  N
alg2 copt   TTCGCTACCATCCGTCAGCTGTACCTGGTTATCCAGCTGATCCTGCAGAAAAAAGTTAAC
             F  A  T  I  R  Q  L  Y  L  V  I  Q  L  I  L  Q  K  K  V  N 310        320        330        340        350        360
            ....|....|....|....|....|....|....|....|....|....|....|....|
alg2        gcgtaccaattaattatcattgatcaactgtctacatgtattccgcttctgcatatcttt
             A  Y  Q  L  I  I  I  D  Q  L  S  T  C  I  P  L  L  H  I  F
alg2 copt   GCTTACCAGCTGATCATCATCGACCAGCTGTCTACCTGCATCCCGCTGCTGCACATCTTC
             A  Y  Q  L  I  I  I  D  Q  L  S  T  C  I  P  L  L  H  I  F 370        380        390        400        410        420
            ....|....|....|....|....|....|....|....|....|....|....|....|
alg2        agttctgccactttgatgttttattgtcatttccccgaccaattattggctcaaagagct
             S  S  A  T  L  M  F  Y  C  H  F  P  D  Q  L  L  A  Q  R  A
alg2 copt   TCTTCTGCTACCCTGATGTTCTACTGCCACTTCCCGGACCAGCTGCTGGCTCAGCGTGCT
             S  S  A  T  L  M  F  Y  C  H  F  P  D  Q  L  L  A  Q  R  A
```

Figure 14

```
            430        440        450        460        470        480
         ....|....|....|....|....|....|....|....|....|....|....|....|
alg2     gggctattgaagaaaatatacagactaccattgacttaatagaacgttttccgtgagt
          G  L  L  K  K  I  Y  R  L  P  F  D  L  I  E  Q  F  S  V  S
alg2 copt GGTCTGCTGAAAAAATCTACCGTCTGCCGTTCGACCTGATCGAACAGTTCTCTGTTTCT
          G  L  L  K  K  I  Y  R  L  P  F  D  L  I  E  Q  F  S  V  S 490        500        510        520        530        540
         ....|....|....|....|....|....|....|....|....|....|....|....|
alg2     gctgccgatactgttgtggtaaattcaaatttcactaagaatacgttccaccaaacgttc
          A  A  D  T  V  V  V  N  S  N  F  T  K  N  T  F  H  Q  T  F
alg2 copt GCTGCCGACACCGTTGTTGTTAACTCTAACTTGACCAAAAACACCTTCCACCAGACCTTC
          A  A  D  T  V  V  V  N  S  N  F  T  K  N  T  F  H  Q  T  F 550        560        570        580        590        600
         ....|....|....|....|....|....|....|....|....|....|....|....|
alg2     aagtatttatccaatgatccagacgtcatttatccatgcgtggatttatcaagaatcgaa
          K  Y  L  S  N  D  P  D  V  I  Y  P  C  V  D  L  S  T  I  E
alg2 copt AAATACCTGTCTAACGACCCGGACGTTATCTACCCGTGCGTTGACCTGTCTACCATCGAA
          K  Y  L  S  N  D  P  D  V  I  Y  P  C  V  D  L  S  T  I  E 610        620        630        640        650        660
         ....|....|....|....|....|....|....|....|....|....|....|....|
alg2     attgaagatattgacaagaaatttttcaaaacagtgtttaacgaaggcgatagatttttac
          I  E  D  I  D  K  K  F  F  K  T  V  F  N  E  G  D  R  F  Y
alg2 copt ATCGAAGACATCGACAAAAAATTCTTCAAAACCGTTTTCAACGAAGGTGACCGTTTCTAC
          I  E  D  I  D  K  K  F  F  K  T  V  F  N  E  G  D  R  F  Y 670        680        690        700        710        720
         ....|....|....|....|....|....|....|....|....|....|....|....|
alg2     ctaagtataaatcgttttgagaaaaaaaaggatgttgcgctggctataaaggcttttgcg
          L  S  I  N  R  F  E  K  K  K  D  V  A  L  A  I  K  A  F  A
alg2 copt CTGTCTATCAACCGTTTCGAAAAAAAAAAAGACGTTGCTCTGGCTATCAAAGCTTTCGCT
          L  S  I  N  R  F  E  K  K  K  D  V  A  L  A  I  K  A  F  A 730        740        750        760        770        780
         ....|....|....|....|....|....|....|....|....|....|....|....|
alg2     ttatctgaagatcaaatcaatgacaacgttaagttagttatttgcggtggttatgacgag
          L  S  E  D  Q  I  N  D  N  V  K  L  V  I  C  G  G  Y  D  E
alg2 copt CTGTCTGAAGACCAGATCAACGACAACGTTAAACTGGTTATCTGCGGTGGTTACGACGAA
          L  S  E  D  Q  I  N  D  N  V  K  L  V  I  C  G  G  Y  D  E 790        800        810        820        830        840
         ....|....|....|....|....|....|....|....|....|....|....|....|
alg2     agggttgcagaaaatgtggagtacttgaaggaactacagtctctggccgatgaatacgaa
          R  V  A  E  N  V  E  Y  L  K  E  L  Q  S  L  A  D  E  Y  E
alg2 copt CGTGTTGCTGAAAACGTTGAATACCTGAAAGAACTGCAGTCTCTGGCTGACGAATACGAA
          R  V  A  E  N  V  E  Y  L  K  E  L  Q  S  L  A  D  E  Y  E 850        860        870        880        890        900
         ....|....|....|....|....|....|....|....|....|....|....|....|
alg2     ttatcccatacaaccatatactaccaagaaataaagcgcgtctccgatttagagtcattc
          L  S  H  T  T  I  Y  Y  Q  E  I  K  R  V  S  D  L  E  S  F
alg2 copt CTGTCTCACACCACCATCTACTACCAGGAAATCAAACGTGTTTCTGACCTGGAATCTTTC
          L  S  H  T  T  I  Y  Y  Q  E  I  K  R  V  S  D  L  E  S  F
```

Figure 14 (continued)

```
              910       920       930       940       950       960
         ....|....|....|....|....|....|....|....|....|....|....|....|
alg2     aaaaccaataatagtaaaattacatttttaacttccatttcatcatctctgaaagaatta
          K  T  N  N  S  K  I  I  F  L  T  S  I  S  S  S  L  K  E  L
alg2 Copt AAAACCAACAACTCTAAAATCATCTTCCTGACCTCTATCTCTTCTTCTCTGAAAGAACTG
          K  T  N  N  S  K  I  I  F  L  T  S  I  S  S  S  L  K  E  L 970       980       990      1000      1010      1020
         ....|....|....|....|....|....|....|....|....|....|....|....|
alg2     ctgctcgaaagaaccgaaatgttattgtatacaccaggatatgagcactttggtattgtt
          L  L  E  R  T  E  M  L  L  Y  T  P  A  Y  E  H  F  G  I  V
alg2 Copt CTGCTGGAACGTACCGAAATGCTGCTGTACACCCCGGCTTACGAACACTTCGGTATCGTT
          L  L  E  R  T  E  M  L  L  Y  T  P  A  Y  E  H  F  G  I  V 1030      1040      1050      1060      1070      1080
         ....|....|....|....|....|....|....|....|....|....|....|....|
alg2     cctttagaagccatgaaattaggtaagcctgtactagcagtaaacaatggaggtcctttg
          P  L  E  A  M  K  L  G  K  P  V  L  A  V  N  N  G  G  P  L
alg2 Copt CCGCTGGAAGCTATGAAACTGGGTAAACCGGTTCTGGCTGTTAACAACGGTGGTCCGCTG
          P  L  E  A  M  K  L  G  K  P  V  L  A  V  N  N  G  G  P  L 1090      1100      1110      1120      1130      1140
         ....|....|....|....|....|....|....|....|....|....|....|....|
alg2     gagactatcaaatcttacgttgctggtgaaaatgaaagttctgccactgggtggctaaaa
          E  T  I  K  S  Y  V  A  G  E  N  E  S  S  A  T  G  W  L  K
alg2 Copt GAAACCATCAAATCTTACGTTGCTGGTGAAAACGAATCTTCTGCTACCGGTTGGCTGAAA
          E  T  I  K  S  Y  V  A  G  E  N  E  S  S  A  T  G  W  L  K 1150      1160      1170      1180      1190      1200
         ....|....|....|....|....|....|....|....|....|....|....|....|
alg2     cctgccgtcccctattcaatgggctactgcaattgatgaaagcagaaagatcttgcagaac
          P  A  V  P  I  Q  W  A  T  A  I  D  E  S  R  K  I  L  Q  N
alg2 Copt CCGGCTGTTCCGATCCAGTGGGCTACCGCTATCGACGAATCTCGTAAAATCCTGCAGAAC
          P  A  V  P  I  Q  W  A  T  A  I  D  E  S  R  K  I  L  Q  N 1210      1220      1230      1240      1250      1260
         ....|....|....|....|....|....|....|....|....|....|....|....|
alg2     ggttctgtgaactttgagaggaatggcccgctaagagtcaagaaatactttcctagggaa
          G  S  V  N  F  E  R  N  G  P  L  R  V  K  K  Y  F  S  R  E
alg2 Copt GGTTCTGTTAACTTCGAACGTAACGGTCCGCTGCGTGTTAAAAAATACTTCTCTCGTGAA
          G  S  V  N  F  E  R  N  G  P  L  R  V  K  K  Y  F  S  R  E 1270      1280      1290      1300      1310      1320
         ....|....|....|....|....|....|....|....|....|....|....|....|
alg2     gcaatgactcagtcatttgaagaaaacgtcgagaaagtcatatggaaagaaaaaaagtat
          A  M  T  Q  S  F  E  E  N  V  E  K  V  I  W  K  E  K  K  Y
alg2 Copt GCTATGACCCAGTCTTTCGAAGAAAACGTTGAAAAAGTTATCTGGAAAGAAAAAAAATAC
          A  M  T  Q  S  F  E  E  N  V  E  K  V  I  W  K  E  K  K  Y 1330      1340      1350      1360      1370      1380
         ....|....|....|....|....|....|....|....|....|....|....|....|
alg2     tatccttgggaaatattcggtatttcattctctaattttattttgcatatggcatttata
          Y  P  W  E  I  F  G  I  S  F  S  N  F  I  L  H  M  A  F  I
alg2 Copt TACCCGTGGGAAATCTTCGGTATCTCTTTCTCTAACTTCATCCTGCACATGGCTTTCATC
          Y  P  W  E  I  F  G  I  S  F  S  N  F  I  L  H  M  A  F  I
```

Figure 14 (continued)

```
           1390      1400      1410      1420      1430      1440
           ....|....|....|....|....|....|....|....|....|....|....|....|
alg2       aaaattctacccaataatccatgcccttcctatttatggccactttatggtattatat
            K  I  L  P  N  N  P  W  P  F  L  F  M  A  T  F  M  V  L  Y
alg2 cOpt  AAAATCCTGCCGAACAACCCGTGGCCGTTCCTGTTCATGGCTACCTTCATGGTTCTGTAC
            K  I  L  P  N  N  P  W  P  F  L  F  M  A  T  F  M  V  L  Y 1450      1460      1470      1480      1490      1500
           ....|....|....|....|....|....|....|....|....|....|....|....|
alg2       tttaagaactacttatggggaattactgggcatttgtattcgctctctcctaccctat
            F  K  N  Y  L  W  G  I  Y  W  A  F  V  F  A  L  S  Y  P  Y
alg2 cOpt  TTCAAAAACTACCTGTGGGGTATCTACTGGGCTTTCGTTTTCGCTCTGTCTTACCCGTAC
            F  K  N  Y  L  W  G  I  Y  W  A  F  V  F  A  L  S  Y  P  Y 1510
           ....|....|..
alg2       gaagaaatataa
            E  E  I  *
alg2 cOpt  GAAGAAATCTAA
            E  E  I  *
```

Figure 14 (continued)

ALIGNMENT

```
              10         20         30         40         50         60
          ....|....|....|....|....|....|....|....|....|....|....|....|
alg13     atgggtattattgaagaaaaggctcttttgttacgtgtggggcaacggtgccattccca
          M  G  I  I  E  E  K  A  L  F  V  T  C  G  A  T  V  P  F  P
alg13 copt ATGGGTATCATCGAAGAAAAAGCTCTGTTCGTTACCTGCGGTGCTACCGTTCCGTTCCCG
          M  G  I  I  E  E  K  A  L  F  V  T  C  G  A  T  V  P  F  P 70         80         90        100        110        120
          ....|....|....|....|....|....|....|....|....|....|....|....|
alg13     aagctcgtctcatgtgtgctaagcgacgaattctgccagaattgattcaatatggattc
          K  L  V  S  C  V  L  S  D  E  F  C  Q  E  L  I  Q  Y  G  F
alg13 copt AAACTGGTTTCTTGCGTTCTGTCTGACGAATTCTGCCAGGAACTGATCCAGTACGGTTTC
          K  L  V  S  C  V  L  S  D  E  F  C  Q  E  L  I  Q  Y  G  F 130        140        150        160        170        180
          ....|....|....|....|....|....|....|....|....|....|....|....|
alg13     gtacgtctaatcattcagtttgggagaaacacagttctgaatttgagcatttagtgcaa
          V  R  L  I  I  Q  F  G  R  N  Y  S  S  E  F  E  H  L  V  Q
alg13 copt GTTCGTCTGATCATCCAGTTCGGTCGTAACTACTCTTCTGAATTCGAACACCTGGTTCAG
          V  R  L  I  I  Q  F  G  R  N  Y  S  S  E  F  E  H  L  V  Q 190        200        210        220        230        240
          ....|....|....|....|....|....|....|....|....|....|....|....|
alg13     gaacgcgggggccaaagagaaagccaaaaaattccaattgaccagtttggctgtggcgac
          E  R  G  G  Q  R  E  S  Q  K  I  P  I  D  Q  F  G  C  G  D
alg13 copt GAACGTGGTGGTCAGCGTGAATCTCAGAAAATCCCGATCGACCAGTTCGGTTGCGGTGAC
          E  R  G  G  Q  R  E  S  Q  K  I  P  I  D  Q  F  G  C  G  D 250        260        270        280        290        300
          ....|....|....|....|....|....|....|....|....|....|....|....|
alg13     accgcaagacagtatgtcctgatgaacgggaaattaaaggtgatcgggtttgacttttcg
          T  A  R  Q  Y  V  L  M  N  G  K  L  K  V  I  G  F  D  F  S
alg13 copt ACCGCTCGTCAGTACGTTCTGATGAACGGTAAACTGAAAGTTATCGGTTTCGACTTCTCT
          T  A  R  Q  Y  V  L  M  N  G  K  L  K  V  I  G  F  D  F  S 310        320        330        340        350        360
          ....|....|....|....|....|....|....|....|....|....|....|....|
alg13     accaagatgcaaagtattatacgtgattattcagatttggtcatatcacacgctggaacg
          T  K  M  Q  S  I  I  R  D  Y  S  D  L  V  I  S  H  A  G  T
alg13 copt ACCAAAATGCAGTCTATCATCCGTGACTACTCTGACCTGGTTATCTCTCACGCTGGTACC
          T  K  M  Q  S  I  I  R  D  Y  S  D  L  V  I  S  H  A  G  T 370        380        390        400        410        420
          ....|....|....|....|....|....|....|....|....|....|....|....|
alg13     ggctctatactagattctctacggttgaataaaccgttgatagtttgcgtaaacgattct
          G  S  I  L  D  S  L  R  L  N  K  P  L  I  V  C  V  N  D  S
alg13 copt GGTTCTATCCTGGACTCTCTGCGTCTGAACAAACCGCTGATCGTTTGCGTTAACGACTCT
          G  S  I  L  D  S  L  R  L  N  K  P  L  I  V  C  V  N  D  S
```

Figure 15

```
              430       440       450       460       470       480
          ....|....|....|....|....|....|....|....|....|....|....|....|
alg13     ttgatggataaccaccagcagcagatagcagacaagttgtagagttgggctacgtatgg
          L  M  D  N  H  Q  Q  I  A  D  K  F  V  E  L  G  Y  V  W
alg13 cOpt CTGATGGACAACCACCAGCAGCAGATCGGTGACAAATTCGTTGAACTGGGTTACGTTTGG
          L  M  D  N  H  Q  Q  I  A  D  K  F  V  E  L  G  Y  V  W 490       500       510       520       530       540
          ....|....|....|....|....|....|....|....|....|....|....|....|
alg13     tcttgtgcacccactgaaacaggttgatagctggttacgtgcatctcaaacagagaaa
          S  C  A  P  T  E  T  G  L  I  A  G  L  R  A  S  Q  T  E  K
alg13 cOpt TCTTGCGCTCCGACCGAAACCGGTCTGATCGCTGGTCTGCGTGCTTCTCAGACCGAAAAA
          S  C  A  P  T  E  T  G  L  I  A  G  L  R  A  S  Q  T  E  K 550       560       570       580       590       600
          ....|....|....|....|....|....|....|....|....|....|....|....|
alg13     ctcaaaccattcccagtttctcataacccgtcatctgagcgattgctagttgaaactata
          L  K  P  F  P  V  S  H  N  P  S  F  E  R  L  L  V  E  T  I
alg13 cOpt CTGAAACCGTTCCCGGTTTCTCACAACCCGTCTTTCGAACGTCTGCTGGTTGAAACCATC
          L  K  P  F  P  V  S  H  N  P  S  F  E  R  L  L  V  E  T  I ....|....
alg13     tacagctag
          Y  S  *
alg13 cOpt TACTCTTAA
          Y  S  *
```

Figure 15 (continued)

ALIGNMENT

```
              10         20         30         40         50         60
         ....|....|....|....|....|....|....|....|....|....|....|....|
alg14      atgaaaacggcctacttggcgtcattggtgctcatcgtatcgacagcatatgttattagg
            M  K  T  A  Y  L  A  S  L  V  L  I  V  S  T  A  Y  V  I  R
alg14 copt ATGAAAACCGCTTACCTGGCTTCTCTGGTTCTGATCGTTTCTACCGCTTACGTTATCCGT
            M  K  T  A  Y  L  A  S  L  V  L  I  V  S  T  A  Y  V  I  R 70         80         90        100        110        120
         ....|....|....|....|....|....|....|....|....|....|....|....|
alg14      ttgatagcgattctgccttttttccacactcaagcaggtacagaaaaggatacgaaagat
            L  I  A  I  L  P  F  F  H  T  Q  A  G  T  E  K  D  T  K  D
alg14 copt CTGATCGCTATCCTGCCGTTCTTCCACACCCAGGCTGGTACCGAAAAGACACCAAAGAC
            L  I  A  I  L  P  F  F  H  T  Q  A  G  T  E  K  D  T  K  D 130        140        150        160        170        180
         ....|....|....|....|....|....|....|....|....|....|....|....|
alg14      ggagttaacctactgaaaatacgaaaatcgtcaaagaaaccgctcaagattttgtattc
            G  V  N  L  L  K  I  R  K  S  S  K  K  P  L  K  I  F  V  F
alg14 copt GGTGTTAACCTGCTGAAAATCCGTAAATCTTCTAAAAAACCGCTGAAAATCTTCGTTTTC
            G  V  N  L  L  K  I  R  K  S  S  K  K  P  L  K  I  F  V  F 190        200        210        220        230        240
         ....|....|....|....|....|....|....|....|....|....|....|....|
alg14      ttaggatcgggaggtcatactggtgaaatgatccgtcttctagaaaaattaccaggatctt
            L  G  S  G  G  H  T  G  E  M  I  R  L  L  E  N  Y  Q  D  L
alg14 copt CTGGGTTCTGGTGGTCACACCGGTGAAATGATCCGTCTGCTGGAAAACTACCAGGACCTG
            L  G  S  G  G  H  T  G  E  M  I  R  L  L  E  N  Y  Q  D  L 250        260        270        280        290        300
         ....|....|....|....|....|....|....|....|....|....|....|....|
alg14      ttactgggtaagtcgattgtgtacttgggttattctgatgaggcttccaggcaaagattc
            L  L  G  K  S  I  V  Y  L  G  Y  S  D  E  A  S  R  Q  R  F
alg14 copt CTGCTGGGTAAATCTATCGTTTACCTGGGTTACTCTGACGAAGCTTCTCGTCAGCGTTTC
            L  L  G  K  S  I  V  Y  L  G  Y  S  D  E  A  S  R  Q  R  F 310        320        330        340        350        360
         ....|....|....|....|....|....|....|....|....|....|....|....|
alg14      gcccactttataaaaaaatttggtcattgcaaagtaaaatactatgaattcatgaaagct
            A  H  F  I  K  K  F  G  H  C  K  V  K  Y  Y  E  F  M  K  A
alg14 copt GCTCACTTCATCAAAAAATTCGGTCACTGCAAAGTTAAATACTACGAATTCATGAAAGCT
            A  H  F  I  K  K  F  G  H  C  K  V  K  Y  Y  E  F  M  K  A 370        380        390        400        410        420
         ....|....|....|....|....|....|....|....|....|....|....|....|
alg14      agggaagttaaagcgactctcctacaaagtgtaaagaccatcattggaacgttggtacaa
            R  E  V  K  A  T  L  L  Q  S  V  K  T  I  I  G  T  L  V  Q
alg14 copt CGTGAAGTTAAAGCTACCCTGCTGCAGTCTGTTAAAACCATCATCGGTACCCTGGTTCAG
            R  E  V  K  A  T  L  L  Q  S  V  K  T  I  I  G  T  L  V  Q
```

Figure 16

```
           430        440        450        460        470        480
        ....|....|....|....|....|....|....|....|....|....|....|....|
alg14       tcttttgtgcacgtggttagaatcagatttgctatgtgtggttcccctcatctgttttta
            S   F   V   H   V   V   R   I   R   F   A   M   C   G   S   P   H   L   F   L
alg14 Copt  TCTTTCGTTCACGTTGTTCGTATCCGTTTCGCTATGTGCGGTTCTCCGCACCTGTTCCTG
            S   F   V   H   V   V   R   I   R   F   A   M   C   G   S   P   H   L   F   L 490        500        510        520        530        540
        ....|....|....|....|....|....|....|....|....|....|....|....|
alg14       ttgaatgggcctggaacatgctgtataatatcctttggttgaaaattatggaactgctt
            L   N   G   P   G   T   C   C   I   I   S   F   W   L   K   I   M   E   L   L
alg14 Copt  CTGAACGGTCCGGGGTACCTGCTGCATCATCTCTTTCTGGCTGAAAAATCATGGAACTGCTG
            L   N   G   P   G   T   C   C   I   I   S   F   W   L   K   I   M   E   L   L 550        560        570        580        590        600
        ....|....|....|....|....|....|....|....|....|....|....|....|
alg14       ttgcccctgttgggttcctcccatatagttatgtagaatcgctggcaaggattaatact
            L   P   L   L   G   S   S   H   I   V   Y   V   E   S   L   A   R   I   N   T
alg14 Copt  CTGCCGCTGCTGGGTTCTTCTCACATCGTTTACGTTGAATCTCTGGCTCGTATCAACACC
            L   P   L   L   G   S   S   H   I   V   Y   V   E   S   L   A   R   I   N   T 610        620        630        640        650        660
        ....|....|....|....|....|....|....|....|....|....|....|....|
alg14       cctagtctgaccggaaaaatattatattgggtagtggatgaattcattgtccagtggcaa
            P   S   L   T   G   K   I   L   Y   W   V   V   D   E   F   I   V   Q   W   Q
alg14 Copt  CCGTCTCTGACCGGTAAAATCCTGTACTGGGTTGTTGACGAATTCATCGTTCAGTGGCAG
            P   S   L   T   G   K   I   L   Y   W   V   V   D   E   F   I   V   Q   W   Q 670        680        690        700        710
        ....|....|....|....|....|....|....|....|....|....|
alg14       gaattgagggacaattattttaccaagatccaagtgggtcggcatccttgtttaa
            E   L   R   D   N   Y   L   P   R   S   K   W   F   G   I   L   V   *
alg14 Copt  GAACTGCGTGACAACTACCTGCCGCGTTCTAAATGGTTCGGTATCCTGGTTTAA
            E   L   R   D   N   Y   L   P   R   S   K   W   F   G   I   L   V   *
```

Figure 16 (continued)

ALIGNMENT

```
                 10         20         30         40         50         60
          ....|....|....|....|....|....|....|....|....|....|....|....|
rft1      atggcgaaaaaaaactcacaattgccctctactagtgagcagatcttggaaaggtccaca
           M  A  K  K  N  S  Q  L  P  S  T  S  E  Q  I  L  E  R  S  T
rft1 copt ATGGCTAAAAAAAACTCTCAGCTGCCGTCTACCTCTGAACAGATCCTGGAACGTTCTACC
           M  A  K  K  N  S  Q  L  P  S  T  S  E  Q  I  L  E  R  S  T 70         80         90        100        110        120
          ....|....|....|....|....|....|....|....|....|....|....|....|
rft1      acaggagctaccttcctcatgatgggccaactttttcaccaaactggtaacgttcatacta
           T  G  A  T  F  L  M  M  G  Q  L  F  T  K  L  V  T  F  I  L
rft1 copt ACCGGTGCTACCTTCCTGATGATGGGTCAGCTGTTCACCAAACTGGTTACCTTCATCCTG
           T  G  A  T  F  L  M  M  G  Q  L  F  T  K  L  V  T  F  I  L 130        140        150        160        170        180
          ....|....|....|....|....|....|....|....|....|....|....|....|
rft1      aataatttgttgatcaggtttctgtcgcccagaatttttcggtatcacggcctttctagaa
           N  N  L  L  I  R  F  L  S  P  R  I  F  G  I  T  A  F  L  E
rft1 copt AACAACCTGCTGATCCGTTTCCTGTCTCCGCGTATCTTCGGTATCACCGCTTTCCTGGAA
           N  N  L  L  I  R  F  L  S  P  R  I  F  G  I  T  A  F  L  E 190        200        210        220        230        240
          ....|....|....|....|....|....|....|....|....|....|....|....|
rft1      tttatacagggcacagtgttattttttagcagagatgcgattcgtctgtcgacgttgaga
           F  I  Q  G  T  V  L  F  F  S  R  D  A  I  R  L  S  T  L  R
rft1 copt TTCATCCAGGGTACCGTTCTGTTCTTCTCTCGTGACGCTATCCGTCTGTCTACCCTGCGT
           F  I  Q  G  T  V  L  F  F  S  R  D  A  I  R  L  S  T  L  R 250        260        270        280        290        300
          ....|....|....|....|....|....|....|....|....|....|....|....|
rft1      atctcagactccggtaatggaataatcgatgatgacgacgaggaggagtaccaggaaact
           I  S  D  S  G  N  G  I  I  D  D  D  D  E  E  E  Y  Q  E  T
rft1 copt ATCTCTGACTCTGGTAACGGTATCATCGACGACGACGACGAAGAAGAATACCAGGAAACC
           I  S  D  S  G  N  G  I  I  D  D  D  D  E  E  E  Y  Q  E  T 310        320        330        340        350        360
          ....|....|....|....|....|....|....|....|....|....|....|....|
rft1      cattacaagtctaaagtttttgcaaaccgcagtcaatttgttacattccgttttggatc
           H  Y  K  S  K  V  L  Q  T  A  V  N  F  A  Y  I  P  F  W  I
rft1 copt CACTACAAATCTAAAGTTCTGCAGACCGCTGTTAACTTCGCTTACATCCCGTTCTGGATC
           H  Y  K  S  K  V  L  Q  T  A  V  N  F  A  Y  I  P  F  W  I 370        380        390        400        410        420
          ....|....|....|....|....|....|....|....|....|....|....|....|
rft1      gggtttccactgtccattggtcttatcgcctggcagtacagaaacatcaacgcgtatttc
           G  F  P  L  S  I  G  L  I  A  W  Q  Y  R  N  I  N  A  Y  F
rft1 copt GGTTTCCCGCTGTCTATCGGTCTGATCGCTTGGCAGTACCGTAACATCAACGCTTACTTC
           G  F  P  L  S  I  G  L  I  A  W  Q  Y  R  N  I  N  A  Y  F
```

Figure 17

```
              430        440        450        460        470        480
          ....|....|....|....|....|....|....|....|....|....|....|....|
rftl      atcactcttccattcttcagtggtcgattttcttatctggctgagtatcatcgtggag
           I  T  L  P  F  F  R  W  S  I  F  L  I  W  L  S  I  I  V  E
rftl copt ATCACCCTGCCGTTCTTCCGTTGGTCTATCTTCCTGATCTGGCTGTCTATCATCGTTGAA
           I  T  L  P  F  F  R  W  S  I  F  L  I  W  L  S  I  I  V  E 490        500        510        520        530        540
          ....|....|....|....|....|....|....|....|....|....|....|....|
rftl      ctgttaagcgagccattcttcatcgtcaaccagttatgttgaactatgccgcaaggtca
           L  L  S  E  P  F  F  I  V  N  Q  F  M  L  N  Y  A  A  R  S
rftl copt CTGCTGTCTGAACCGTTCTTCATCGTTAACCAGTTCATGCTGAACTACGCTGCTCGTTCT
           L  L  S  E  P  F  F  I  V  N  Q  F  M  L  N  Y  A  A  R  S 550        560        570        580        590        600
          ....|....|....|....|....|....|....|....|....|....|....|....|
rftl      agatttgaaagcatcgcggtgactacaggatgtattgtcaatttatagttgttatgcc
           R  F  E  S  I  A  V  T  T  G  C  I  V  N  F  I  V  V  Y  A
rftl copt CGTTTCGAATCTATCGCTGTTACCACCGGTTGCATCGTTAACTTCATCGTTGTTTACGCT
           R  F  E  S  I  A  V  T  T  G  C  I  V  N  F  I  V  V  Y  A 610        620        630        640        650        660
          ....|....|....|....|....|....|....|....|....|....|....|....|
rftl      gttcagcaatcccgctaccaatggggggttgtcacatcggacattgacaaagaaggcatc
           V  Q  Q  S  R  Y  P  M  G  V  V  T  S  D  I  D  K  E  G  I
rftl copt GTTCAGCAGTCTCGTTACCCGATGGGTGTTGTTACCTCTGACATCGACAAAGAAGGTATC
           V  Q  Q  S  R  Y  P  M  G  V  V  T  S  D  I  D  K  E  G  I 670        680        690        700        710        720
          ....|....|....|....|....|....|....|....|....|....|....|....|
rftl      gccatatggcatttgcctgggaaagttagcacatcgatcaccctgctagcatgttac
           A  I  L  A  F  A  L  G  K  L  A  H  S  I  T  L  L  A  C  Y
rftl copt GCTATCCTGGCTTTCGCTCTGGGTAAACTGGCTCACTCTATCACCCTGCTGGCTTGCTAC
           A  I  L  A  F  A  L  G  K  L  A  H  S  I  T  L  L  A  C  Y 730        740        750        760        770        780
          ....|....|....|....|....|....|....|....|....|....|....|....|
rftl      tactgggactatctcaagaatttcaaaccaaagaaattgttcagtaccaggctaacgaag
           Y  W  D  Y  L  K  N  F  K  P  K  K  L  F  S  T  R  L  T  K
rftl copt TACTGGGACTACCTGAAAAACTTCAAACCGAAAAAACTGTTCTCTACCCGTCTGACCAAA
           Y  W  D  Y  L  K  N  F  K  P  K  K  L  F  S  T  R  L  T  K 790        800        810        820        830        840
          ....|....|....|....|....|....|....|....|....|....|....|....|
rftl      ataaaaacgcgtgaaaataacgaattgaagaaaggctacccaaagagcacatcttatttt
           I  K  T  R  E  N  N  E  L  K  K  G  Y  P  K  S  T  S  Y  F
rftl copt ATCAAAACCCGTGAAAACAACGAACTGAAAAAAGGTTACCCGAAATCTACCTCTTACTTC
           I  K  T  R  E  N  N  E  L  K  K  G  Y  P  K  S  T  S  Y  F 850        860        870        880        890        900
          ....|....|....|....|....|....|....|....|....|....|....|....|
rftl      ttccaaaacgacatttacagcacttcaaaaaagtttatttcaactatgttttaagcat
           F  Q  N  D  I  L  Q  H  F  K  K  V  Y  F  Q  L  C  F  K  H
rftl copt TTCCAGAACGACATCCTGCAGCACTTCAAAAAAGTTTACTTCCAGCTGTGCTTCAAACAC
           F  Q  N  D  I  L  Q  H  F  K  K  V  Y  F  Q  L  C  F  K  H
```

Figure 17 (continued)

```
                910       920       930       940       950       960
           ....|....|....|....|....|....|....|....|....|....|....|....|
rft1       ttgttgacagagggtgataagttgattatcaattcttatgtactgtggaagaacaaggc
            L  L  T  E  G  D  K  L  I  I  N  S  L  C  T  V  E  E  Q  G
rft1 copt  CTGCTGACCGAAGGTGACAAAACTGATCATCAACTCTCTGTGCACCGTTGAAGAACAGGGT
            L  L  T  E  G  D  K  L  I  I  N  S  L  C  T  V  E  E  Q  G 970       980       990      1000      1010      1020
           ....|....|....|....|....|....|....|....|....|....|....|....|
rft1       atttacgctctattgtcgaactatggatcgctactaacaagattattatttgcgccgatc
            I  Y  A  L  L  S  N  Y  G  S  L  L  T  R  L  L  F  A  P  I
rft1 copt  ATCTACGCTCTGCTGTCTAACTACGGTTCTCTGCTGACCCGTCTGCTGTTCGCTCCGATC
            I  Y  A  L  L  S  N  Y  G  S  L  L  T  R  L  L  F  A  P  I 1030      1040      1050      1060      1070      1080
           ....|....|....|....|....|....|....|....|....|....|....|....|
rft1       gaagaatctctgcggttatttttggcccgttattatcctcgcataaccctaaaaaattca
            E  E  S  L  R  L  F  L  A  R  L  L  S  S  H  N  P  K  N  L
rft1 copt  GAAGAATCTCTGCGTCTGTTCCTGGCTCGTCTGCTGTCTTCTCACAACCCGAAAAACCTG
            E  E  S  L  R  L  F  L  A  R  L  L  S  S  H  N  P  K  N  L 1090      1100      1110      1120      1130      1140
           ....|....|....|....|....|....|....|....|....|....|....|....|
rft1       aaactatctattgaagtcctggtgaatttaacaaggttttacatatacttatcgttaatg
            K  L  S  I  E  V  L  V  N  L  T  R  F  Y  I  Y  L  S  L  M
rft1 copt  AAACTGTCTATCGAAGTTCTGGTTAACCTGACCCGTTTCTACATCTACCTGTCTCTGATG
            K  L  S  I  E  V  L  V  N  L  T  R  F  Y  I  Y  L  S  L  M 1150      1160      1170      1180      1190      1200
           ....|....|....|....|....|....|....|....|....|....|....|....|
rft1       atcattgtatttgggcctgccaattcatcctttttattgcagttcttgattggctcgaaa
            I  I  V  F  G  P  A  N  S  S  F  L  L  Q  F  L  I  G  S  K
rft1 copt  ATCATCGTTTTCGGTCCGGCTAACTCTTCTTTCCTGCTGCAGTTCCTGATCGGTTCTAAA
            I  I  V  F  G  P  A  N  S  S  F  L  L  Q  F  L  I  G  S  K 1210      1220      1230      1240      1250      1260
           ....|....|....|....|....|....|....|....|....|....|....|....|
rft1       tggtccactagttccgttttggacactataagagtctactgcttttacatcccatttta
            W  S  T  T  S  V  L  D  T  I  R  V  Y  C  F  Y  I  P  F  L
rft1 copt  TGGTCTACCACCTCTGTTCTGGACACCATCCGTGTTTACTGCTTCTACATCCCGTTCCTG
            W  S  T  T  S  V  L  D  T  I  R  V  Y  C  F  Y  I  P  F  L 1270      1280      1290      1300      1310      1320
           ....|....|....|....|....|....|....|....|....|....|....|....|
rft1       tcgcttaatggtattttgaagcttttttccagagtgtagccactggtgaccaaatttg
            S  L  N  G  I  F  E  A  F  F  Q  S  V  A  T  G  D  Q  I  L
rft1 copt  TCTCTGAACGGTATCTTCGAAGCTTTCTTCCAGTCTGTTGCTACCGGTGACCAGATCCTG
            S  L  N  G  I  F  E  A  F  F  Q  S  V  A  T  G  D  Q  I  L 1330      1340      1350      1360      1370      1380
           ....|....|....|....|....|....|....|....|....|....|....|....|
rft1       aaacattcatattttatgatggccttttctggtattttcctgctcaattcctggcttctt
            K  H  S  Y  F  M  M  A  F  S  G  I  F  L  L  N  S  W  L  L
rft1 copt  AAACACTCTTACTTCATGATGGCTTTCTCTGGTATCTTCCTGCTGAACTCTTGGCTGCTG
            K  H  S  Y  F  M  M  A  F  S  G  I  F  L  L  N  S  W  L  L
```

Figure 17 (continued)

```
              1390      1400      1410      1420      1430      1440
         ....|....|....|....|....|....|....|....|....|....|....|....|
rft1     attgaaaaactcaaactatcaatcgaaggcttgatattgagtaacatcattaacatggtg
          I  E  K  L  K  L  S  I  E  G  L  I  L  S  N  I  I  N  M  V
rft1 cOpt ATCGAAAAACTGAAACTGTCTATCGAAGGTCTGATCCTGTCTAACATCATCAACATGGTT
          I  E  K  L  K  L  S  I  E  G  L  I  L  S  N  I  I  N  M  V 1450      1460      1470      1480      1490      1500
         ....|....|....|....|....|....|....|....|....|....|....|....|
rft1     ttgagaatattgtattgtggagtttcttgaataaatttcatagggaactgtttacagat
          L  R  I  L  Y  C  G  V  F  L  N  K  F  H  R  E  L  F  T  D
rft1 cOpt CTGCGTATCCTGTACTGCGGTGTTTTCCTGAACAAATTCCACCGTGAACTGTTCACCGAC
          L  R  I  L  Y  C  G  V  F  L  N  K  F  H  R  E  L  F  T  D 1510      1520      1530      1540      1550      1560
         ....|....|....|....|....|....|....|....|....|....|....|....|
rft1     tcctcttttttcttcaattttaaggatttcaaaacagttattattgctggctcaacgatc
          S  S  F  F  F  N  F  K  D  F  K  T  V  I  I  A  G  S  T  I
rft1 cOpt TCTTCTTTCTTCTTGAACTTCAAAGACTTCAAAACCGTTATCATCGCTGGTTCTACCATC
          S  S  F  F  F  N  F  K  D  F  K  T  V  I  I  A  G  S  T  I 1570      1580      1590      1600      1610      1620
         ....|....|....|....|....|....|....|....|....|....|....|....|
rft1     tgtctacttgactggtggtttattgggtacgttaaaaatttacaacaatttgttgttaac
          C  L  L  D  W  W  F  I  G  Y  V  K  N  L  Q  Q  F  V  V  N
rft1 cOpt TGCCTGCTGGACTGGTGGTTCATCGGTTACGTTAAAAACCTGCAGCAGTTCGTTGTTAAC
          C  L  L  D  W  W  F  I  G  Y  V  K  N  L  Q  Q  F  V  V  N 1630      1640      1650      1660      1670      1680
         ....|....|....|....|....|....|....|....|....|....|....|....|
rft1     gtattattcgcaatgggattgttagcgttaatttggtcaaggagcgccaaaccatacaa
          V  L  F  A  M  G  L  L  A  L  I  L  V  K  E  R  Q  T  I  Q
rft1 cOpt GTTCTGTTCGCTATGGGTCTGCTGGCTCTGATCCTGGTTAAAGAACGTCAGACCATCCAG
          V  L  F  A  M  G  L  L  A  L  I  L  V  K  E  R  Q  T  I  Q 1690      1700      1710      1720
         ....|....|....|....|....|....|....|....|
rft1     tcttttattaacaagagggcggtttccaattctaaagatgtataa
          S  F  I  N  K  R  A  V  S  N  S  K  D  V  *
rft1 cOpt TCTTTCATCAACAAACGTGCTGTTTCTAACTCTAAAGACGTTTAA
          S  F  I  N  K  R  A  V  S  N  S  K  D  V  *
```

Figure 17 (continued)

ALIGNMENT

GLYCOSYLATED PROTEIN EXPRESSION IN PROKARYOTES

This application claims priority benefit of U.S. Provisional Patent Application Ser. No. 61/018,772, filed Jan. 3, 2008, which is hereby incorporated by reference in its entirety.

FIELD OF INVENTION

The present invention relates to glycosylated protein expression in prokaryotes.

BACKGROUND OF THE INVENTION

Glycotherapeutics

Protein-based therapeutics currently represent one in every four new drugs approved by the FDA (Walsh, G., "Biopharmaceutical Benchmarks," *Nat Biotechnol* 18:831-3 (2000); Walsh, G, "Biopharmaceutical Benchmarks," *Nat Biotechnol* 21:865-70 (2003); and Walsh, G, "Biopharmaceutical Benchmarks," *Nat Biotechnol* 24:769-76 (2006)).

While several protein therapeutics can be produced using a prokaryotic expression system such as *E. coli* (e.g., insulin), the vast majority of therapeutic proteins require additional post-translational modifications, thought to be absent in prokaryotes, to attain their full biological function. In particular, N-linked protein glycosylation is predicted to affect more than half of all eukaryotic protein species (Apweiler et al., "On the Frequency of Protein Glycosylation, as Deduced From Analysis of the SWISS-PROT Database," *Biochim Biophys Acta* 1473:4-8 (1999)) and is often essential for proper folding, pharmacokinetic stability, tissue targeting and efficacy for a large number of proteins (Helenius et al., "Intracellular Functions of N-linked Glycans," *Science* 291:2364-9 (2001)). Since most bacteria do not glycosylate their own proteins, expression of most therapeutically relevant glycoproteins, including antibodies, is relegated to mammalian cells. However, mammalian cell culture suffers from a number of drawbacks including: (i) extremely high manufacturing costs and low volumetric productivity of eukaryotic hosts, such as CHO cells, relative to bacteria; (ii) retroviral contamination; (iii) the relatively long time required to generate stable cell lines; (iv) relative inability to rapidly generate stable, "high-producing" eukaryotic cell lines via genetic modification; and (v) high product variability created by glycoform heterogeneity that arises when using host cells, such as CHO, that have endogenous non-human glycosylation pathways (Choi et al., "Use of Combinatorial Genetic Libraries to Humanize N-linked Glycosylation in the Yeast *Pichia pastoris*," *Proc Natl Acad Sci USA* 100:5022-7 (2003)). Expression in *E. coli*, on the other hand, does not suffer from these limitations.

Expression of a Glycosylated Therapeutic Proteins in *E. coli*

Many therapeutic recombinant proteins are currently expressed using *E. coli* as a host organism. One of the best examples is human insulin, which was first produced in *E. coli* by Eli Lilly in 1982. Since that time, a vast number of human therapeutic proteins have been approved in the U.S. and Europe that rely on *E. coli* expression, including human growth hormone (hGH), granulocyte macrophage colony stimulating factor (GM-CSF), insulin-like growth factor (IGF-1, IGFBP-3), keratinocyte growth factor, interferons (IFN-α, IFN-β1b, IFN-γ1b), interleukins (IL-1, IL-2, IL-11), tissue necrosis factor (TNF-α), and tissue plasminogen activator (tPA). However, almost all glycoproteins are produced in mammalian cells. When a protein that is normally glycosylated is expressed in *E. coli*, the lack of glycosylation in that host can yield proteins with impaired function. For instance, aglycosylated human monoclonal antibodies (mAbs) (e.g., anti-tissue factor IgG1) can be expressed in soluble form and at high levels in *E. coli* (Simmons et al., "Expression of Full-length Immunoglobulins in *Escherichia coli*: Rapid and Efficient Production of Aglycosylated Antibodies," *J Immunol Methods* 263:133-47 (2002)). However, while *E. coli*-derived mAbs retained tight binding to their cognate antigen and neonatal receptor and exhibited a circulating half-life comparable to mammalian cell-derived antibodies, they were incapable of binding to C1q and the FcγRI receptor due to the absence of N-glycan.

Eukaryotic and Prokaryotic N-Linked Protein Glycosylation

N-linked protein glycosylation is an essential and conserved process occurring in the endoplasmic reticulum (ER) of eukaryotic organisms (Burda et al., "The Dolichol Pathway of N-linked Glycosylation," *Biochim Biophys Acta* 1426:239-57 (1999)). It is important for protein folding, oligomerization, quality control, sorting, and transport of secretory and membrane proteins (Helenius et al., "Intracellular Functions of N-linked Glycans," *Science* 291:2364-9 (2001)). The eukaryotic N-linked protein glycosylation pathway (FIG. 1) can be divided into two different processes: (i) the assembly of the lipid-linked oligosaccharide at the membrane of the endoplasmic reticulum and (ii) the transfer of the oligosaccharide from the lipid anchor dolichyl pyrophosphate to selected asparagine residues of nascent polypeptides. The characteristics of N-linked protein glycosylation, namely (i) the use of dolichyl pyrophosphate (Dol-PP) as carrier for oligosaccharide assembly, (ii) the transfer of only the completely assembled $Glc_3Man_9GlcNAc_2$ oligosaccharide, and (iii) the recognition of asparagine residues characterized by the sequence N-X-S/T where N is asparagine, X is any amino acid except proline, and S/T is serine/threonine (Gavel et al., "Sequence Differences Between Glycosylated and Non-glycosylated Asn-X-Thr/Ser Acceptor Sites: Implications for Protein Engineering," *Protein Eng* 3:433-42 (1990)) are highly conserved in eukaryotes. The oligosaccharyltransferase (OST) catalyzes the transfer of the oligosaccharide from the lipid donor dolichylpyrophosphate to the acceptor protein. In yeast, eight different membrane proteins have been identified that constitute the complex in vivo (Kelleher et al., "An Evolving View of the Eukaryotic Oligosaccharyltransferase," *Glycobiology* 16:47 R-62R (2006)). STT3 is thought to represent the catalytic subunit of the OST (Nilsson et al., "Photocross-linking of Nascent Chains to the STT3 Subunit of the Oligosaccharyltransferase Complex," *J Cell Biol* 161:715-25 (2003) and Yan et al., "Studies on the Function of Oligosaccharyl Transferase Subunits. Stt3p is Directly Involved in the Glycosylation Process," *J Biol Chem* 277: 47692-700 (2002)). It is the most conserved subunit in the OST complex (Burda et al., "The Dolichol Pathway of N-linked Glycosylation," *Biochim Biophys Acta* 1426:239-57 (1999)).

Conversely, the lack of glycosylation pathways in bacteria has greatly restricted the utility of prokaryotic expression hosts for making therapeutic proteins, especially since by certain estimates "more than half of all proteins in nature will eventually be found to be glycoproteins" (Apweiler et al., "On the Frequency of Protein Glycosylation, as Deduced From Analysis of the SWISS-PROT Database," *Biochim Biophys Acta* 1473:4-8 (1999)). Recently, however, it was discovered that the genome of a pathogenic bacterium, *C. jejuni*, encodes a pathway for N-linked protein glycosylation (Szymanski et al., "Protein Glycosylation in Bacterial Mucosal Pathogens," *Nat Rev Microbiol* 3:225-37 (2005)). The genes for this pathway, first identified in 1999 by Szymanski and coworkers (Szymanski et al., "Evidence for a System of General Protein Glycosylation in *Campylobacter jejuni*," *Mol Microbiol* 32:1022-30 (1999)), comprise a 17-kb locus named pgl for protein glycosylation. Following discovery of the pgl locus, in 2002 Linton et al. identified two *C. jejuni* glycoproteins, PEB3 and CgpA, and showed that *C. jejuni*-derived glycoproteins such as these bind to the N-acetyl galactosamine (GalNAc)-specific lectin soybean agglutinin (SBA) (Linton et al., "Identification of N-acetylgalactosamine-containing Glycoproteins PEB3 and CgpA in *Campylobacter jejuni*," *Mol Microbiol* 43:497-508 (2002)). Shortly thereafter, Young et al. identified more than 30 potential *C. jejuni* glycoproteins, including PEB3 and CgbA, and used mass spectrometry and NMR to reveal that the N-linked glycan was a heptasaccharide with the structure GalNAc-$\alpha$-1,4-GalNAc-$\alpha$-1,4-[Glc$\beta$1,3]GalNAc-$\alpha$1,4-GalNAc-$\alpha$-1,4-GalNAc-$\alpha$1,3-Bac-$\beta$1,N-Asn (GalNAc$_5$GlcBac, where Bac is bacillosamine or 2,4-diacetamido-2,4,6-trideoxyglucose) (Young et al., "Structure of the N-linked Glycan Present on Multiple Glycoproteins in the Gram-negative Bacterium, *Campylobacter jejuni*," *J Biol Chem* 277:42530-9 (2002)) (FIG. 2). The branched heptasaccharide is synthesized by sequential addition of nucleotide-activated sugars on a lipid carrier undecaprenylpyrophosphate on the cytoplasmic side of the inner membrane (Feldman et al., "Engineering N-linked Protein Glycosylation with Diverse O Antigen Lipopolysaccharide Structures in *Escherichia coli*," *Proc Natl Acad Sci USA* 102:3016-21 (2005)) and, once assembled, is flipped across the membrane by the putative ATP-binding cassette (ABC) transporter WlaB (Alaimo et al., "Two Distinct But Interchangeable Mechanisms for Flipping of Lipid-linked Oligosaccharides," *Embo J* 25:967-76 (2006) and Kelly et al., "Biosynthesis of the N-linked Glycan in *Campylobacter jejuni* and Addition Onto Protein Through Block Transfer," *J Bacteriol* 188:2427-34 (2006)). Next, transfer of the heptasaccharide to substrate proteins in the periplasm is catalyzed by an OST named PglB, a single, integral membrane protein with significant sequence similarity to the catalytic subunit of the eukaryotic OST STT3 (Young et al., "Structure of the N-linked Glycan Present on Multiple Glycoproteins in the Gram-negative Bacterium, *Campylobacter jejuni*," *J Biol Chem* 277:42530-9 (2002)). PglB attaches the heptasaccharide to asparagine in the motif D/E-$X_3$-N-$X_2$-S/T (where D/E is aspartic acid/glutamic acid, $X_1$ and $X_2$ are any amino acids except proline, N is asparagine, and S/T is serine/threonine), a sequon similar to that used in the eukaryotic glycosylation process (N-X-S/T) (Kowarik et al., "Definition of the Bacterial N-glycosylation Site Consensus Sequence," *Embo J* 25:1957-66 (2006)).

Glycoengineering of Microorganisms

A major problem encountered when expressing therapeutic glycoproteins in mammalian, yeast, or even bacterial host cells is the addition of non-human glycans. For instance, yeast, one of the two most frequently used systems for the production of therapeutic glycoproteins, transfer highly immunogenic mannan-type N-glycans (containing up to one hundred mannose residues) to recombinant glycoproteins. Mammalian expression systems can also modify therapeutic proteins with non-human sugar residues, such as the N-glycosylneuraminic acid (Neu5Gc) form of sialic acid (produced in CHO cells and in milk) or the terminal $\alpha$(1,3)-galactose (Gal) (produced in murine cells). Repeated administration of therapeutic proteins carrying non-human sugars can elicit adverse reactions, including an immune response in humans.

As an alternative to using native glycosylation systems for producing therapeutic glycoproteins, the availability of glyco-engineered expression systems could open the door to customizing the glycosylation of a therapeutic protein and could lead to the development of improved therapeutic glycoproteins. Such a system would have the potential to eliminate undesirable glycans and perform human glycosylation to a high degree of homogeneity. To date, only the yeast *Pichia pastoris* has been glyco-engineered to provide an expression system with the capacity to control and optimize glycosylation for specific therapeutic functions (Gerngross, T. U., "Advances in the Production of Human Therapeutic Proteins in Yeasts and Filamentous fungi," *Nat Biotechnol* 22:1409-14 (2004); Hamilton et al., "Glycosylation Engineering in Yeast: The Advent of Fully Humanized Yeast," *Curr Opin Biotechnol* 18:387-92 (2007); and Wildt et al., "The Humanization of N-glycosylation Pathways in Yeast," *Nat Rev Microbiol* 3:119-28 (2005)).

For example, a panel of glyco-engineered *P. pastoris* strains was used to produce various glycoforms of the monoclonal antibody Rituxan (an anti-CD20 IgG1 antibody) (Li et al., "Optimization of Humanized IgGs in Glycoengineered *Pichia pastoris*," *Nat Biotechnol* 24:210-5 (2006)). Although these antibodies share identical amino acid sequences to commercial Rituxan, specific glycoforms displayed ~100-fold higher binding affinity to relevant Fc$\gamma$RIII receptors and exhibited improved in vitro human B-cell depletion (Li et al., "Optimization of Humanized IgGs in Glycoengineered *Pichia pastoris*," *Nat Biotechnol* 24:210-5 (2006)). The tremendous success and potential of glyco-engineered *P. pastoris* is not without some drawbacks. For instance, in yeast and all other eukaryotes N-linked glycosylation is essential for viability (Herscovics et al., "Glycoprotein Biosynthesis in Yeast," *FASEB J* 7:540-50 (1993) and Zufferey et al., "STT3, a Highly Conserved Protein Required for Yeast Oligosaccharyl Transferase Activity In Vivo," *EMBO J* 14:4949-60 (1995)). Thus, the systematic elimination and re-engineering by Gerngross and coworkers of many of the unwanted yeast N-glycosylation reactions (Choi et al., "Use of Combinatorial Genetic Libraries to Humanize N-linked Glycosylation in the Yeast *Pichia pastoris*," *Proc Natl Acad Sci USA* 100:5022-7 (2003)) has resulted in strains that are "sick" compared to their wild-type progenitor. This can be worsened during high-level glycoprotein expression due to the large metabolic burden placed on the yeast glycosylation system. As a result, the cell yield that can be obtained during large-scale fermentation is limited. Furthermore, elimination of the mannan-type N-glycans is only half of the glycosylation story in yeast. This is because yeast also perform O-linked glycosylation whereby O-glycans are linked to Ser or Thr residues in glycoproteins (Gentzsch et al., "The PMT Gene Family: Protein O-glycosylation in *Saccharomyces cerevisiae* is Vital," *EMBO J* 15:5752-9 (1996)). As with N-linked glycosylation, O-glycosylation is essential for viability (Gentzsch et al., "The PMT Gene Family: Protein O-glycosylation in *Saccharomyces cerevisiae* is Vital," *EMBO* 115:5752-9 (1996)) and thus cannot be genetically deleted from glyco-engineered yeast. Since there are differences between the O-glycosylation machinery of yeast and humans, the possible addition of O-glycans by glyco-engineered yeast strains has the potential to provoke adverse reactions including an immune response.

Recently, Aebi and his coworkers transferred the *C. jejuni* glycosylation locus into *E. coli* and conferred upon these cells the extraordinary ability to post-translationally modify proteins with N-glycans (Wacker et al., "N-linked Glycosylation in *Campylobacter jejuni* and its Functional Transfer into *E. coli*," *Science* 298:1790-3 (2002)). However, despite the functional similarity shared by the prokaryotic and eukaryotic glycosylation mechanisms, the oligosaccharide chain attached by the prokaryotic glycosylation machinery (GalNAc$_5$GlcBac) is structurally distinct from that attached by eukaryotic glycosylation pathways (Szymanski et al., "Protein Glycosylation in Bacterial Mucosal Pathogens," *Nat Rev Microbiol* 3:225-37 (2005); Young et al., "Structure of the N-linked Glycan Present on Multiple Glycoproteins in the Gram-negative Bacterium, *Campylobacter jejuni*," *J Biol Chem* 277:42530-9 (2002); and Weerapana et al., "Asparagine-linked Protein Glycosylation: From Eukaryotic to Prokaryotic Systems," *Glycobiology* 16:91 R-101R (2006)). Numerous attempts (without success) have been made to reprogram *E. coli* with a eukaryotic N-glycosylation pathway to express N-linked glycoproteins with structurally homogeneous human-like glycans.

The present invention is directed to overcoming the deficiencies in the art.

SUMMARY OF THE INVENTION

A first aspect of the present invention relates to a prokaryotic host cell comprising eukaryotic glycosyltransferase activity, where the eukaryotic glycosyltransferase activity is eukaryotic dolichyl-linked UDP-GlcNAc transferase activity and eukaryotic mannosyltransferase activity.

One aspect of the present invention is directed to a glycoprotein conjugate comprising a protein and at least one peptide comprising a D-X$_1$-N-X$_2$-T (SEQ ID NO: 17) motif fused to the protein, where D is aspartic acid, X$_1$ and X$_2$ are any amino acid other than proline, N is asparagine, and T is threonine.

Another aspect of the present invention is directed to a method of producing a glycosylated protein. This method comprises providing a prokaryotic host cell comprising eukaryotic glycosyltransferase activity, where the eukaryotic glycosyltransferase activity is eukaryotic dolichyl-linked UDP-GlcNAc transferase activity and eukaryotic mannosyltransferase activity. The prokaryotic host cell is then cultured under conditions effective to produce a glycosylated protein.

A further aspect of the present invention pertains to a method for screening bacteria or bacteriophages. This method involves expressing one or more glycans on the surface of a bacteria and attaching a label on the one or more glycans on the surface of the bacteria or on the surface of a bacteriophage derived from the bacteria. The label is then analyzed in a high-throughput format.

Another aspect of the present invention relates to a glycosylated antibody comprising an Fv portion which recognizes and binds to a native antigen and an Fc portion which is glycosylated at a conserved asparagine residue.

One aspect of the present invention relates to a reprogrammed prokaryotic host with a N-glycosylation pathway to express N-linked glycoproteins with structurally homogeneous human-like glycans. Prokaryotic host cells can comprise glycosyltransferase activities in the form of a dolichyl-linked UDP-GlcNAc transferase and a mannosyltransferase. In some embodiments, the UDP-GlcNAc transferase comprises alg13 and alg14 gene activity. In other embodiments, the mannosyltransferase comprise alg1 and alg2 gene activity. In additional embodiments, the prokaryotic host cell comprises a flippase activity including pglK and rft1. In further embodiments, the prokaryotic host cell comprises at least one oligosaccharyl transferase activity, such as pglB and STT3.

In preferred aspects, the present invention commercializes technologies for the design, discovery, and development of glycoprotein diagnostics and therapeutics. Specifically, the present invention provides for the development of a low-cost strategy for efficient production of authentic human glycoproteins in microbial cells with the potential to revolutionize the enterprise surrounding the manufacturing of therapeutic proteins. In various aspects, the glyco-engineered bacteria of the invention are capable of stereospecific production of N-linked glycoproteins. In one embodiment, bacteria have been genetically engineered with a collection of genes encoding a novel glycosylation pathway that is capable of efficiently glycosylating target proteins at specific asparagine acceptor sites (e.g., N-linked glycosylation). Using these specially engineered cell lines, virtually any recombinant protein-of-interest can be expressed and glycosylated, thus, production of numerous authentic human glycoproteins is possible.

Further, the invention provides proprietary platform technologies for engineering permutations of sugar structures, thereby enabling for the first time "bacterial glycoprotein engineering." One expectation of glycoengineering—the intentional manipulation of protein-associated carbohydrates to alter pharmacokinetic properties of proteins—is to elucidate the role of glycosylation in biological phenomena. Accordingly, in various aspects, the invention provides biotechnological synthesis of novel glycoconjugates and immunostimulating agents for research, industrial, and therapeutic applications.

The major advantage of *E. coli* as a host for glycoprotein expression is that, unlike yeast and all other eukaryotes, there are no native glycosylation systems. Thus, the addition (or subsequent removal) of glycosylation-related genes should have little to no bearing on the viability of glyco-engineered *E. coli* cells. Furthermore, the potential for non-human glycan attachment to target proteins by endogenous glycosylation reactions is eliminated in these cells.

Accordingly, in various embodiments, an alternative for glycoprotein expression is disclosed where a prokaryotic host cell is used to produce N-linked glycoproteins, which provides an attractive solution for circumventing the significant hurdles associated with eukaryotic cell culture. The use of bacteria as a production vehicle is expected to yield structurally homogeneous human-like N-glycans while at the same time dramatically lowering the cost and time associated with protein drug development and manufacturing.

Other key advantages include: (i) the massive volume of data surrounding the genetic manipulation of bacteria; (ii) the established track record of using bacteria for protein production—30% of protein therapeutics approved by the FDA since 2003 are produced in *E. coli* bacteria; and (iii) the existing infrastructure within numerous companies for bacterial production of protein drugs.

In comparison to various eukaryotic protein expression systems, the process employed using the methods and composition of the invention provides a scalable, cost-effective, optimal recombinant glycoprotein expression, free of human pathogens, free of immunogenic N- and O-linked glycosylation reactions, capable of rapid cloning and fast growth rate, fast doubling time (~20 minutes), high growth (high OD), high titer and protein yields (in the range of 50% of the total soluble protein (TSP)), ease of product purification from the periplasm or supernatant, genetically tractable, thoroughly studied, compatible with the extensive collection of expression optimization methods (e.g., promoter engineering, mRNA stabilization methods, chaperone co-expression, protease depletion, etc.).

BRIEF DESCRIPTION OF THE DRAWINGS

FIG. 4A shows a peptide glycosylation tag (SEQ ID NO: 16). FIG. 4B shows an anti-His Western blot of (left-to-right) MBP with a C-terminal GlycTag (GT), the *C. jejuni* glycoprotein cjAcrA, MBP with an N-terminal GT, MBP C-terminal GT without a secretion signal peptide, and MBP & GFP each with a C-terminal GT and a Tat-specific (ssTorA) signal peptide. Proteins were Ni-purified from glyco-engineered *E. coli* (pgl+, except lane 2) and immunoblotted with anti-HIS serum. FIG. 4C shows a Western blot against the bacterial heptasaccharide using anti-Hept serum. FIG. 4D shows at least three discrete bands characteristic of multiple N-glycans for MBP C-terminal GT (left) and MBP N-terminal GT (right).

FIG. 5A shows the glycosylation at Asn297 in $C_H2$ results in a conformational shift in the Fc region of the IgG that endows binding to the appropriate receptor molecules to elicit effector function. Western blot analysis of IgG M18.1 purified from pgl– (FIG. 5B) and pgl+ (FIG. 5C) *E. coli* using Protein-A-G resin columns (Pierce). Samples were run in non-reducing 12% SDS gels and immunoblotted with anti-human IgG and hR6P antiserum.

FIG. 10A shows the evolutionary trajectory from bacterial to mammalian glycoforms. FIG. 10B shows the pathway for biosynthesis and transfer of $Man_3GlcNAc_2$ core glycoform to bacterial substrate proteins.

FIG. 11A shows a Western blot analysis of the soluble cytoplasmic fraction from wt *E. coli* cells probed with anti-his antibody to detect Alg13-his. FIG. 11B shows a Western blot analysis of different fractions isolated from wt and ΔdnaJ cells probed with anti-FLAG antibody to detect Alg14-FLAG. Samples were collected at 0, 1, 2, and 3 hours post induction (hpi) for Alg13 and at 3 hpi for Alg14. Samples were prepared by centrifugation of lysed cells at 20,000×g for 20 min and collecting the supernatant as the soluble fraction and the pellet as the insoluble fraction (insol). For Alg14, the soluble fraction was further spun at 100,000×g for 1 hr and the supernatant and pellet were collected as the soluble (sol) and membrane (mem) fractions, respectively.

Figure 13:
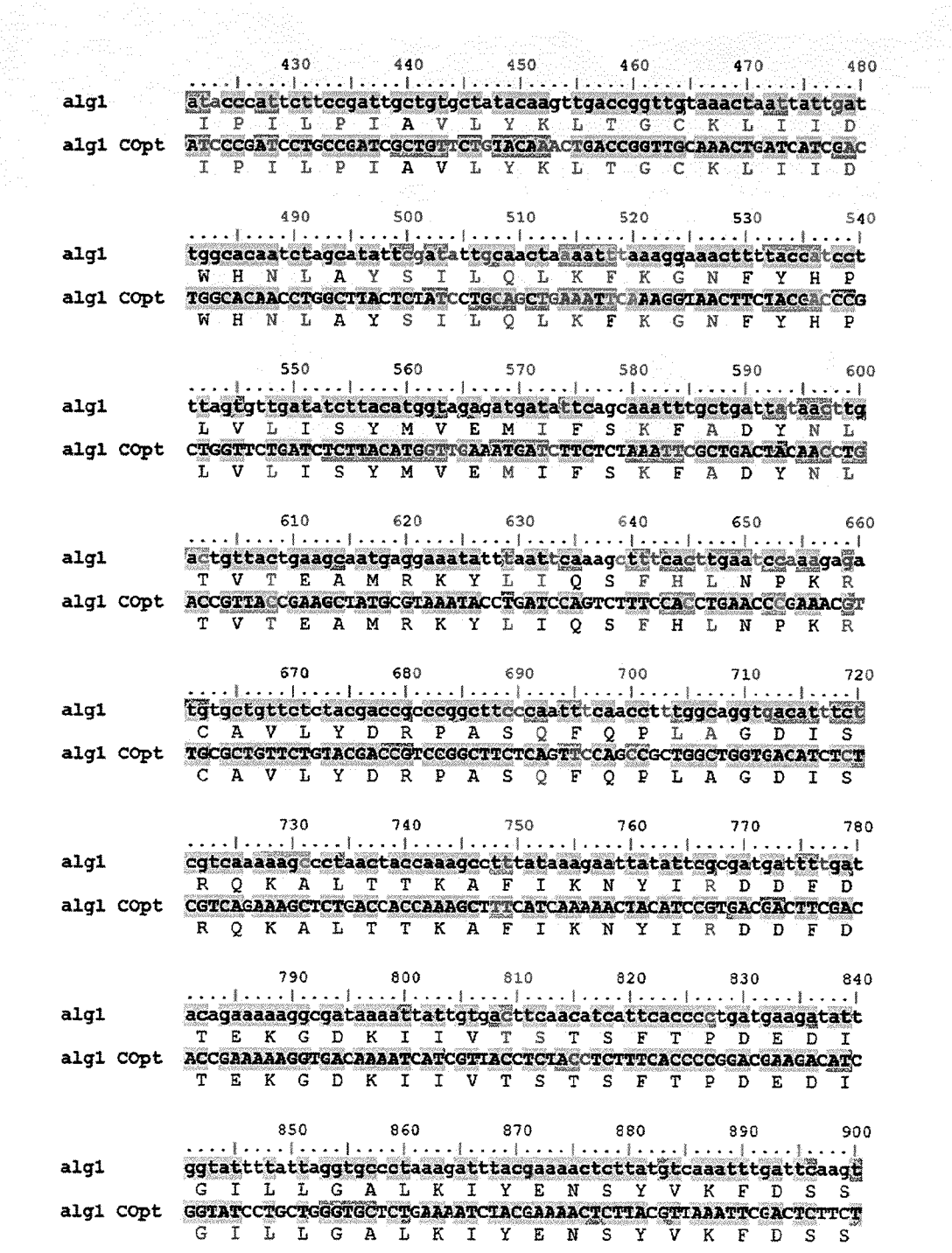

FIG. 13 is an alignment between the wild-type (SEQ ID NO: 5) and codon optimized (SEQ ID NO: 6) nucleotide sequences for Alg1. The corresponding amino acid sequence of Alg1 (SEQ ID NO: 19) is shown above the alignment.

FIG. 14 is an alignment between the wild-type (SEQ ID NO: 7) and codon optimized (SEQ ID NO: 8) nucleotide sequences for Alg2. The corresponding amino acid sequence of Alg2 (SEQ ID NO: 20) is shown above the alignment.

FIG. 15 is an alignment between the wild-type (SEQ ID NO: 1) and codon optimized (SEQ ID NO: 2) nucleotide sequences for Alg13. The corresponding amino acid sequence of Alg13 (SEQ ID NO: 21) is shown above the alignment.

FIG. 16 is an alignment between the wild-type (SEQ ID NO: 3) and codon optimized (SEQ ID NO: 4) nucleotide sequences for Alg14. The corresponding amino acid sequence of Alg14 (SEQ ID NO: 22) is shown above the alignment FIG. 17 is an alignment between the wild-type (SEQ ID NO: 9) and codon optimized (SEQ ID NO: 10) nucleotide sequences for Rft1. The corresponding amino acid sequence of Rft1 (SEQ ID NO: 23) is shown above the alignment.

Figure 18:
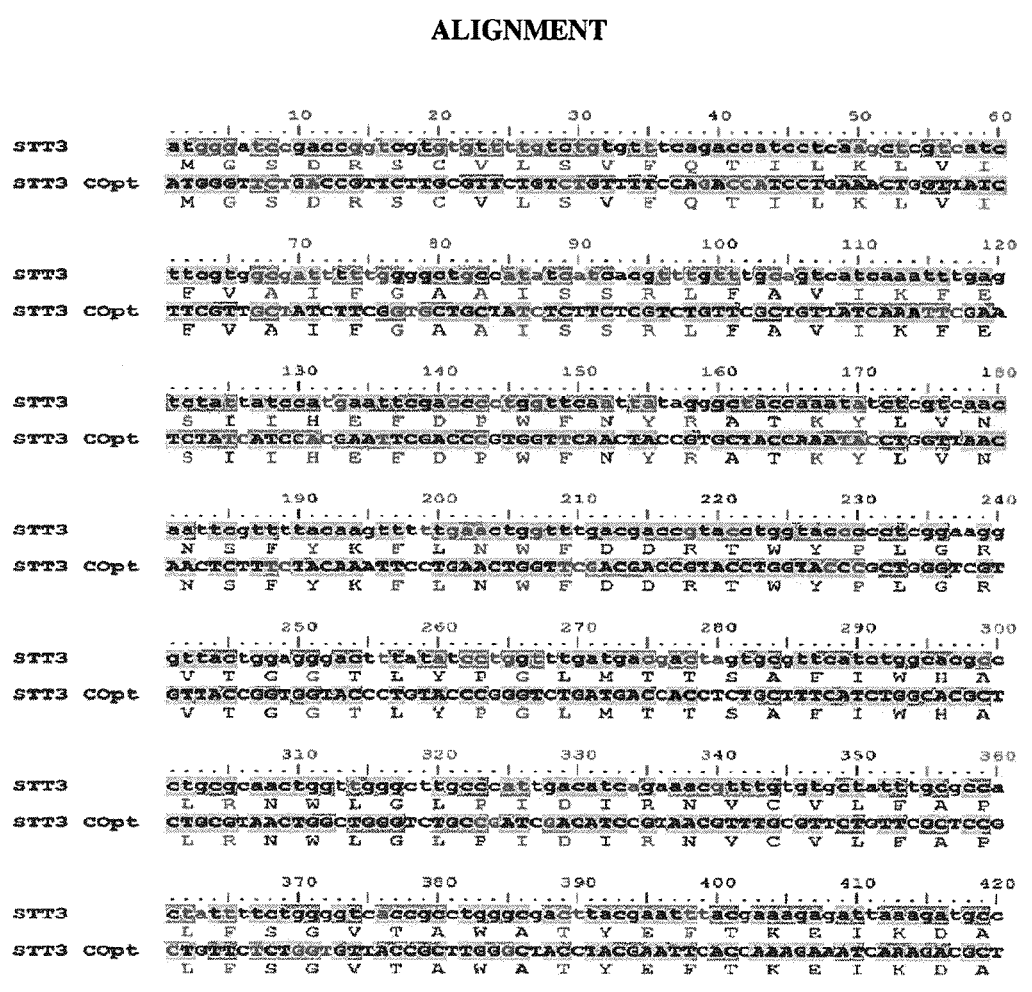
Figure 18:
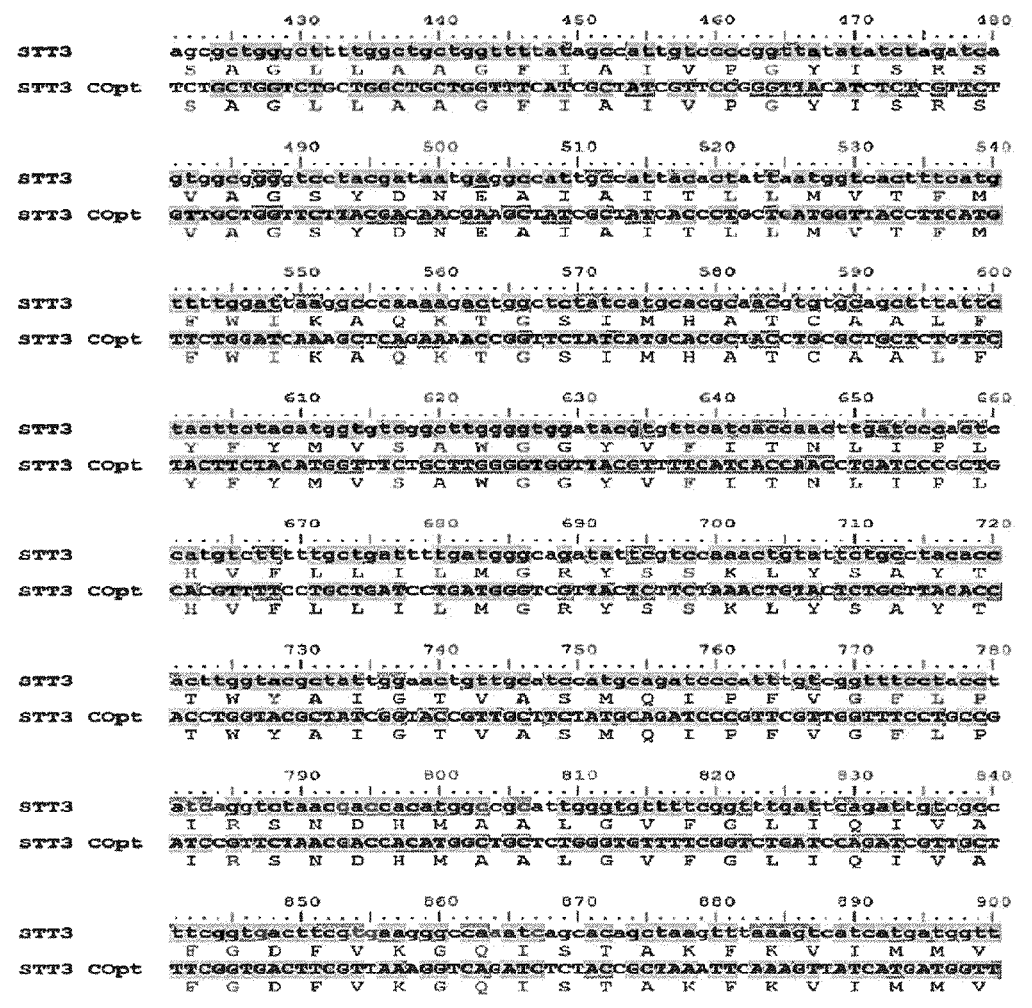
Figure 18:
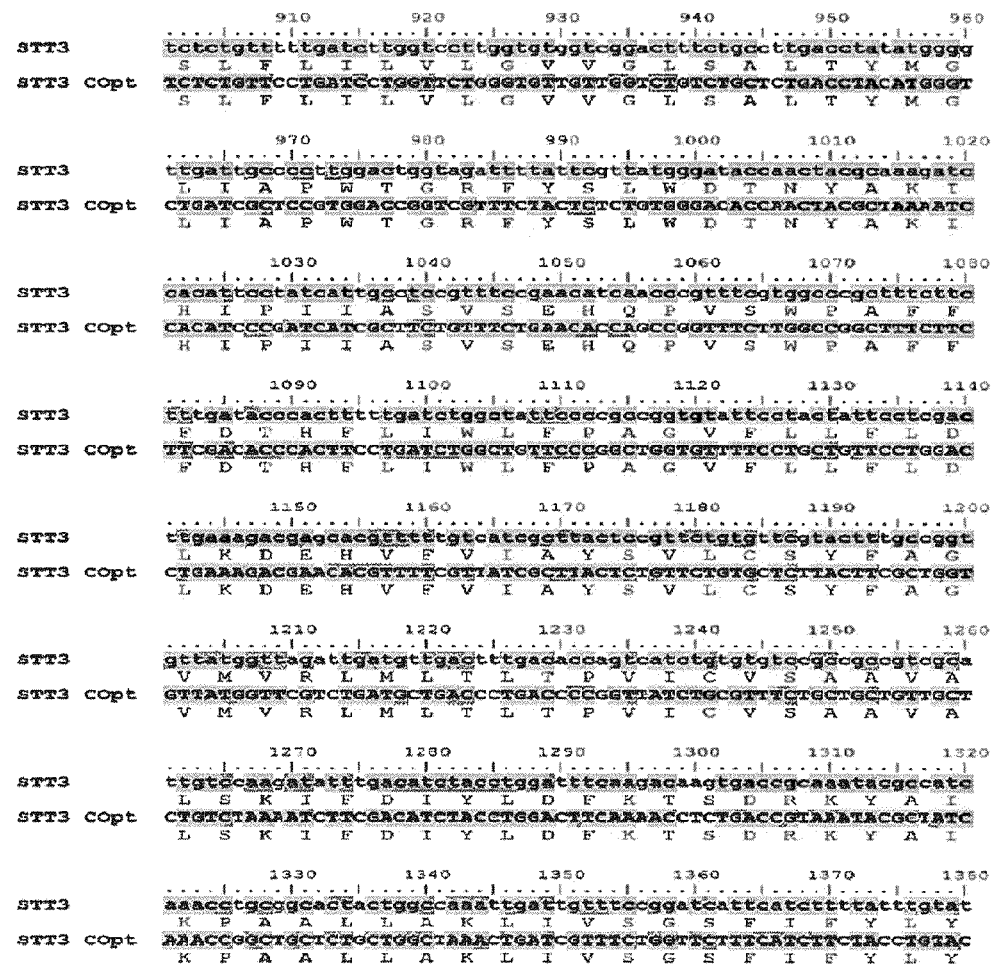
Figure 18:
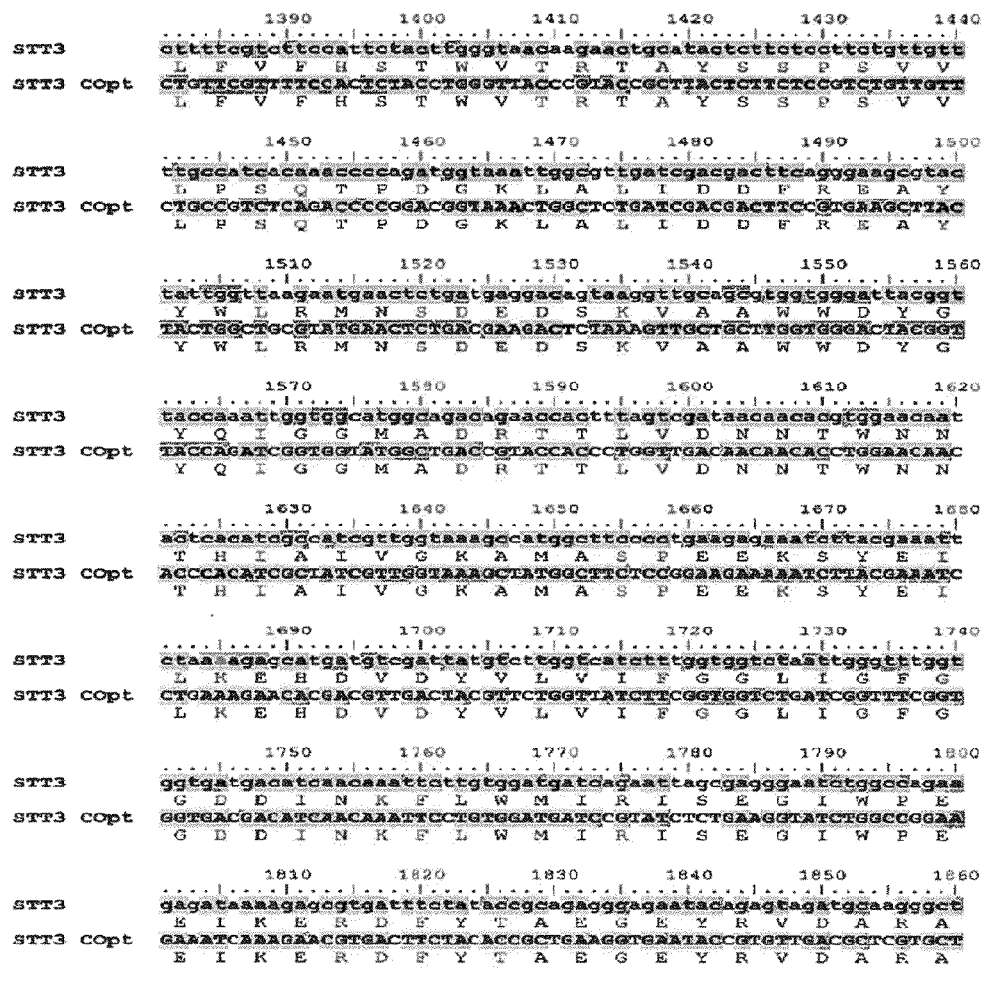
Figure 18:
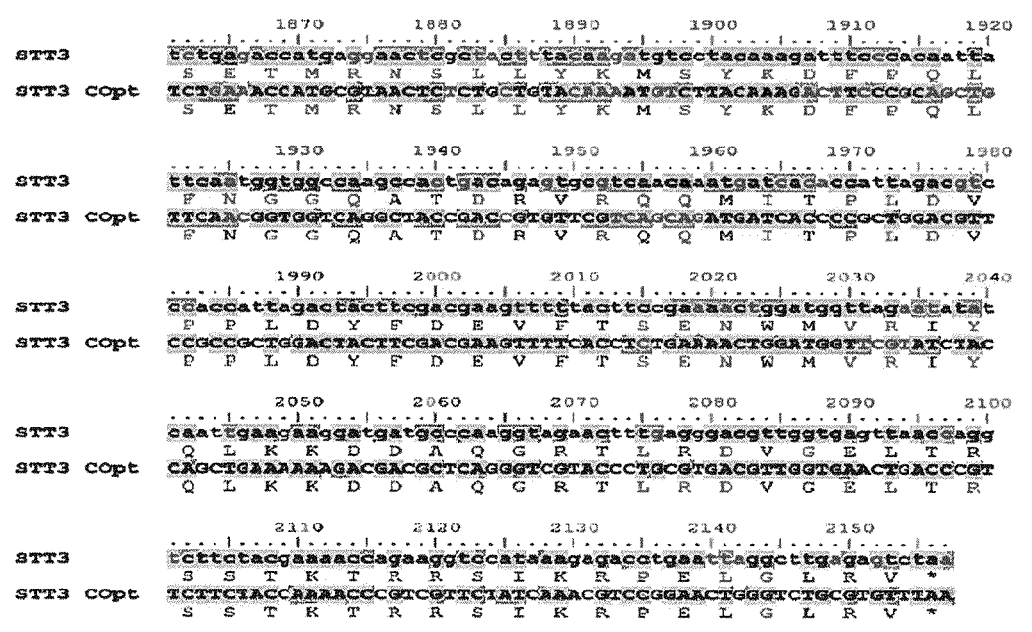

FIG. 18 is an alignment between the wild-type (SEQ ID NO: 11) and codon optimized (SEQ ID NO: 12) nucleotide sequences for Sttc3. The corresponding amino acid sequence of Sttc3 (SEQ ID NO: 24) is shown above the alignment.

DETAILED DESCRIPTION OF THE INVENTION

Definitions

Figure 1:
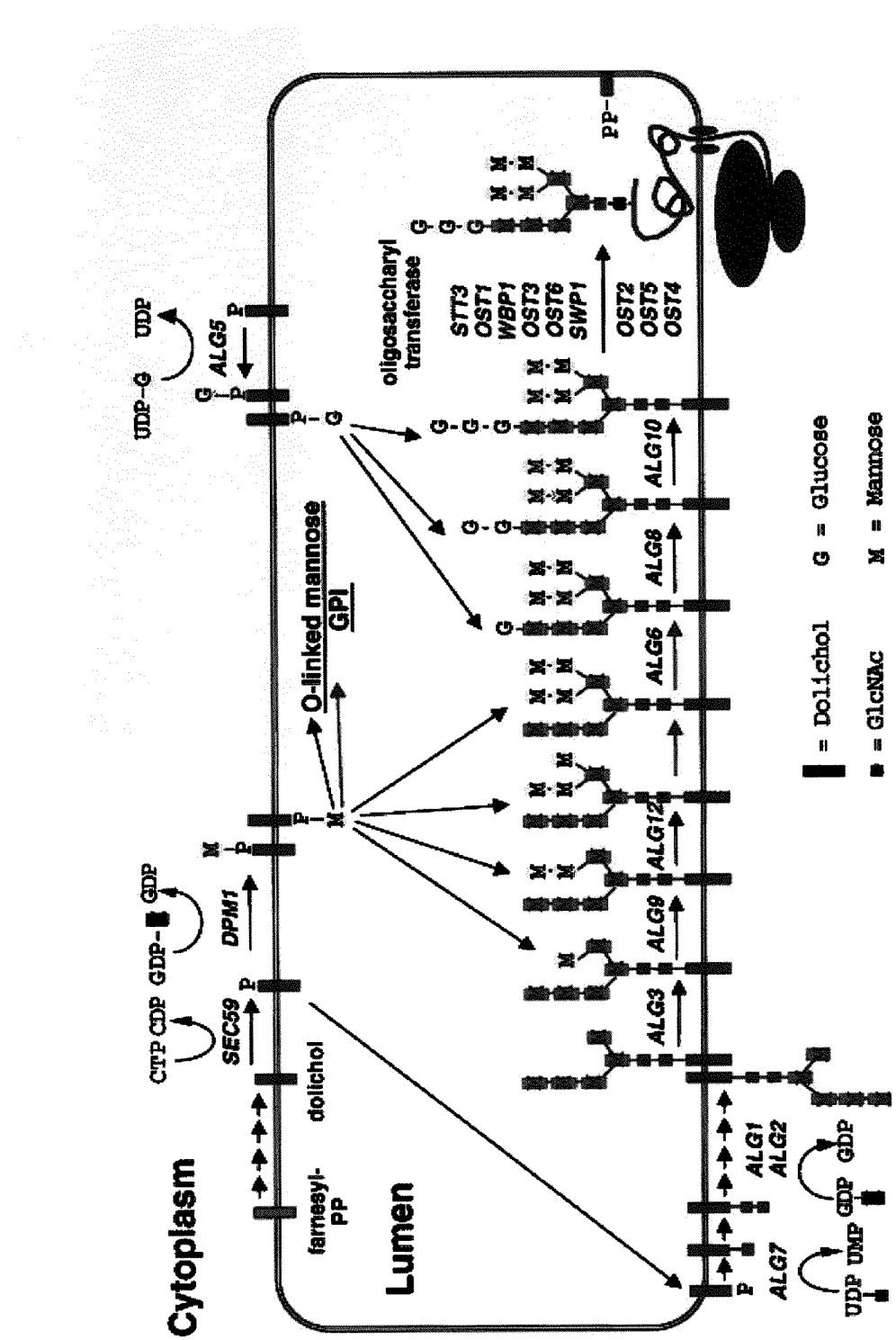
FIG. 1 illustrates a biosynthetic scheme of the lipid-linked oligosaccharide and the transfer to protein at the membrane of the endoplasmic reticulum in *S. cerevisiae*. The loci required for the individual reactions are indicated. The origin of the mannose residues either from GDP-mannose directly (light shading) or from dolichylphosphomannose (dark shading) is indicated. See Burda et al., "The Dolichol Pathway of N-linked Glycosylation," *Biochim Biophys Acta* 1426:239-57 (1999), which is hereby incorporated by reference in its entirety.
Figure 2:
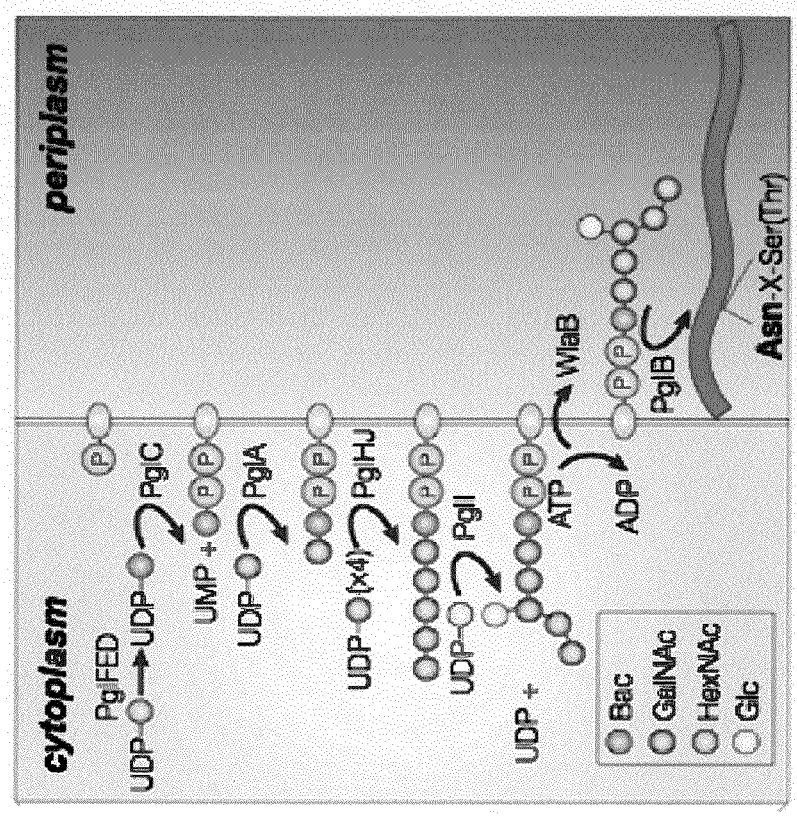
FIG. 2 illustrates the biosynthesis science of N-linked glycoproteins in bacteria. In *C. jejuni*, N-linked glycosylation proceeds through the sequential addition of nucleotide-activated sugars onto a lipid carrier, resulting in the formation of a branched heptasaccharide. This glycan is then flipped across the inner membrane by PglK (formerly WlaB) and the OTase PglB then catalyzes the transfer of the glycan to an asparagine side chain. Bac is 2,4-diacetamido-2,4,6-trideoxyglucose; GalNAc is N-acetylgalactosamine; HexNAc is N-acetylhexosamine; Glc is glucose. See Szymanski et al., "Protein Glycosylation in Bacterial Mucosal Pathogens," *Nat Rev Microbiol* 3:225-37 (2005), which is hereby incorporated by reference in its entirety.

The following definitions of terms and methods are provided to better describe the present disclosure and to guide those of ordinary skill in the art in the practice of the present disclosure.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

As used herein, "comprising" means "including" and the singular forms "a" or "an" or "the" include plural references unless the context clearly dictates otherwise. For example, reference to "comprising a cell" includes one or a plurality of such cells. The term "or" refers to a single element of stated alternative elements or a combination of two or more elements, unless the context clearly indicates otherwise.

The term "human-like" with respect to a glycoproteins refers to proteins having attached N-acetylglucosamine (GlcNAc) residue linked to the amide nitrogen of an asparagine residue (N-linked) in the protein, that is similar or even identical to those produced in humans.

"N-glycans" or "N-linked glycans" refer to N-linked oligosaccharide structures. The N-glycans can be attached to proteins or synthetic glycoprotein intermediates, which can be manipulated further in vitro or in vivo. The predominant sugars found on glycoproteins are glucose, galactose, mannose, fucose, N-acetylgalactosamine (GalNAc), N-acetylglucosamine (GlcNAc), and sialic acid (e.g., N-acetylneuraminic acid (NeuAc)).

Unless otherwise indicated, and as an example for all sequences described herein under the general format "SEQ ID NO:", "nucleic acid comprising SEQ ID NO:1" refers to a nucleic acid, at least a portion of which has either (i) the sequence of SEQ ID NO:1, or (ii) a sequence complementary to SEQ ID NO:1. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., RNA, DNA, or a mixed polymer) or glycoprotein is one which is substantially separated from other cellular components that naturally accompany the native polynucleotide in its natural host cell, e.g., ribosomes, polymerases and genomic sequences with which it is naturally associated. The term embraces a nucleic acid, polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid, polynucleotide or glycoprotein so described has itself been physically removed from its native environment. For instance, an endogenous nucleic acid sequence in the genome of an organism is deemed "isolated" if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion, or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material or substantially free of culture medium when produced by recombinant techniques or substantially free of chemical precursors or other chemicals when chemically synthesized.

Glycosylation Engineering

A first aspect of the present invention relates to a prokaryotic host cell comprising eukaryotic glycosyltransferase activity, where the eukaryotic glycosyltransferase activity is eukaryotic dolichyl-linked UDP-GlcNAc transferase activity and eukaryotic mannosyltransferase activity.

Figure 10A:
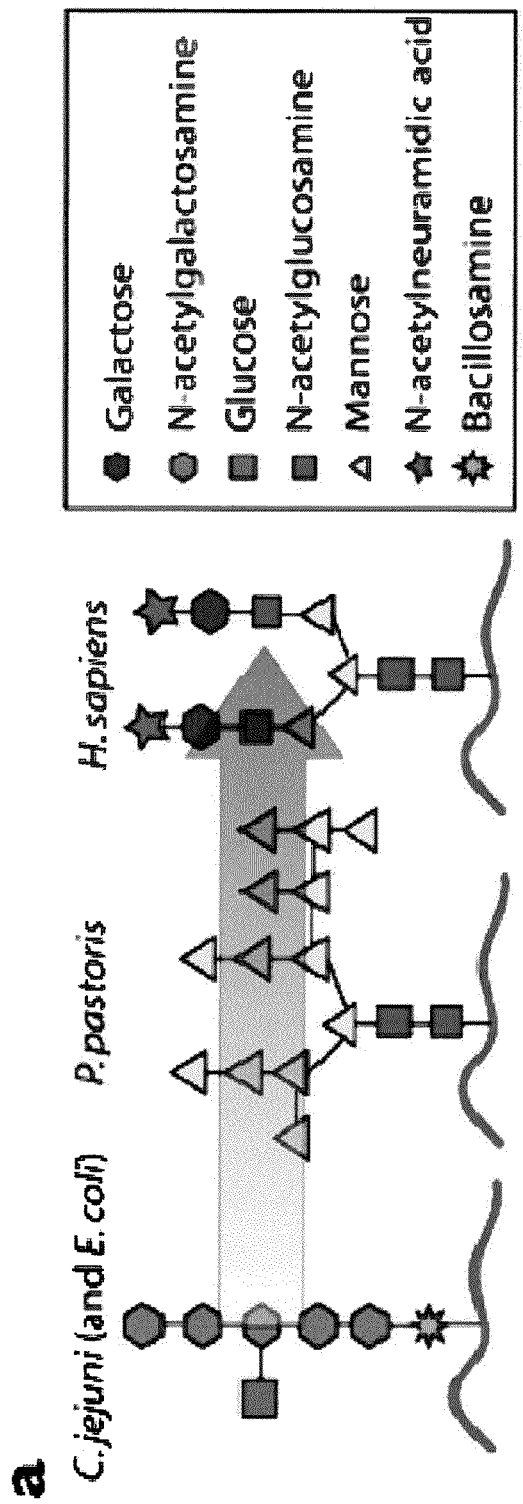
FIGS. 10A-10B are schematic drawings depicting glycan engineering in *E. coli*.
Figure 10B:
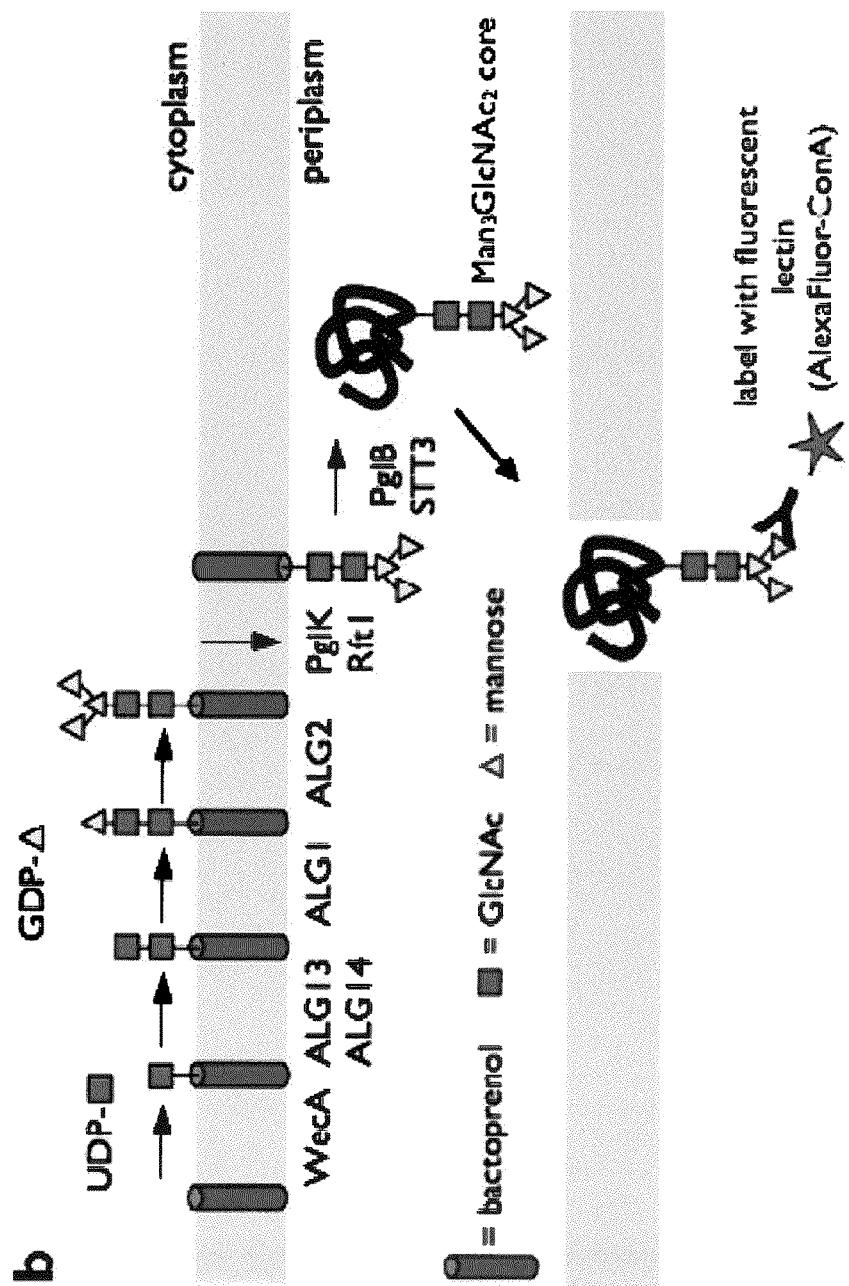

The prokaryotic host cell of the present invention has eukaryotic dolichyl-linked UDP-GlcNAc transferase activity which may comprise Alg13 activity and Alg14 activity. The Alg13 activity and Alg14 activity is achieved with either wild-type nucleotide sequences or codon optimized sequences. As shown in FIG. 10B, these enzymes serve to add GlcNAc unit to bactoprenol. The alg13 wild-type nucleic acid molecule has the nucleotide sequence of SEQ ID NO: 1:

```
atgggtattattgaagaaaaggctcatttgttacgtgtggggcaacgg
tgccataccaaagctcgtctcatgtgtgctaagcgacgaattctgcca
agaattgattcaatatggattcgtacgtctaatcattcagtttgggag
aaactacagttctgaatttgagcatttagtgcaagaacgcgggggcca
aagagaaagccaaaaaattccaattgaccagtttggctgtggcgacac
cgcaagacagtatgtcctgatgaacgggaaattaaaggtgatcgggat
gacttttcgaccaagatgcaaagtattatacgtgattattcagatttg
gtcatatcacacgctggaacgggctctatactagattctctacgttg
aataaaccgttgatagtttgcgtaaacgattattgatggataaccacc
agcagcagatagcagacaagtttgtagagttgggctacgtatggtctt
gtgcacccactgaaacaggtttgatagctggtttacgtgcatctcaaa
cagagaaactcaaaccattcccagtttctcataaccgtcatttgagc
gattgctagttgaaactatatacagctag.
```

The alg13 codon optimized nucleic acid molecule has the nucleotide sequence of SEQ ID NO: 2 as follows:

```
ATGGGTATCATCGAAGAAAAGCTCTGTTCGTTACCTGCGGTGCTACC
GTTCCGTTCCCGAAACTGGTTTCTTGCGTTCTGTCTGACGAATTCTGC
CAGGAACTGATCCAGTACGGTTTCGTTCGTCTGATCATCCAGTTCGGT
CGTAACTACTCTTCTGAATTCGAACACCTGGTTCAGGAACGTGGTGGT
CAGCGTGAATCTCAGAAAATCCCGATCGACCATTCGGTTGCGGTGACA
CCGCTCGTCAGTACGTTCTGATGAACGGTAAACTGAAAGTTATCGGTT
TCGACTTCTCTACCAAAATGCAGTCTATCATCCGTGACTACTCTGACC
TGGTTATCTCTCACGCTGGTACCGGTTCTATCCTGGACTCTCTGCGTC
TGAACAAACCGCTGATCGTTTGCGTTAACGACTCTCTGATGGACAACC
ACCAGCAGCAGATCGCTGACAAATTCGTTGAACTGGGTTACGTTTGGT
CTTGCGCTCCGACCGAAACCGGTCTGATCGCTGGTCTGCGTGCTTCTC
```

AGACCGAAAAACTGAAACCGTTCCCGGTTTCTCACAACCCGTCTTTCG

AACGTCTGCTGGTTGAAACCATCTACTCTTAA

The alg14 wild-type nucleic acid molecule has the nucleotide sequence of SEQ ID NO: 3 as follows:

```
atgaaaacggcctacttggcgtcattggtgctcatcgtatcgacagca
tatgttattaggttgatagcgattctgccttttttccacactcaagca
ggtacagaaaaggatacgaaagatggagttaacctactgaaaatacga
aaatcgtcaaagaaaccgctcaagattttgtattcgtaggatcggga
ggtcatactggtgaaatgatccgtcttctagaaaattaccaggatatt
ttactgggtaagtcgattgtgtacttgggttattctgatgaggcttcc
aggcaaagattcgcccactttataaaaaaatttggtcattgcaaagta
aaatactatgaattcatgaaagctagggaagttaaagcgactctccta
caaagtgtaaagaccatcattggaacgttggtacaatatttgtgcacg
tggttagaatcagatttgctatgtgtggttccctcatctgtttttat
tgaatgggcctggaacatgctgtataatatccattggttgaaaattat
ggaacttatttgcccctgttgggttcctcccatatagtttatgtagaa
tcgctggcaaggattaatactcctagtctgaccggaaaaatattatat
tgggtagtggatgaattcattgtccagtggcaagaattgagggacaat
tatttaccaagatccaagtggttcggcatccttgtttaa
```

The alg14 codon optimized nucleic acid molecule has the nucleotide sequence of SEQ ID NO: 4 as follows:

```
ATGAAAACCGCTTACCTGGCTTCTCTGGTTCTGATCGTTTCTACCGCT
TACGTTATCCGTCTGATCGCTATCCTGCCGTTCTTCCACACCCAGGCT
GGTACCGAAAAAGACACCAAAGACGGTGTTAACCTGCTGAAAATCCGT
AAATCTTCTAAAAAACCGCTGAAAATCTTCGTTTTCCTGGGTTCTGGT
GGTCACACCGGTGAAATGATCCGTCTGCTGGAAAACTACCAGGACCTG
CTGCTGGGTAAATCTATCGTTTACCTGGGTTACTCTGACGAAGCTTCT
CGTCAGCGTTTCGCTCACTTCATCAAAAAATTCGGTCACTGCAAAGTT
AAATACTACGAATTCATGAAAGCTCGTGAAGTTAAAGCTACCCTGCTG
CAGTCTGTTAAAACCATCATCGGTACCCTGGTTCAGTCTTTCGTTCAC
GTTGTTCGTATCCGTTTCGCTATGTGCGGTTCTCCGCACCTGTTCCTG
CTGAACGGTCCGGGTACCTGCTGCATCATCTCTTTCTGGCTGAAAATC
ATGGAACTGCTGCTGCCGCTGCTGGGTTCTTCTCACATCGTTTACGTT
GAATCTCTGGCTCGTATCAACACCCCGTCTCTGACCGGTAAAATCCTG
TACTGGGTTGTTGACGAATTCATCGTTCAGTGGCAGGAACTGCGTGAC
AACTACCTGCCGCGTTCTAAATGGTTCGGTATCCTGGTTTAA.
```

The prokaryotic host cell of present invention has eukaryotic mannosyltransferase activity which comprises Alg1 activity and Alg2 activity. The Alg1 activity and Alg2 activity is achieved with a wild-type nucleic acid molecule or a codon optimized nucleic acid sequence as follows. As shown in FIG. 10B, these enzymes add mannose units to GlcNAc units. The alg1 wild-type nucleic acid molecule has the nucleotide sequence of SEQ ID NO: 5 as follows:

```
atgttttaggaaattcctcggtggttacttgccttaataatattata
cctttccataccgttagtggtttattatgttataccctacttgattat
ggcaacaagtcgaccaaaaaaggatcatcatatttgtgctgggtgat
gtaggacactctccaaggatatgctatcacgctataagtttcagtaag
ttaggttggcaagtcgagctatgcggttatgtggaggacactctaccc
aaaaattatttccagtgatccaaatatcaccgtccatcatatgtcaaa
cttgaaaagaaagggaggcggaacatcagttatatttatggtaaagaa
ggtgcttttcaagttttaagtattttcaaattactttgggaattgag
aggaagcgattacatactagttcaaaatccaccgagcatacccattct
tccgattgctgtgctatacaagttgaccggttgtaaactaattattga
ttggcacaatctagcatattcgatattgcaactaaaatttaaaggaaa
cttttaccatccatagtgttgatatatacatggtagagatgatattca
gcaaatttgctgattataacttgactgttactgaagcaatgaggaaat
ataaattcaaagctttcacttgaatccaaagagatgtgctgttctcta
cgaccgcccggcacccaatttcaacctttggcaggtgacatttctcgt
caaaaagccctaactaccaaagcctttataaagaattatattcgcgat
gattttgatacagaaaaggcgataaaattattgtgacttcaacatca
ttcacccctgatgaagatattggtattttattaggtgccctaaagatt
tacgaaaactatatgtcaaatttgattcaagtttgcctaagatcttgt
gttttataacgggtaaaggaccactaaaggagaaatatatgaagcaag
tagaagaatatgactggaagcgctgtcaaatcgaatttgtgtggttgt
cagcagaggattacccaaagttattacaattatgcgattacggagttt
ccctgcatacttcaagttcagggttggacctgccaatgaaaattttag
atatgtttggctcaggtcttcctgttattgcaatgaactatccagtgc
ttgacgaattagtacaacacaatgtaaatgggttaaaatttgttgata
gaagggagatcatgaatctctgattttgctatgaaagatgctgattt
ataccaaaaattgaagaaaaatgtaagcaggaagctgagaacagatgg
caatcaaatttgggaacgaacaatgagagatagaagcaattcattga.
```

The alg1 codon optimized nucleic acid molecule has the nucleotide sequence of SEQ ID NO: 6 as follows:

```
ATGTTCCTGGAAATCCCGCGITGGCTGCTGGCTCTGATCATCCTGTAC
CTGTCTATCCCGCTGGTTGTTTACTACGTTATCCCGTACCTGTTCTAC
GGTAACAAATCTACCAAAAAACGTATCATCATCTTCGTTCTGGGTGAC
GTTGGTCACTCTCCGCGTATCTGCTACCACGCTATCTCTTTCTCTAAA
CTGGGTTGGCAGGTTGAACTGTGCGGTTACGTTGAAGACACCCTGCCG
AAAATCATCTCTTCTGACCCGAACATCACCGTTCACCACATGTCTAAC
CTGAAACGTAAAGGTGGTGGTACCTCTGTTATCTTCATGGTTAAAAAA
GTTCTGTTCCAGGTTCTGTCTATCTTCAAACTGCTGTGGGAACTGCGT
GGTTCTGACTACATCCTGGTTCAGAACCCGCCGTCTATCCCGATCCTG
CCGATCGCTGTTCTGTACAAACTGACCGGTTGCAAACTGATCATCGAC
TGGCACAACCTGGCTTACTCTATCCTGCAGCTGAAATTCAAAGGTAAC
TTCTACCACCCGCTGGITCTGATCTCTTACATGGTTGAAATGATCTTC
TCTAAATTCGCTGACTACAACCTGACCGTTACCGAAGCTATGCGTAAA
TACCTGATCCAGTCTTTCCACCTGAACCCGAAACGTTGCGCTTTTCTG
TACGACCGTCCGGCTTCTCAGTTCCAGCCGCTGGCTGGTGACATCTCT
CGTCAGAAAGCTCTGACCACCAAAGCTTTCATCAAAAACTACATCCGT
GACGACTTCGACACCGAAAAAGGTGACAAAATCATCGTTACCTCTACC
TCTTTCACCCCGGACGAAGACATCGGTATCCTGCTGGGTGCTCTGAAA
ATCTACGAAAACTCTTACGTTAAATTCGACTCTTCTCTGCCGAAAATC
CTGTGCTTCATCACCGGTAAAGGTCCGCTGAAAGAAAAATACATGAAA
CAGGTTGAAGAATACGACTGGAAACGTTGCCAGATCGAATTCGTTTGG
CTGTCTGCTGAAGACTACCCGAAACTGCTGCAGCTGTGCGACTACGGT
GTTTCTCTGCACACCTCTTCTTCTGGTCTGGACCTGCCGATGAAAATC
CTGGACATGTTCGGTTCTGGTCTGCCGGTTATCGCTATGAACTACCCG
GTTCTGGACGAACTGGTTCAGCACAACGTTAACGGTCTGAAATTCGTT
GACCGTCGTGAACTGCACGAATCTCTGATCTTCGCTATGAAAGACGCT
GACCTGTACCAGAAACTGAAAAAAAACGTTACCCAGGAAGCTGAAAAC
CGTTGGCAGTCTAACTGGGAACGTACCATGCGTGACCTGAAACTGATC
CACTAA.
```

The alg2 wild-type nucleic acid molecule has the nucleotide sequence of SEQ ID NO: 7 as follows:

```
atgattgaaaaggataaaagaacgattgcttttattcatccagaccta
ggtattgggggcgctgaaaggttagtcgtcgatgcagcattaggtcta
cagcaacaaggacatagtgtaatcatctatactagtcactgtgataaa
tcacattgtttcgaagaagttaaaaacggccaattaaaagtcgaagtt
tatggtgatttttaccgacaaacttttggtgtcgtttttttattgtt
ttcgcaacaattagacagctttatttagttattcaattgatcctacag
aaaaaagtgaatgcgtaccaattaattatcattgatcaactgtctaca
tgtattccgcttctgcatatctttagttctgccactttgatgttttat
tgtcatttccccgaccaattattggctcaaagagctgggctattgaag
aaaatatacagactaccatttgacttaatagaacagttttccgtgagt
gctgccgatactgttgtggtaaattcaaatttcactaagaatacgttc
caccaaacgttcaagtatttatccaatgatccagacgtcatttatcca
tgcgtggatttatcaacaatcgaaattgaagatattgacaagaaattt
acaaaacagtgtttaacgaaggcgatagattttacctaagtataaatc
gttttgagaaaaaaaaggatgttgcgctggctataaaggcttttgcgt
tatctgaagatcaaatcaatgacaacgttaagttagttatttgcggtg
gttatgacgagagggttgcagaaaatgtggagtacttgaaggaactac
``` agtctctggccgatgaatacgaattatcccatacaaccatatactacc aagaaataaagcgcgtctccgatttagagtcattcaaaaccaataata gtaaaattatattttaacttccatttcatcatctctgaaagaattac tgctcgaaagaaccgaaatgttattgtatacaccagcatatgagcact ttggtattgttccatagaagccatgaaattaggtaagcctgtactagc agtaaacaatggaggtcctttggagactatcaaatcttacgttgctgg tgaaaatgaaagttctgccactgggtggctaaaacctgccgtccctat tcaatgggctactgcaattgatgaaagcagaaagatcttgcagaacgg ttctgtgaactagagaggaatggcccgctaagagtcaagaaatactat ctagggaagcaatgactcagtcatttgaagaaaacgtcgagaaagtca tatggaaagaaaaaaagtattatcatgggaaatattcggtatttcatt ctctaattttatttttgcatatggcatttataaaaattctacccaataa tccatggcccttcctatttatggcaatttatggtattatattttaag aactacttatggggaatttactgggcatttgtattcgctctctcctac ccttatgaagaaatataa.

The alg2 codon optimized nucleic acid molecule has the nucleotide sequence of SEQ ID NO: 8 as follows:

ATGATCGAAAAAGACAAACGTACCATCGCTTTCATCCACCCGGACCTG

GGTATCGGTGGTGCTGAACGTCTGGTTGTTGACGCTGCTCTGGGTCTG

CAGCAGCAGGGTCACTCTGTTATCATCTACACCTCTCACTGCGACAAA

TCTCACTGCTTCGAAGAAGTTAAAAACGGTCAGCTGAAAGTTGAAGTT

TACGGTGACTTCCTGCCGACCAACTTCCTGGGTCGTTTCTTCATCGTT

TTCGCTACCATCCGTCAGCTGTACCTGGTTATCCAGCTGATCCTGCAG

AAAAAAGTTAACGCTTACCAGCTGATCATCATCGACCAGCTGTCTACC

TGCATCCCGCTGCTGCACATCTTCTCTTCTGCTACCCTGATGTTCTAC

TGCCACTTCCCGGACCAGCTGCTGGCTCAGCGTGCTGGTCTGCTGAAA

AAAATCTACCGTCTGCCGTTCGACCTGATCGAACAGTTCTCTGTTTCT

GCTGCTGACACCTTTTGTTGTTAACTCTAACTTCACCAAAAACACCTT

CCACCAGACCTTCAAATACCTGTCTAACGACCCGGACGTTATCTACCC

GTGCGTTGACCTGTCTACCATCGAAATCGAAGACATCGACAAAAAATT

CTTCAAAACCGTTTTCAACGAAGGTGACCGTTTCTACCTGTCTATCAA

CCGTTTCGAAAAAAAAAAAGACGTTGCTCTGGCTATCAAAGCTTTCGC

TCTGTCTGAAGACCAGATCAACGACAACGTTAAACTGGTTATCTGCGG

TGGTTACGACGAACGTGTTGCTGAAAACGTTGAATACCTGAAAGAACT

GCAGTCTCTGGCTGACGAATACGAACTGTCTCACACCACCATCTACTA

CCAGGAAATCAAACGTGTTTCTGACCTGGAATCTTTCAAACCAACAA

CTCTAAAATCATCTTCCTGACCTCTATCTTCTTCTCTGAAAGAACTGC

TGCTGGAACGTACCGAAATGCTGCTGTACACCCCGGCTTACGAACACT

TCGGTATCGTTCCGCTGGAAGCTATGAAACTGGGTAAACCGGTTCTGG

CTGTTAACAACGGTGGTCCGCTGGAAACCATCAAATCTTACGTTGCTG

GTGAAAACGAATCTTCTGCTACCGGTTGGCTGAAACCGGCTGTTCCGA

TCCAGTGGGCTACCGCTATCGACGAATCTCGTAAATCCTGCAGAACG

GTTCTGTTAACTTCGAACGTAACGGTCCGCTGCGTGTTAAAAAATACT

TCTCTCGTGAAGCTATGACCCAGTCTTTCGAAGAAAACGTTGAAAAAG

TTATCTGGAAAGAAAAAAAATACTACCCGTGGGAAATCTTCGGTATCT

CTTTCTCTAACTTCATCCTGCACATGGCTTTCATCAAAATCCTGCCGA

ACAACCCGTGGCCGTTCCTGTTCATGGCTACCTTCATGGTTCTGTACT

TCAAAAACTACCTGTGGGGTATCTACTGGGCTTTCGTTTTCGCTCTGT

CTTACCCGTACGAAGAAATCTAA

The prokaryotic host cell of the present invention has eukaryotic flippase activity in the form of Rft1 activity. As shown in FIG. 10B, Rft1 (or PglK) shifts the oligosaccharide assembly of GlcNAc units and mannose units from the cytoplasmic side of the inner membrane of the prokaryote host to the periplasm side. The Rft1 wild-type nucleic acid molecule has the nucleotide sequence of SEQ ID NO: 9:

atggcgaaaaaaaactcacaattgccctctactagtgagcagatcttg gaaaggtccacaacaggagctaccttcctcatgatgggccaactttc accaaaactggtaacgttcatactaaataatttgttgatcaggtttct gtcgcccagaattttcggtatcacggcctttctagaatttatacaggg cacagtgttattttttagcagagatgcgattcgtctgtcgacgttgag aatctcagactccggtaatggaataatcgatgatgacgacgaggagga gtaccaggaaactcattacaagtctaaagttttgcaaaccgcagtcaa ttttgcttacattccgttttggatcgggtttccactgtccattggtct tatcgcctggcagtacagaaacatcaacgcgtatttcatcactcttcc attcttcaggtggtcgatttttcttatctggctgagtatcatcgtgga gctgttaagcgagccattcttcatcgtcaaccagtttatgttgaacta tgccgcaaggtcaagatttgaaagcatcgcggtgactacaggatgtat tgtcaattttatagttgtttatgccgttcagcaatcccgctacccaat gggggttgtcacatcggacattgacaaagaaggcatcgccatattggc atttgccttgggaaagttagcacattcgatcaccctgctagcatgtta ctactgggactatctcaagaatttcaaaccaaagaaattgttcagtac caggctaacgaagataaaaacgcgtgaaaataacgaattgaagaaagg ctacccaaagagcacatcttattttttccaaaacgacattttacagca cttcaaaaaagtttattttcaactatgttttaagcatttgttgacaga gggtgataagttgattatcaattctttatgtactgtggaagaacaagg catttacgctctattgtcgaactatggatcgctactaacaagattatt atttgcgccgatcgaagaatctctgcggttattttttggcccgtttatt atcctcgcataaccctaaaaatttaaaactatctattgaagtcctggt gaatttaacaaggttttacatatacttatcgttaatgatcattgtatt tgggcctgccaattcatcctattattgcagttcttgattggctcgaaa tggtccactacttccgtatggacactataagagtctactgcttttaca -continued

```
tcccatattatcgcttaatggtattttgaagctttttccagagtgt
agccactggtgaccaaattttgaaacattcataattatgatggccttt
tctggtattttcctgctcaattcctggcttcttattgaaaaactcaaa
ctatcaatcgaaggcttgatattgagtaacatcattaacatggtgttg
agaatattgtattgtggagttttcttgaataaatttcatagggaactg
tttacagattcctcttttttcttcaattttaaggatttcaaaacagtt
attattgctggctcaacgatctgtctacttgactggtggtttattggg
tacgttaaaaatttacaacaatttgttgttaacgtattattcgcaatg
ggattgttagcgttaattttggtcaaggagcgccaaaccatacaatct
tttattaacaagagggcggtttccaattctaaagatgtataa.
```

The rft1 codon optimized nucleic acid molecule has the nucleotide sequence of SEQ ID NO: 10 as follows:

```
ATGGCTAAAAAAAACTCTCAGCTGCCGTCTACCTCTGAACAGATCCTG
GAACGTTCTACCACCGGTGCTACCTTCCTGATGATGGGTCAGCTGTTC
ACCAAACTGGTTACCTTCATCCTGAACAACCTGCTGATCCGTTTCCTG
TCTCCGCGTATCTTCGGTATCACCGCTTTCCTGGAATTCATCCAGGGT
ACCGTTCTGTTCTTCTCGTGACGCTATCCGTCTGTCTACCCTGCGT
ATCTCTGACTCTGGTAACGGTATCATCGACGACGACGACGAAGAAGAA
TACCAGGAAACCCACTACAAATCTAAAGTTCTGCAGACCGCTGTTAAC
TTCGCTTACATCCCGTTCTGGATCGGTTTCCCGCTGTCTATCGGTCTG
ATCGCTTGGCAGTACCGTAACATCAACGCTTACTTCATCACCCTGCCG
TTCTTCCGTTGGTCTATCTTCCTGATCTGGCTGTCTATCATCGTTGAA
CTGCTGTCTGAACCGTTCTTCATCGTTAACCAGTTCATGCTGAACTAC
GCTGCTCGTTCTCGTTTCGAATCTATCGCTGTTACCACCGGTTGCATC
GTTAACTTCATCGTTGTTTACGCTGTTCAGCAGTCTCGTTACCCGATG
GGTGTTGTTACCTCTGACATCGACAAAGAAGGTATCGCTATCCTGGCT
TTCGCTCTGGGTAAACTGGCTCACTCTATCACCCTGCTGGCTTGCTAC
TACTGGGACTACCTGAAAAACTTCAAACCGAAAAAACTGTTCTCTACC
CGTCTGACCAAAATCAAACCCGTGAAAACAACGAACTGAAAAAAGGT
TACCCGAAATCTACCTCTTACTTCTTCCAGAACGACATCCTGCAGCAC
TTCAAAAAAGTTTACTTCCAGCTGTGCTTCAAACACCTGCTGACCGAA
GGTGACAAACTGATCATCAACTCTCTGTGCACCGTTGAAGAACAGGGT
ATCTACGCTCTGCTGTCTAACTACGGTTCTCTGCTGACCCGTCTGCTG
TTCGCTCCGATCGAAGAATCTCTGCGTCTGTTCCTGGCTCGTCTGCTG
TCTTCTCACAACCCGAAAAACCTGAAACTGTCTATCGAAGTTCTGGTT
AACCTGACCCGTTTCTACATCTACCTGTCTCTGATGATCATCGTTTTC
GGTCCGGCTAACTCTTCTTTCCTGCTGCAGTTCCTGATCGGTTCTAAA
TGGTCTACCACCTCTGTTCTGGACACCATCCGTGTTTACTGCTTCTAC
ATCCCGTTCCTGTCTCTGAACGGTATCTTCGAAGCTTTCTTCCAGTCT
GTTGCTACCGGTGACCAGATCCTGAAACACTCTTACTTCATGATGGCT
TTCTCTGGTATCTTCCTGCTGAACTCTTGGCTGCTGATCGAAAAACTG
AAACTGTCTATCGAAGGTCTGATCCTGTCTAACATCATCAACATGGTT
CTGCGTATCCTGTACTGCGGTGTTTTCCTGAACAAATTCCACCGTGAA
CTGTTCACCGACTCTTCTTTCTTCTTCAACTTCAAAGACTTCAAAACC
GTTATCATCGCTGGTTCTACCATCTGCCTGCTGGACTGGTGGTTCATC
GGTTACGTTAAAAACCTGCAGCAGTTCGTTGTTAACGTTCTGTTCGCT
ATGGGTCTGCTGGCTCTGATCCTGGTTAAAGAACGTCAGACCATCCAG
TCTTTCATCAACAAACGTGCTGTTTCTAACTCTAAAGACGTTTAA.
```

The prokaryotic host cell of the present invention has eukaryotic oligosaccharyl transferase activity in the form of STT3 activity. As shown in FIG. 10B, the STT3 enzyme (or the PlgB enzyme) transports the oligosaccharide assembly from the inner membrane to an acceptor protein which is transported to the outer membrane of the host cell. The STT3 wild-type nucleic acid molecule has the nucleotide sequence of SEQ ID NO: 11:

```
atgggatccgaccggtcgtgtgttttgtctgtgatcagaccatcctca
agctcgtcatcttcgtggcgattrttggggctgccatatcatcacgat
gtttgcagtcatcaaatttgagtctattatccatgaattcgacccctg
gttcaattatagggctaccaaatatctcgtcaacaattcgattacaag
tattgaactggtttgacgaccgtacctggtacccctcggaagggtta
ctggagggactttatatcctggtttgatgacgactagtgcgttcatct
ggcacgccctgcgcaactggttgggcttgcccattgacatcagaaacg
tttgtgtgctatttgcgccactattactggggtcaccgcctgggcgac
ttacgaatttacgaaagagattaaagatgccagcgctgggcttaggct
gctggttttatagccattgtccccggttatatatctagatcagtggcg
gggtcctacgataatgaggccattgccattacactattaatggtcact
tTcatgttttggattaaggcccaaaagactggctctatcatgcacgca
acgtgtgcagcttattctacttctacatggtgtcggcttggggtgga
tacgtgttcatccaacttgatcccactccatgtcttttgctgatt
ttgatgggcagatattcgtccaaactgtattctgcctacaccacttgg
tacgctattggaactgttgcatccatgcagatcccatttgtcggttc
ctacctatcaggtctaacgaccacatggccgcattgggtgttttcggt
ttgattcagattgtcgccttcggtgacttcgtgaagggccaaatcagc
acagctaagtttaaagtcatcatgatggtttctctgtttttgatcttg
gtccttggtgtggtcggactttctgccttgacctatatggggttgatt
gccccttggactggtagattttattcgttatgggataccaactacgca
aagatccacattcctatcattgcctccgtaccgaacatcaacccgttt
cgtggcccgattcttcttgatcccacatttgatctggctattcccc
gccggtgtattcctactattcctcgacttgaaagacgagcacgttttt
gtcatcgcttactccgttctgtgttcgtactttgccggtgttatggtt
agattgatgagactttgacaccagtcatctgtgtgtccgccgccgtcg
```

```
cattgtccaagatatttgacatctacctggatttcaagacaagtgacc gcaaatacgccatcaaacctgcggcactactggccaaattgattgatc cggatcattcatatttatttgtatcttttcgtcttccattctacttgg gtaacaagaactgcatactcttctccttctgttgttttgccatcacaa accccagatggtaaattggcgttgatcgacgacttcagggaagcgtac tattggttaagaatgaactctgatgaggacagtaaggttgcagcgtgg tgggattacggttaccaaattggtggcatgttagacagaaccacttta gtcgataacaacacgtggaacaatactcacatcgccatcgttggtaaa gccatggcttccctgaagagaaatcttacgaaattctaaaagagcat gatgtcgattatgtcttggtcatattggtggtctaattgggtttggtg gtgatgacatcaaaaattcttgtggatgatcagaattagcgagggaat ctggccagaagagataaaagagcgtgatttctataccgcagagggaga atacagagtagatgcaagggcttctgagaccatgaggaactcgctact ttacaagatgtcctacaaagatttcccacaattattcaatggtggcca agccactgacagagtgcgtcaacaaatgatcacaccattagacgtccc accattagactacttcgacgaagttttttacttccgaaaactggatggt agaatatatcaattgaagaaggatgatgcccaaggtagaactttgagg gacgttggtgagttaaccaggtcttctacgaaaaccagaaggtccata aagagacctgaattagtttgagagtctaa
```

The STT3 codon optimized nucleic acid molecule has the nucleotide sequence of SEQ ID NO: 12 as follows:

```
ATGGGTTCTGACCGTTCTTGCGTTCTGTCTGTTTTCCAGACCATCCTG

AAACTGGTTATCTTCGTTGCTATCTTCGGTGCTGCTATCTCTTCTCGT

CTGTTCGCTGTTATCAAATTCGAATCTATCATCCACGAATTCGACCCG

TGGTTCAACTACCGTGCTACCAAATACCTGGTTAACAACTCTTTCTAC

AAATTCCTGAACTGGTTCGACGACCGTACCTGGTACCCGCTGGGTCGT

GTTACCGGTGGTACCCTGTACCCGGGTCTGATGACCACCTCTGCTTTC

ATCTGGCACGCTCTGCGTAACTGGCTGGGTCTGCCGATCGACATCCGT

AACGTTTGCGTTTTGTTCGCTCCGCTGTTCTCTGGTGTTACCGCTTGG

GCTACCTACGAATTCACCAAAGAAATCAAAGACGCTTCTGCTGGTCTG

CTGGCTGCTGGTTTCATCGCTATCGTTCCGGGTTACATCTCTCGTTCT

GTTGCTGGTTCTTACGACAACGAAGCTATCGCTATCACCCTGCTGATG

GTTACCTTCATGTTCTGGATCAAAGCTCAGAAACCGGTTCTATCATG

CACGCTACCTGCGCTGCTCTGTTCTACTTCTACATGGTTTCTGCTTGG

GGTGGTTACGTTTTCATCACCAACCTGATCCCGCTGCACGTTTTCCTG

CTGATCCTGATGGGTCGTTACTCTTCTAAACTGTACTCTGCTTACACC

ACCTGGTACGCTATCGGTACCGTTGCTTCTATGCAGATCCCGTTCGTT

GGTTTCCTGCCGATCCGTTCTAACGACCACATGGCTGCTCTGGGTGTT

TTCGGTCTGATCCAGATCGTTGCTTTCGGTGACTTCGTTAAAGGTCAG

ATCTCTACCGCTAAATTCAAAGTTATCATGATGGTTTCTCTGTTCCTG

ATCCTGGTTCTGGGTGTTGTTGGTCTGTCTGCTCTGACCTACATGGGT

CTGATCGCTCCGTGGACCGGTCGTTTCTACTCTCTGTGGGACACCAAC

TACGCTAAAATCCACATCCCGATCATCGCTTCTGTTTCTGAACACCAG

CCGGTTTCTTGGCCGGCTTTCTTCTTCGACACCCACTTCCTGATCTGG

CTTTTCCCGGCTGGTGTTTTCCTGCTGTTCCTGGACCTGAAAGACGAA

CACGTTTTCGTTATCGCTTACTCTGTTCTGTGCTCTTACTTCGCTGGT

GTTATGGTTCGTCTGATGCTGACCCTGACCCCGGTTATCTGCGTTTCT

GCTGCTGTTGCTCTGTCTAAAATCTTCGACATCTACCTGGACTTCAAA

ACCTCTGACCGTAAATACGCTATCAAACCGGCTGCTCTGCTGGCTAAA

CTGATCGTTTCTGGTTCTTTCATCTTCTACCTGTACCTGTTCGTTTTC

CACTCTACCTGGGTTACCCGTACCGCTTACTCTTCTCCGTCTGTTGTT

CTGCCGTCTCAGACCCCGGACGGTAAACTGGCTCTGATCGACGACTTC

CGTGAAGCTTACTACTGGCTGCGTATGAACTCTGACGAAGACTCTAAA

GTTGCTGCTTGGTGGGACTACGGTTACCAGATCGGTGGTATGGCTGAC

CGTACCACCCTGGTTGACAACAACACCTGGAACAACACCCACATCGCT

ATCGTTGGTAAAGCTATGGCTTCTCCGGAAGAAAAATCTTACGAAATC

CTGAAAGAACACGACGTTGACTACGTTCTGGTTATCTTCGGTGGTCTG

ATCGGTTTCGGTGGTGACGACATCAACAAATTCCTGTGGATGATCCGT

ATCTCTGAAGGTATCTGGCCGGAAGAAATCAAAGAACGTGACTTCTAC

ACCGCTGAAGGTGAATACCGTGTTGACGCTCGTGCTTCTGAAACCATG

CGTAACTCTCTGCTGTACAAAATGTCTTACAAAGACTTCCCGCAGCTG

TTCAACGGTGGTCAGGCTACCGACCGTGTTCGTCAGCAGATGATCACC

CCGCTGGACGTTCCGCCGCTGGACTACTTTCGACGAAGTTTCACCTC

TGAAAACTGGATGGTTCGTATCTACCAGCTGAAAAAAGACGACGCTCA

GGTCGTACCCTGCGTGACGTTGGTGAACTGACCCGTTCTTCTACCAAA

ACCCGTCGTTCTATCAAACGTCCGGAACTGGGTCTGCGTGTTTAA.
```

The successful expression of eukaryotic proteins, especially membrane proteins, in *E. coli* and other bacteria is a nontrivial task (Baneyx et al., "Recombinant Protein Folding and Misfolding in *Escherichia coli*," *Nat Biotechnol* 22:1399-1408 ((2004), which is hereby incorporated by reference in its entirety). Thus, consideration has to be given to numerous issues in order to achieve high expression yields of correctly folded and correctly localized proteins (e.g., insertion into the inner membrane). All of these factors collectively dictate whether the eukaryotic proteins will be functional when expressed inside *E. coli* cells.

In one embodiment of the present invention, eukaryotic glycosyltransferases can be codon optimized to overcome limitations associated with the codon usage bias between *E. coli* (and other bacteria) and higher organisms, such as yeast and mammalian cells. Codon usage bias refers to differences among organisms in the frequency of occurrence of codons in protein-coding DNA sequences (genes). A codon is a series of three nucleotides (triplets) that encodes a specific amino acid residue in a polypeptide chain. Codon optimization can be achieved by making specific transversion nucleotide changes, i.e. a purine to pyrimidine or pyrimidine to purine nucleotide change, or transition nucleotide change, i.e. a purine to purine or pyrimidine to pyrimidine nucleotide change. Exemplary codon optimized nucleic acid molecules corresponding to wild-type eukaryotic dolichyl-linked UDP-GlcNAc transferase (SEQ ID NOs: 1 and 3), eukaryotic mannosyltransferase (SEQ ID NOs: 5 and 7), eukaryotic flippase (SEQ ID NO: 9), and eukaryotic oligosaccharyl transferase (SEQ ID NO: 11) are set forth above as SEQ ID NOs: 2, 4, 6, 8, 10, and 12, respectively.

FIG. 13 thru 18 are sequence alignments showing specific nucleotides in the wildtype sequences of Alg1, Alg2, Alg3, Alg4, Rft1, and Sttc3, respectively, subject to transversion and transition changes to achieve codon optimized nucleotide sequences. An exemplary optimized sequence is shown in the sequence alignment and identified as "optimized" and the wildtype sequence is identified as "query". The location of nucleotide changes in the wildtype sequences are shown using the following convention: "|" indicates an unchanged nucleotide (i.e. the nucleotide of the wildtype sequence is not changed in the optimized sequence); "*" indicates the location of a transversion change (e.g. adenine "A" changed to a cytosine "C" or thymine "T"; guanine "G" changed to C or T; C changed to A or G; and T changed to A or G); and "#" indicates the location of a transition change (e.g. A to G or G to A; C to T or T to C). Although an exemplary optimized sequence is shown in each of FIG. 13 thru 18, one of skill in the art will readily appreciate that not all of the identified nucleotide changes must be made to achieve a codon optimized sequence and that in the case of a transversion change, two nucleotide changes are possible at each location (i.e. a purine can be changed to either pyrimidine (C or T) and a pyrimidine can be changed to either purine (A or G)).

The nucleic acid molecules and homologs, variants and derivatives of the alg genes comprising sequences have at least 75% identity to SEQ ID NO:6, 77% identity to SEQ ID NO:8, 77% identity to SEQ ID NO:2, and 77% identity to SEQ ID NO:4.

In another embodiment, the nucleic acid molecule of the present invention encodes a polypeptide encoded by the polynucleotides of SEQ ID NO:2, 4, 6, 8. Preferably, the nucleic acid molecule encodes a polypeptide sequence of at least 75%, 77%, 80%, 85%, 90%, or 95% identical to SEQ ID NO:2, 4, 6, 8, with the identity values, rising to 80%, 85%, 90%, 95%, 98%, 99%, 99.9%, or even higher.

In further embodiments, the nucleic acid molecules, homologs, variants, and derivatives of the flippase genes have a nucleotide sequence at least 76% identity to SEQ ID NO:10. Further, the nucleic acid molecule of the present invention encodes a polypeptide encoded by the polynucleotides of SEQ ID NO: 10. Preferably, the nucleic acid molecule encodes a polypeptide sequence of at least 76%, 80%, 85%, 90% or 95% identical to SEQ ID NO: 10, with the identity values increasing to 98%, 99%, 99.9%, or even higher.

In various other embodiments, the nucleic acid molecule and homologs, variants and derivatives of the OST genes have at least 79% identity to SEQ ID NO:12. In another embodiment, the nucleic acid molecule of the present invention encodes a polypeptide encoded by the polynucleotides of SEQ ID NO: 12. Preferably, the nucleic acid molecule encodes a polypeptide sequence of at least 79%, 80%, 85%, 90%, or 95% identical to SEQ ID NO: 12, with the identity values increasing to 98%, 99%, 99.9%, or even higher.

The present invention also encompasses nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing can be performed at temperatures about 5° C. lower than the $T_m$ for the specific DNA hybrid under a particular set of conditions.

The polynucleotides or nucleic acid molecules of the present invention refer to the polymeric form of nucleotides of at least 10 bases in length. These include DNA molecules (e.g., linear, circular, cDNA, chromosomal, genomic, or synthetic, double stranded, single stranded, triple-stranded, quadruplexed, partially double-stranded, branched, hair-pinned, circular, or in a padlocked conformation) and RNA molecules (e.g., tRNA, rRNA, mRNA, genomic, or synthetic) and analogs of the DNA or RNA molecules of the described as well as analogs of DNA or RNA containing non-natural nucleotide analogs, non-native inter-nucleoside bonds, or both. The isolated nucleic acid molecule of the invention includes a nucleic acid molecule free of naturally flanking sequences (i.e., sequences located at the 5' and 3' ends of the nucleic acid molecule) in the chromosomal DNA of the organism from which the nucleic acid is derived. In various embodiments, an isolated nucleic acid molecule can contain less than about 10 kb, 5 kb, 4 kb, 3 kb, 2 kb, 1 kb, 0.5 kb, 0.1 kb, 50 bp, 25 by or 10 by of naturally flanking nucleotide chromosomal DNA sequences of the microorganism from which the nucleic acid molecule is derived.

The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art, as described by Sambrook et al., *Molecular Cloning: A Laboratory Manual*, Cold Springs Laboratory Press, Cold Springs Harbor, N.Y. (1989), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if *E. coli* is used as a host cell, plasmids such as pUC19, pUC18, or pBR322 may be used. Other suitable expression vectors are described in *Molecular Cloning: a Laboratory Manual:* 3rd edition, Sambrook and Russell, 2001, Cold Spring Harbor Laboratory Press, which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in *Current Protocols in Molecular Biology*, Ausubel et al. eds., (1992), which is hereby incorporated by reference in its entirety.

Different genetic signals and processing events control many levels of gene expression (e.g., DNA transcription and messenger RNA ("mRNA") translation) and subsequently the amount of fusion protein that is displayed on the ribosome surface. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression and surface display. Therefore, depending upon the host system utilized, any one of a number of suitable promoters may also be incorporated into the expression vector carrying the deoxyribonucleic acid molecule encoding the protein of interest coupled to a stall sequence. For instance, when using *E. coli*, its bacteriophages, or plasmids, promoters such as the T7 phage promoter, lac promoter, tip promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

In accordance with the present invention, the host cell is a prokaryote. Such cells serve as a host for expression of recombinant proteins for production of recombinant therapeutic proteins of interest. Exemplary host cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp., *Stenotrophomonas* sp., *Micrococcus* sp., *Neisseria* sp., *Bdellovibrio* sp., *Hemophilus* sp., *Klebsiella* sp., *Proteus mirabilis, Enterobacter cloacae, Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

In one embodiment of the present invention, the *E. coli* host strain C41(DE3) is used, because this strain has been previously optimized for general membrane protein overexpression (Miroux et al., "Over-production of Proteins in *Escherichia coli*: Mutant Hosts That Allow Synthesis of Some Membrane Proteins and Globular Proteins at High Levels," *J Mol Biol* 260:289-298 (1996), which is hereby incorporated by reference in its entirety). Further optimization of the host strain includes deletion of the gene encoding the DnaJ protein (e.g., ΔdnaJ cells). The reason for this deletion is that inactivation of dnaJ is known to increase the accumulation of overexpressed membrane proteins and to suppress the severe cytotoxicity commonly associated with membrane protein overexpression (Skretas et al., "Genetic Analysis of G Protein-coupled Receptor Expression in *Escherichia coli*: Inhibitory Role of DnaJ on the Membrane Integration of the Human Central Cannabinoid Receptor," *Biotechnol Bioeng* (2008) which is hereby incorporated by reference in its entirety). Applicants have observed this following expression of Alg1 and Alg2. Furthermore, deletion of competing sugar biosynthesis reactions is required to ensure optimal levels of N-glycan biosynthesis. For instance, the deletion of genes in the *E. coli* O16 antigen biosynthesis pathway (Feldman et al., "The Activity of a Putative Polyisoprenol-linked Sugar Translocase (Wzx) Involved in *Escherichia coli* O Antigen Assembly is Independent of the Chemical Structure of the O Repeat," *J Biol Chem* 274:35129-35138 (1999), which is hereby incorporated by reference in its entirety) will ensure that the bactoprenol-GlcNAc-PP substrate is available for desired mammalian N-glycan reactions. To eliminate unwanted side reactions, the following are representative genes that are deleted from the *E. coli* host strain: wbbL, glcT, glf, gafT, wzx, wzy, waaL.

Methods for transforming/transfecting host cells with expression vectors are well-known in the art and depend on the host system selected, as described in Sambrook et al., *Molecular Cloning: A Laboratory Manual*, Cold Springs Laboratory Press, Cold Springs Harbor, N.Y. (1989), which is hereby incorporated by reference in its entirety. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation, and transfection using bacteriophage.

One aspect of the present invention is directed to a glycoprotein conjugate comprising a protein and at least one peptide comprising a D-$X_1$-N-$X_2$-T (SEQ ID NO: 17) motif fused to the protein, wherein D is aspartic acid, $X_1$ and $X_2$ are any amino acid other than proline, N is asparagine, and T is threonine.

Another aspect of the present invention is directed to a method of producing a glycosylated protein. This method comprises providing a prokaryotic host cell comprising eukaryotic glycosyltransferase activity, where the eukaryotic glycosyltransferase activity is eukaryotic dolichyl-linked UDP-GlcNAc transferase activity and eukaryotic mannosyltransferase activity. The prokaryotic host cell is then cultured under conditions effective to produce a glycosylated protein.

The method of the present invention can be used to produce a glycosylated antibody in accordance with the present invention.

Accordingly, in various aspects, the present invention provides a prokaryotic protein expression system that is engineered to "humanize" N-linked proteins as a platform for the stereospecific biosynthesis of a vast array of N-linked glycoproteins. In certain embodiments, reconstitution of a eukaryotic N-glycosylation pathway in *E. coli* using metabolic pathway and protein engineering techniques results in N-glycoproteins with structurally homogeneous human-like glycans. Since native glycosylation pathways are absent in the majority of bacteria, it is contemplated that glyco-engineered bacteria is capable of stereospecific production of N-linked glycoproteins with homogenous glycoform synthesized per cell. This ensures that each glyco-engineered cell line will correspond to a unique carbohydrate signature. It is, therefore, an object of the invention to engineer bacteria to produce human-like glycosylation.

The oligosaccharide chain attached by the prokaryotic glycosylation machinery is structurally distinct from that attached by higher eukaryotic and human glycosylation pathways (Weerapana et al., "Asparagine-linked Protein Glycosylation: From Eukaryotic to Prokaryotic Systems," *Glycobiology* 16:91R-101R (2006), which is hereby incorporated by reference in its entirety). In certain embodiments, to begin "humanizing" the bacterial glycosylation machinery (FIG. 10A), an object of the present invention is to generate the Man$_3$GlcNAc$_2$ oligosaccharide structure. In a first aspect, a recombinant pathway comprising the biosynthesis of lipid-linked Man$_3$GlcNAc$_2$ is constructed in *E. coli* (FIG. 10B). The first part of this pathway is the enzymatic synthesis of lipid-linked Man$_3$GlcNAc$_2$. Specifically, one of several eukaryotic glycosyltransferases is functionally expressed in *E. coli* and the resulting lipid-linked oligosaccharides is analyzed by metabolic labeling of cells with $^3$H-GlcNAc and $^3$H-mannose or with fluorescent lectins (e.g., AlexaFluor-ConA). The Man$_3$GlcNAc$_2$ oligosaccharide structure represents the core structure of most of the N-glycans found in eukaryotic cells. The glycosyltransferases required for the assembly of this structure are known in eukaryotes and most of these enzymes have been functionally expressed in *E. coli*, however to date, no one has been successful in achieving this oligosaccharide structure. In addition, the substrates of these glycosyltransferases, namely UDP-GlcNAc and GDP-Man, are both present in the cytoplasm of *E. coli*.

Site-Specific Transfer of Man$_3$GlcNAc$_2$ Core onto Target Proteins.

An additional part of the pathway to produce human-like oligosaccharide structures in prokaryotes entails the transfer of the Man$_3$GlcNAc$_2$ oligosaccharide to N-X-S/T sites on polypeptide chains. This requires functional expression of an integral membrane protein or protein complex known as an oligosaccharyltransferase (OST) that is responsible for the transfer of oligosaccharides to the target protein. Various prokaryotic and eukaryotic OSTs have the ability of to transfer the lipid-linked Man$_3$GlcNAc$_2$ oligosaccharide onto the target protein. Accordingly, the prokaryotic protein expression system comprises at least one OST activity.

In various aspects, reconstituting a eukaryotic glycosylation pathway in *E. coli* requires the activity of a flippase and an OST (PglK and PglB in *C. jejuni*, respectively, and Rft1 and STT3 in yeast, respectively) (see FIG. 10B). The PglK flippase is responsible for translocating the lipid-linked *C. jejuni* heptasaccharide across the inner membrane. Fortuitously, PglK exhibits relaxed specificity towards the glycan structure of the lipid-linked oligosaccharide intermediate (Alaimo et al., "Two Distinct But Interchangeable Mechanisms for Flipping of Lipid-linked Oligosaccharides," *Embo J* 25:967-76 (2006) and Wacker et al., "Substrate Specificity of Bacterial Oligosaccharyltransferase Suggests a Common Transfer Mechanism for the Bacterial and Eukaryotic Systems," *Proc Natl Acad Sci USA* 103:7088-93 (2006), which are hereby incorporated by reference in their entirety). Accordingly, it is contemplated that this enzyme will recognize lipid-linked Man$_3$GlcNAc$_2$ and thus no further engineering is required. Alternatively, in the unlikely event that PglK does not recognize lipid-linked Man$_3$GlcNAc$_2$, the present invention provides for expression of a eukaryotic flippase such as, among others Rft1.

"Target proteins", "proteins of interest", or "therapeutic proteins" include without limitation erythropoietin, cytokines such as interferons, G-CSF, coagulation factors such as factor VIII, factor IX, and human protein C, soluble IgE receptor α-chain, IgG, IgG fragments, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-feto proteins, AAT, rhTBP-1 (aka TNF binding protein I), TACI-Ig (transmembrane activator and calcium modulator and cyclophilin ligand interactor), FSH (follicle stimulating hormone), GM-CSF, GLP-1 w/ and w/o FC (glucagon like protein I) IL-1 receptor agonist, sTNFr (enbrel, aka soluble TNF receptor Fc fusion) ATIII, rhThrombin, glucocerebrosidase, CTLA4-Ig (Cytotoxic T Lymphocyte associated Antigen 4-Ig), receptors, hormones, human vaccines, animal vaccines, peptides, and serum albumin.

Aglycosylated vs. Glycosylated IgGs

Another aspect of the present invention relates to a glycosylated antibody comprising an Fv portion which recognizes and binds to a native antigen and an Fc portion which is glycosylated at a conserved asparagine residue.

The glycosylated antibody of the present invention can be in the form of a monoclonal or polyclonal antibody.

Figure 5A:
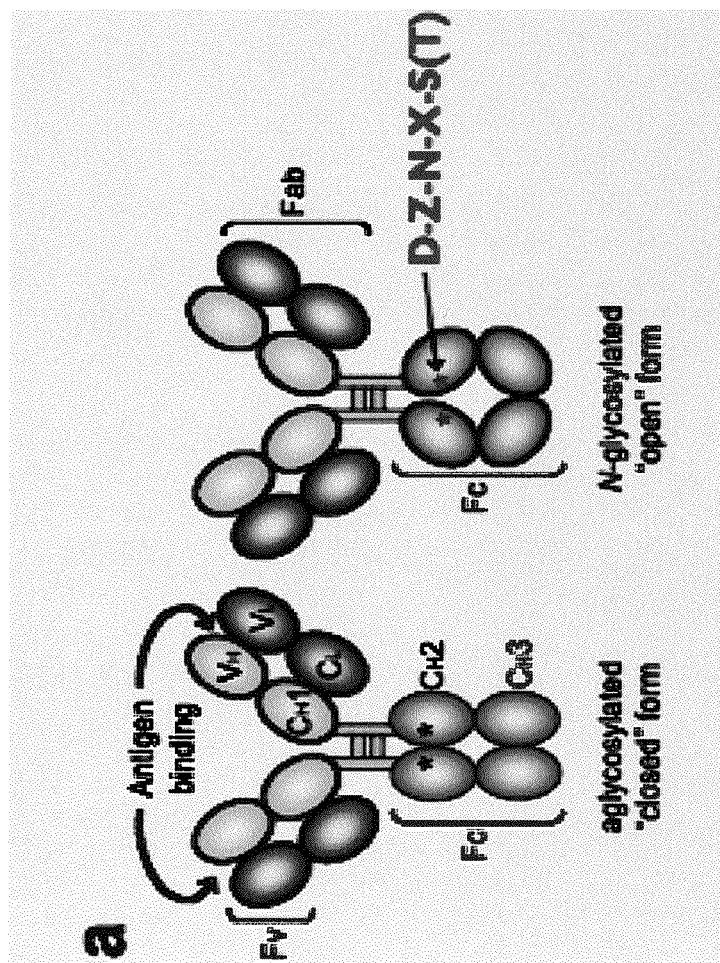
FIGS. 5A-C depict the results of glycosylated IgG M18.1 in pgl+ *E. coli*.

A single immunoglobulin molecule is comprised of two identical light (L) chains and two identical heavy (H) chains. Light chains are composed of one constant domain (C$_L$) and one variable domain (V$_L$) while heavy chains are consist of three constant domains (C$_H$1, C$_H$2 and C$_H$3) and one variable domain (V$_H$). Together, the V$_H$ and V$_L$ domains compose the antigen-binding portion of the molecule known as the Fv. The Fc portion is glycosylated at a conserved Asn297 residue (FIG. 5A indicated by asterisks). Attachment of N-glycan at this position results in an "open" conformation that is essential for effector interaction.

Monoclonal antibodies can be made using recombinant DNA methods, as described in U.S. Pat. No. 4,816,567 to Cabilly et al. and Anderson et al., "Production Technologies for Monoclonal Antibodies and their Fragments," *Curr Opin Biotechnol.* 15:456-62 (2004), which are hereby incorporated by reference in their entirety. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which are then transfected into the host cells of the present invention, and monoclonal antibodies are generated. In one embodiment, recombinant DNA techniques are used to modify the heavy and light chains with N-terminal export signal peptides (e.g., PelB signal peptide) to direct the heavy and light chain polypeptides to the bacterial periplasm. Also, the heavy and light chains can be expressed from either a bicistronic construct (e.g., a single mRNA that is translated to yield the two polypeptides) or, alternatively, from a two cistron system (e.g., two separate mRNAs are produced for each of the heavy and light chains). To achieve high-level expression and efficient assembly of full-length IgGs in the bacterial periplasm, both the bicistronic and two cistron constructs can be manipulated to achieve a favorable expression ratio. For example, translation levels can be raised or lowered using a series of translation initiation regions (TIRs) inserted just upstream of the bicistronic and two cistron constructs in the expression vector (Simmons et al., "Translational Level is a Critical Factor for the Secretion of Heterologous Proteins in *Escherichia coli*," *Nat Biotechnol* 14:629-34 (1996), which is hereby incorporated by reference in its entirety). When this antibody producing plasmid is introduced into a bacterial host that also harbors plasmid- or genome-encoded genes for expressing glycosylation enzymes, the resulting antibodies are glycosylated in the periplasm. Recombinant monoclonal antibodies or fragments thereof of the desired species can also be isolated from phage display libraries as described (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

In some embodiments, the antibody of the present invention is a humanized antibody. Humanized antibodies are antibodies that contain minimal sequences from non-human (e.g. murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Bispecific antibodies are also suitable for use in the methods of the present invention. Bispecific antibodies are antibodies that are capable of specifically recognizing and binding at least two different epitopes. Bispecific antibodies can be intact antibodies or antibody fragments. Techniques for making bispecific antibodies are common in the art (Traunecker et al., "Bispecific Single Chain Molecules (Janusins) Target Cytotoxic Lymphocytes on HIV Infected Cells," *EMBO J.* 10:3655-3659 (1991) and Gruber et al., "Efficient Tumor Cell Lysis Mediated by a Bispecific Single Chain Antibody Expressed in *Escherichia coli*," *J. Immunol.* 152:5368-74 (1994), which are hereby incorporated by reference in their entirety).

Glycan Screening Technologies

A further aspect of the present invention pertains to a method for screening bacteria or bacteriophages. This method involves expressing one or more glycans on the surface of a bacteria and attaching a label on the one or more glycans on the surface of the bacteria or on the surface of a bacteriophage derived from the bacteria. The most common bacteriophages used in phage display are M13 and fd filamentous phage, though T4, T7, and λ phage are also used. The label is then analyzed in a high-throughput format.

When a bacteriophage is subjected to labeling and analyzing, the method of the present invention further comprises infecting the bacteria expressing one or more glycans on the cell surface with a helper phage under conditions effective to produce a bacteriophage with one or more glycans on its surface. The bacteriophage is then enriched with one or more glycans on its surface. Alternatively, the use of the helper phage can be eliminated by using a novel 'bacterial packaging cell line' technology (Chasteen et al., "Eliminating Helper Phage From Phage Display," *Nucleic Acids Res* 34:e145 (2006), which is hereby incorporated by reference in its entirety).

The labeling can be carried out with a lectin which recognizes a glycan on the surface of the bacteria or bacteriophage and has a detectable label. Alternatively, the labeling step is carried out with an antibody which recognizes a glycan on the surface of the bacteria or bacteriophage and has a detectable label. Alternatively, by immobilizing a relevant protein target(s) (e.g., lectin, antibodies) to a solid support such as the surface of a 96-well plate, a cell or phage that displays a protein that binds to one of those targets on its surface will remain while others are removed by washing. Those that remain can be eluted, used to produce more cells (by culturing cells) or phage (by bacterial infection with helper phage) and so produce a cell or phage mixture that is enriched with relevant (i.e. binding) cell or phage. The repeated cycling of these steps is referred to as 'panning'.

This aspect of the present invention permits screening by cell surface display and glycophage display of glycoproteins where engineered bacterial cell lines produce diverse glycans and glycoproteins in a rapid and cost-effective manner. These assays allows for quantitative, high-throughput glycan analysis and rapid isolation of mutants that confer desired phenotypes. The underlying premise for these assays is that both cell surface display and phage display create a unique genotype (i.e., DNA) to phenotype (i.e., protein activity or modification such as glycosylation) linkage. This connection between genotype and phenotype enables large libraries of proteins to be screened and amplified in a process called in vitro selection, which is analogous to natural selection. These display technologies can be used to screen at least two different types of libraries. The first strategy is to create libraries of the glycoprotein itself (i.e., using error-prone PCR, DNA shuffling, etc), where variants can be produced with additional glycosylation sites that may be improved with respect to activity or stability following the introduction of additional (but identical) glycan structures. The second strategy is to make a large collection of different glycan structures by making libraries of individual pathway enzymes (i.e., using error-prone PCR, DNA shuffling, etc) or different enzyme combinations such that a combinatorial library of different glycan structures is produced and displayed on the cell or phage surface. The phenotype of the variant glycoprotein or the variant glycan structure is physically coupled to the genotype of the isolated cells (i.e., the sequence of the plasmid) or phages (i.e., the sequence of the packaged DNA known as a phagemid). Thus, the identity of the library clones is easily determined.

Display of N-Linked Glycoproteins on the Bacterial Cell Surface

Figures 6A, 6B:
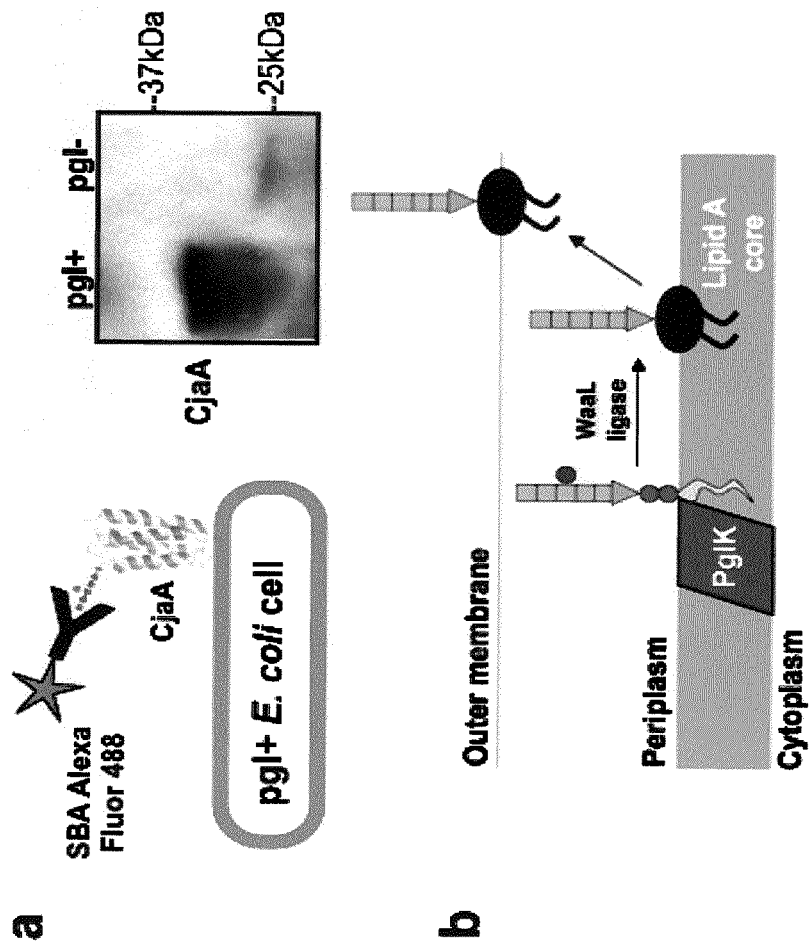
FIG. 6A shows a schematic of glycoprotein surface display and Western blot analysis confirming glycosylation of CjaA in pgl+ and pgl– cells via glycoprotein-specific antiserum (hR6P).
FIG. 6B shows the transfer of heptasaccharide to the outer surface via WaaL-mediated ligation to lipid A.
Figure 6C:
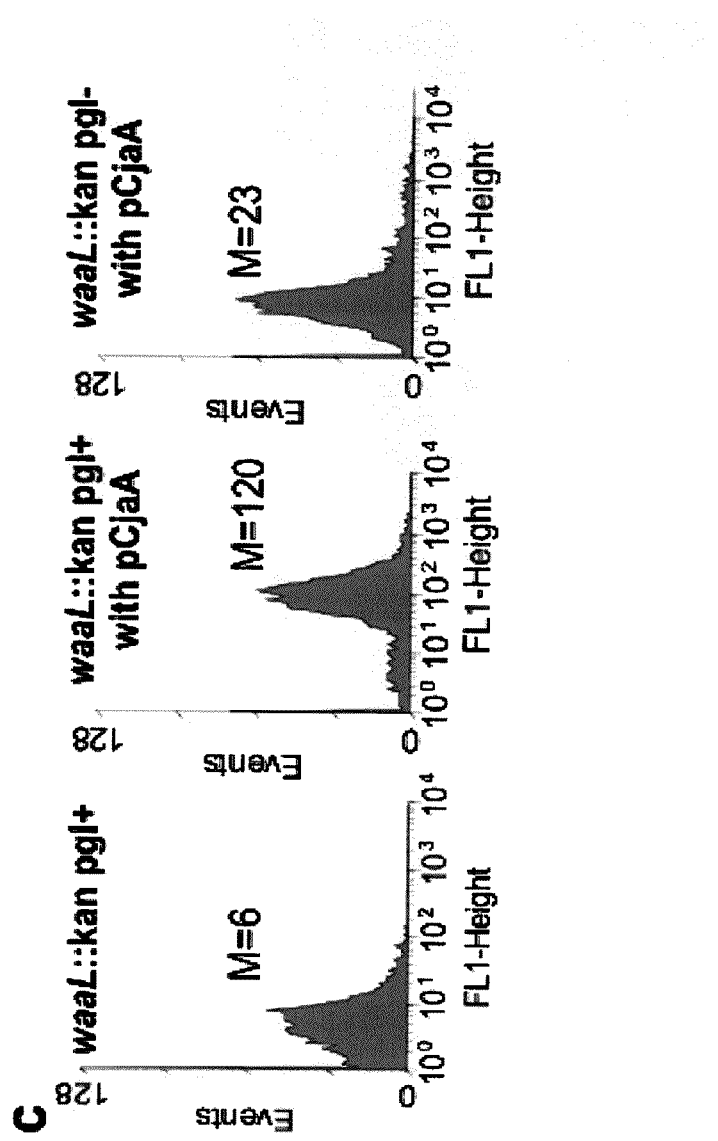
FIG. 6C shows the quantification of SBA-Alexa Fluor labeling using flow cytometry.

Glycosylation in *E. coli* for high-throughput screening can be carried out with the host cells and methods described above using eukaryotic glycosyltransferase activity, eukaryotic flippase activity, and eukaryotic oligosaccharyl activity. However, in the screening embodiment, activity from other sources can be utilized. For example, such bacterial surface display can be carried out with the *C. jejuni* CjaA protein as an outer membrane anchor (FIG. 6A). This protein is suitable primarily, because it is (i) localized to the outer membrane in *C. jejuni* and *E. coli* cells and (ii) glycosylated by the pgl system in *E. coli* (FIG. 6A). To determine if the N-glycan heptasaccharide on CjaA is surface exposed, pgl+ *E. coli* can be treated with a fluorescently labeled version of the lectin SBA (SBA-Alexa Fluor 488 conjugate, Molecular Probes). The cells further lacked the native *E. coli* WaaL ligase that transfers oligosaccharides from the bactoprenol lipid carrier to the lipid A core molecule (Raetz et al., "Lipopolysaccharide endotoxins," *Annu Rev Biochem* 71:635-700 (2002), which is hereby incorporated by reference in its entirety) (FIG. 6B). This ligase is known to have relaxed substrate specificity and is responsible for transfer of the bacterial heptasaccharide from bactoprenolpyrophosphate to the lipid A core, a molecule that is subsequently transferred to the outer side of the outer membrane. When pgl+ cells lacking waaL are transformed with the CjaA plasmid and induced to express CjaA, a strong fluorescent signal is detected following SBA-Alexa Fluor labeling (FIG. 6C). Importantly, this signal is dependent on the pgl system as a complete loss of fluorescence was observed following SBA-Alexa Fluor labeling of waaL mutants carrying the pgl– control vector (FIG. 6C). Accordingly, glycan analysis can be performed directly with living *E. coli* cells in a fluorescent format that is compatible with high-throughput screening.

Using a fluorescent version of the lectin Concanavalin A (ConA), which has a high affinity towards the tri-mannose structure of the core glycan, Man$_3$GlcNAc$_2$ can be assayed on the surface of *E. coli* cells. The basis for this strategy is the observation that bactoprenolpyrophosphate-linked oligosaccharides are the substrates for the *E. coli* WaaL ligase that transfers oligosaccharides from the bactoprenol lipid carrier to the lipid A core molecule (Raetz et al., "Lipopolysaccharide endotoxins," *Annu Rev Biochem* 71:635-700 (2002), which is hereby incorporated by reference in its entirety) (see FIG. 6B). Applicants expect the transfer of the Man$_3$GlcNAc$_2$ oligosaccharide from bactoprenolpyrophosphate to the lipid A core, a molecule that is subsequently transferred to the outer side of the outer membrane. The display of Man$_3$GlcNAc$_2$ on the surface of *E. coli* cells will be achieved by surface staining using a fluorescent version of ConA (AlexaFluor-ConA). This should make it possible to detect and quantify oligosaccharide biosynthesis using fluorescence activated cell sorting (FACS). Importantly, this measurement does not depend on flippase or OST activity. It has been observed that the bacterial oligosaccharide is localized to the outer surface of TG1 pgl+ cells as evidenced by a strong FACS signal following labeling with fluorescent SBA. Identical labeling of TG1 pglmut cells resulted in identical fluorescence profile, indicating that transfer of the oligosaccharide to lipid A did not depend on PglB. Finally, control cells lacking the pgl expression vector resulted in no detectable cell fluorescence. Applicants anticipate that this assay will allow optimization of oligosaccharide expression in *E. coli* with different inducible promoters and, if necessary, different signal peptides to direct correct insertion into the plasma membrane will be used. For instance, despite the promising expression results described in the present invention, it may prove useful to employ SRP- or YidC-dependent targeting (Luirink et al., "Biogenesis of Inner Membrane Proteins in *Escherichia coli*," *Annu Rev Microbiol* 59:329-55 (2005), which is hereby incorporated by reference in its entirety) of each Alg membrane protein in combination with an *E. coli* host strain such as C41(DE3) that has been specifically engineered for high-level expression of heterologous membrane proteins (Miroux et al., "Over-production of Proteins in *Escherichia coli*: Mutant Hosts That Allow Synthesis of Some Membrane Proteins and Globular Proteins at High Levels," *J Mol Biol* 260:289-98 (1996), which is hereby incorporated by reference in its entirety). Moreover, since deletion of waaL eliminates oligosaccharide transfer to lipid A (FIG. 6C), the ConA labeling strategy can be used in combination with a surface displayed glycoprotein (e.g., CjaA, see FIG. 6) to assay for glycoprotein variants with improved or new properties (e.g., increased activity or stability) or pathway enzymes such as glycosyltransferase, flippase or OST with improved or new activities (e.g., ability to create different or novel glycan structures) (see FIG. 10B). This can be accomplished as follows: the DNA encoding the protein or peptide of interest is itself a surface protein (e.g., *C. jejuni* CjaA) or is ligated in-frame to a cell surface protein (e.g., *E. coli* ClyA, OmpA, OmpX, etc). Multiple cloning sites are sometimes used to ensure that the fragments are inserted in all three possible frames so that the cDNA fragment is translated in the proper frame. The gene encoding the cell surface hybrid protein is cloned in an expression vector and transformed into bacterial cells such as TG1 or XL1-Blue *E. coli*. For creating glycoprotein variants, the incorporation of many different DNA fragments encoding either target glycoprotein as fusion to the cell surface protein gene generates a surface displayed library from which members of interest can be isolated. For creating pathway enzymes with new or improved activities, a DNA library of the enzyme is co-transformed into bacteria along with a plasmid expressing a reporter cell surface displayed glycoprotein (e.g., CjaA) that serves as carrier for the glycan structure or library of glycan structures. Co-transformed bacteria are then screened for the presence of a particular glycan structure attached to the surface displayed carrier.

*E. coli* GlycoPhage Display System

Another aspect of the present invention relates to a bacterial phage display system for glycans. The GlycoPhage display system is a powerful tool for engineering novel glycophenotypes with one embodiment being shown in FIG. 7. This is based on a modified version of filamentous phage display (Smith, G. P., "Filamentous Fusion Phage: Novel Expression Vectors that Display Cloned Antigens on the Virion Surface," *Science* 228:1315-7 (1985), which is hereby incorporated by reference in its entirety), where phagemids expressing AcrA of *C. jejuni* lacking the N-terminal lipid anchor sequence (Nita-Lazar et al., "The N-X-S/T Consensus Sequence is Required But Not Sufficient for Bacterial N-linked Protein Glycosylation," *Glycobiology* 15:361-7 (2005), which is hereby incorporated by reference in its entirety) fused to the N-terminus of the minor phage coat protein g3p were constructed. The pectate lyase B signal sequence (pelB) was cloned upstream of the acrA coding sequence for Sec-dependent translocation to the periplasmic space of E. coli. Expression of the fusion protein was directed by the arabinose inducible and glucose repressible pBAD promoter (Miyada et al., "Regulation of the araC Gene of Escherichia coli: Catabolite Repression, Autoregulation, and Effect on araBAD Expression," Proc Natl Acad Sci USA 81:4120-4 (1984), which is hereby incorporated by reference in its entirety). A 24-amino acid linker was juxtaposed between the expressed AcrA and the g3p domain on phagemid pAcrA-g3p. This linker sequence contained a hexa-histidine tag and an enterokinase cleavage site directly followed by an amber stop codon (UAG), that was transcribed as glutamine in E. coli supE strains (e.g., XL1-Blue, ER2738 or TG1) with an efficiency of 80-90% (Miller et al., "Effects of Surrounding Sequence on the Suppression of Nonsense Codons," Mol Biol 164:59-71 (1983), which is hereby incorporated by reference in its entirety). Inclusion of the phage F1 intergenic region (ori M13) on these vectors allowed for packaging of single-stranded phagemid after superinfection with helper phage. This technique can be used to assay for glycoprotein variants with improved or new properties (e.g., increased activity or stability) or pathway enzymes such as glycosyltransferase, flippase or OST with improved or new activities (e.g., ability to create different or novel glycan structures) (see FIG. 10B). For creating glycoprotein variants, the DNA encoding the protein or peptide of interest is ligated to the pIII or pVIII gene. Multiple cloning sites are sometimes used to ensure that the fragments are inserted in all three possible frames so that the cDNA fragment is translated in the proper frame. The phage gene and insert DNA hybrid is then transformed into bacterial cells such as TG1 or XL1-Blue E. coli. The phage particles will not be released from the E. coli cells until they are infected with helper phage, which enables packaging of the phage DNA and assembly of the mature virions with the relevant protein fragment as part of their outer coat on either the minor (pIII) or major (pVIII) coat protein. The incorporation of many different DNA fragments into the pIII or pVIII genes generates a library from which members of interest can be isolated. For the creation of pathway enzymes with improved or new activities such as the ability to synthesize different glycan structures, a DNA library of the enzyme(s) is co-transformed into bacteria along with a plasmid expressing a reporter phage displayed glycoprotein (e.g., AcrA or MBP with N- or C-terminal glyc-tag) that serves as a carrier for the glycan structure or library of glycan structures. Co-transformed bacteria are used to create phage libraries that are then screened for the presence of a particular glycan structure attached to the phage displayed carrier.

The above disclosure generally describes the present invention. A more specific description is provided below in the following examples. The examples are described solely for the purpose of illustration and are not intended to limit the scope of the present invention. Changes in form and substitution of equivalents are contemplated as circumstances suggest or render expedient. Although specific terms have been employed herein, such terms are intended in a descriptive sense and not for purposes of limitation.

EXAMPLES

Example 1

N-Linked Protein Glycosylation in Genetically Modified E. coli

Figure 3:
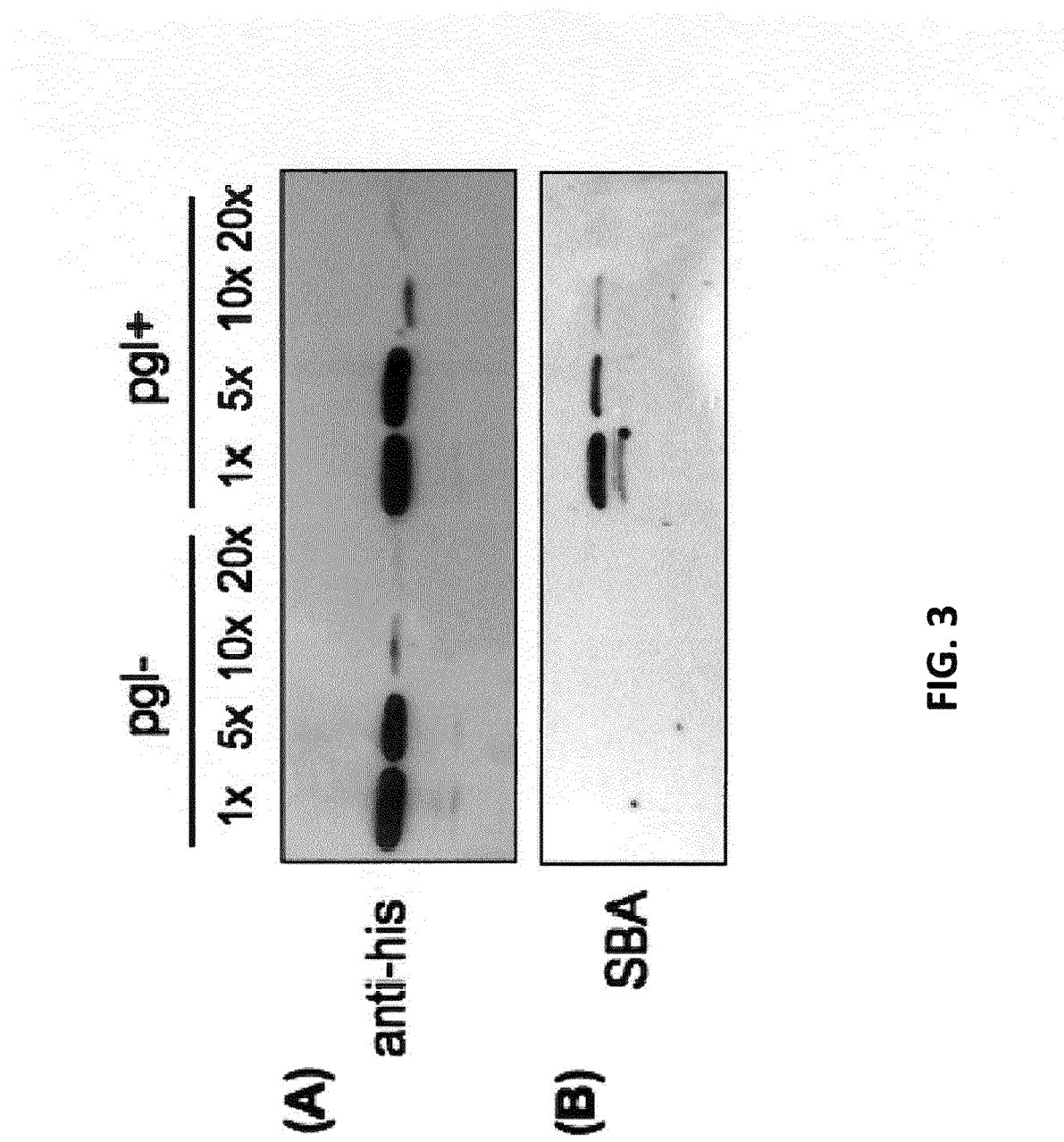
FIGS. 3A-B are photos of Western blots of glycosylated PEB3 in glyco-engineered *E. coli*. The *C. jejuni* glycosylation substrate PEB3, carrying a C-terminal 6×his tag, was expressed and purified from the periplasm of *E. coli* cells that co-expressed either the complete set of pgl genes from pACYC184-pgl (pgl+) or a modified pgl gene cluster that lacked the pglB gene encoding the essential OTase (pgl–). Purified PEB3 was detected in both pgl+ and pgl– cells, as evidenced by Western blotting using an anti-polyhistidine antibody (FIG. 3A). However, PEB3 was only glycosylated in pgl+ cells based on binding to the GalNAc-specific lectin SBA, whereas PEP3 from pgl– cells was aglycosylated (FIG. 3B). Purified PEB3 was serially-diluted as indicated.

The experiments of Wacker et al. are reproduced here, where the C. jejuni pgl genetic locus was functionally transferred to E. coli, conferring on these cells the ability to perform N-linked protein glycosylation (Wacker et al., "N-linked Glycosylation in Campylobacter jejuni and its Functional Transfer into E. coli," Science 298:1790-3 (2002), which is hereby incorporated by reference in its entirety). For these studies, the plasmid pACYC184-pgl (pgl+) and a control plasmid derived from pACYC184-pgl that carried an insertion mutation in the pglB gene encoding the essential OST (pACYC184-pglB::kan; pgl−) were employed. BL21 (DE3) E. coli cells were co-transformed with either a pgl+ or pgl− vector along with a second vector encoding the C. jejuni glycoprotein PEB3. His-tagged PEB3 was expressed in the periplasm in pgl+ and pgl− cells and purified from the periplasmic fraction using nickel affinity chromatography; Ni-NTA Spin Kit (QIAGEN). Purified PEB3 was serially-diluted and detected by Western blotting using an anti-polyhistidine antibody (Sigma). Glycosylated PEB3 was detected using the GalNAc-specific lectin soy bean agglutinin (SBA) which binds to the terminal α-linked GalNAc of the heptasaccharide glycan. As expected, it was observed that PEB3 was expressed efficiently in both pgl+ and pgl− cells (FIG. 3A), but only the PEB3 from pgl+ cells cross-reacted with the lectin SBA (FIG. 3B), which binds to the terminal α-linked GalNAc of the glycan and indicates a fully glycosylated protein.

Example 2

N-Linked Glycosylation of MBP with a Peptide Tag in Glyco-Engineered E. coli

E. coli maltose binding protein (MBP) was fused to a gene encoding four consecutive glycosylation sequons (GAT CAG AAC GCG ACC GGC GGT GAC CAA AAT GCC ACA GGT GGC GAT CAA AAC GCC ACC GGC GGT GAC CAG AAT GCG ACA) (SEQ ID NO: 13) in the SacI and HindIII sites of pTRC99A [Amersham Biosciences]. The gene encodes a peptide tag of four consecutive DQNAT SEQ ID NO: 14 peptides separated by two glycine residues. DQNAT (SEQ ID NO: 14) sequons were efficiently glycosylated by PglB during in vitro experiments (Chen et al., "From Peptide to Protein: Comparative Analysis of the Substrate Specificity of N-linked Glycosylation in C. jejuni," Biochemistry 46:5579-85 (2007), which is hereby incorporated by reference in its entirety). Such a tag fused to the C-terminus of MBP, also appended with a C-terminal 6×His tag for purification, was expressed in BL21(DE3) E. coli transformed with pACYC-pgl and pACYC-pglmut (PglB W458A, D459A) (Wacker et al., "N-linked Glycosylation in Campylobacter jejuni and its Functional Transfer into E. coli," Science 298: 1790-3 (2002), which is hereby incorporated by reference in its entirety). Further, the C. jejuni glycoprotein cjAcrA, MBP with an N-terminal tag prior to the mature domain of MBP, MBP lacking its native secretion signal peptide with a C-terminal tag, and MBP & green fluorescent protein (GFPmut2) with a C-terminal tag and a Tat-specific (ssTorA) signal peptide were expressed in an identical manner and purified by nickel affinity chromatography (Ni-NTA Spin Kit, Quiagen). Tags at the N-terminus or C-terminus of mature MBP were determined to be glycosylated by Western blot with anti-HIS serum (Promega) against the protein and hR6P serum that was raised against the bacterial heptasaccharide. Glycosylation was dependent on both a functional PglB and secretion to the periplasm, as neither MBP generated in E. coli transformed with pACYC-pglmut nor lacking a secretion signal peptide were glycosylated. Glycosylation occurred via the twin-arginine translocation (Tat) pathway as evidenced by the glycosylation of MBP and green fluorescent protein (GFP) targeted for secretion in this manner. The anti-heptasaccharide serum revealed at least three discrete bands characteristic of multiple attached N-glycans.

Figure 4:
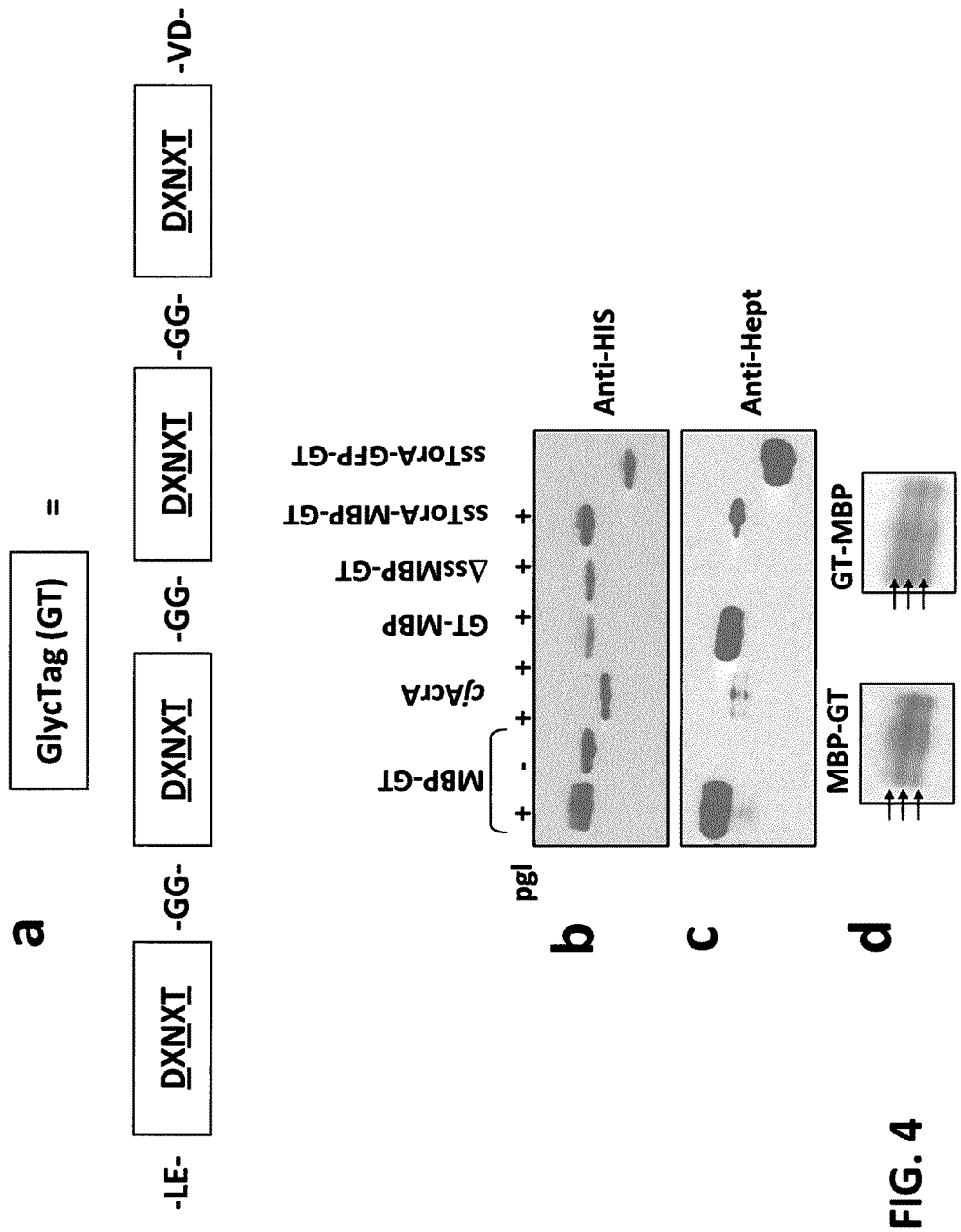
FIGS. 4A-D show the results of the glycosylation of *E. coli* maltose binding protein (MBP).

These results show that a peptide containing four consecutive D-$X_1$-N-$X_2$-T sequons were efficiently glycosylated by PglB during in vitro experiments (Chen et al., "From Peptide to Protein: Comparative Analysis of the Substrate Specificity of N-linked Glycosylation in *C. jejuni*," *Biochemistry* 46:5579-85 (2007), which is hereby incorporated by reference in its entirety). A GlycTag fused to the C-terminus of MBP was expressed in pgl+ and pgl– *E. coli* and purified to 20 mg/L. The resulting protein was efficiently glycosylated at multiple sites (FIGS. 4C and 4D). Similar results were seen when the GlycTag was moved to the N-terminus of MBP. MBP-GlycTag fusions generated in pgl– *E. coli* or expressed without a secretion signal peptide were not glycosylated (FIG. 4C), confirming that glycosylation was dependent upon PglB and export to the periplasm, respectively. The GlycTag was compatible with other secretion pathways such as the twin-arginine translocation (Tat) pathway as evidenced by the glycosylation of MBP and GFP targeted for Tat-dependent export (FIG. 4C). In certain aspects, glycosylation of the GlycTag on MBP is more efficient than the glycosylation of even the natural glycoprotein *C. jejuni* AcrA (FIG. 4C). Since MBP has recently been demonstrated as a model protein carrier for glycoconjugate vaccines (Fernandez et al., "Potential Role for Toll-like Receptor 4 in Mediating *Escherichia Coli* Maltose-binding Protein Activation of Dendritic Cells," *Infect Immun* 75:1359-63 (2007), which is hereby incorporated by reference in its entirety), it is envisioned that the MBP-GlycTag fusions can serve as potent glycoconjugate vaccines against the pathogenic bacterium *C. jejuni* or, as new glycan structures are generated, against other infectious agents. As many as 12 glycans per protein are possible if GlycTags are introduced to both N- and C-termini as well as inserted into permissive sites within MBP (Betton et al., "Creating a Bifunctional Protein by Insertion of Beta-lactamase into the Maltodextrin-binding Protein," *Nat Biotechnol* 15:1276-9 (1997), which is hereby incorporated by reference in its entirety). These MBP glycoconjugates would contain far more glycans than any naturally occurring glycoprotein (Ben-Dor et al., "Biases and Complex Patterns in the Residues Flanking Protein N-Glycosylation Sites," *Glycobiology* 14:95-101 (2004), which is hereby incorporated by reference in its entirety).

Example 3

IgG M18.1 Glycosylation in *E. coli*

Figures 5B, 5C:
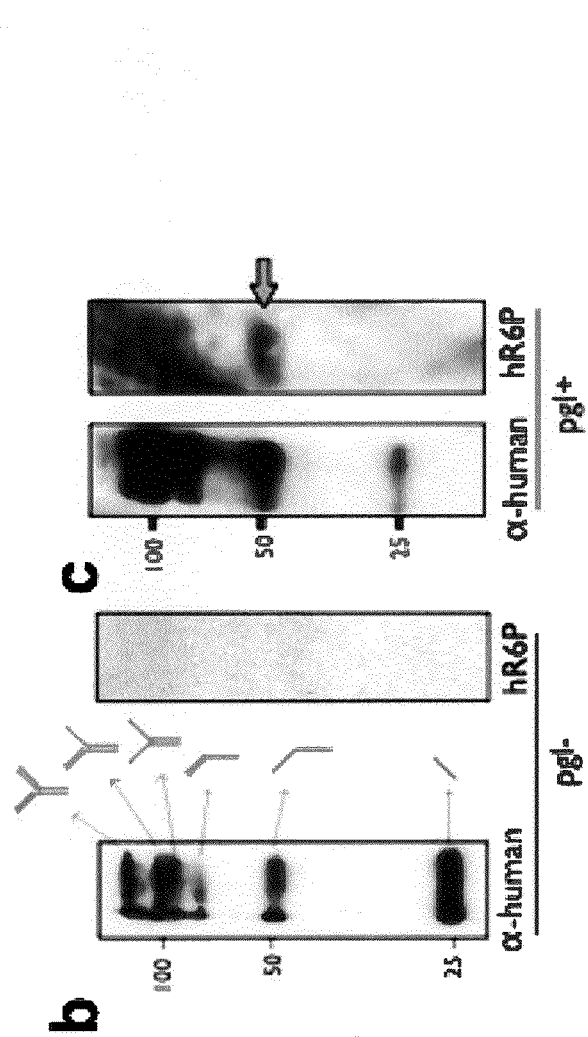

This example describes glycosylation of complex human glycoproteins in the periplasm of glyco-engineered *E. coli*. Specifically, a full-length human immunoglobulin (IgG M18.1) against anthrax toxin was expressed in pMAZ360 M18.1 (Mazor et al., "Isolation of Engineered, Full-length Antibodies from Libraries Expressed in *Escherichia coli*," *Nat Biotechnol* 25:563-5 (2007), which is hereby incorporated by reference in its entirety)) was mutated via site-directed mutagenesis (Quik Change Kit, Qiagen) such that the glutamine residue at residue 295 in the IgG heavy chain ($C_H2$) was mutated to aspartic acid to introduce the bacterial glycosylation motif D-$X_1$-N-$X_2$-S/T (FIG. 5A) using primers (5'-gacaaagccgcgggaggaggattacaacagcacgtaccgtg-3' and 5'-cacggtacgtgctgttgtaatcctcctcccgcggctttgtc-3') (SEQ ID NO:15 AND SEQ ID NO: 18, respectively). Following expression in the periplasm of BL21(DE3) *E. coli* transformed with pACYC-pgl or pACYC-pglmut (PglB W458A, D459A) (Wacker et al., "N-linked Glycosylation in *Campylobacter jejuni* and its Functional Transfer into *E. coli*," *Science* 298:1790-3 (2002), which is hereby incorporated by reference in its entirety), IgG M18.1 were purified from cell lysate via Protein A/G affinity chromatography (Nab Protein AG Spin Kit, Pierce) and subject to SDS-PAGE in non-reducing 12% SDS gels and Western blotted with detection via anti-human IgG (Promega) and hR6P antiserum raised against the bacterial heptasaccharide. A characteristic IgG banding pattern was seen for IgG M18.1 isolated from BL21 (DE3) *E. coli* transformed with pACYC-pgl or pACYC-pglmut. Only IgG M18.1 from BL21(DE3) *E. coli* transformed with pACYC-pgl cross-reacted with bacterial N-glycan specific anti-serum (hR6P). This IgG banding pattern for pgl+ and pgl– cells is seen in FIGS. 5B and 5C. However, only IgG M18.1 from pgl+ cells cross-reacted with bacterial N-glycan specific anti-serum (hR6P) (FIGS. 5B and 5C). These results indicate that human IgGs can be glycosylated in the periplasm of glyco-engineered *E. coli* cells. Accordingly, in various embodiments, the present invention provides glycosylated human IgGs produced in glyco-engineered *E. coli* cells.

Example 4

Display of N-Linked Glycoproteins on the Bacterial Cell Surface

*E. coli* BW25113 waaC:Kan transformed with pACYC-pgl (Wacker et al., "N-linked Glycosylation in *Campylobacter jejuni* and its Functional Transfer into *E. coli*," *Science* 298:1790-3 (2002), which is hereby incorporated by reference in its entirety) expressing the *C. jejuni* CjaA protein from plasmid pCjaA as an outer membrane anchor displayed the bacterial heptasaccharide on the cell surface. Plasmid pCjaA was constructed by inserting the coding region for *C. jejuni* CjaA into pBAD18 appended with the coding region for a C-terminal FLAG epitope tag. Display was detected by incubating cells with soybean agglutinin conjugated to fluorescent dye (SBA-Alexa Fluor 488 conjugate, Molecular Probes) and analyzed by flow cytometry. *E. coli* BW25113 waaC:Kan transformed with pCjaA and pACYC-pglmut (Wacker et al., "N-linked Glycosylation in *Campylobacter jejuni* and its Functional Transfer into *E. coli*," *Science* 298: 1790-3 (2002), which is hereby incorporated by reference in its entirety) or pCjaA alone, did not result in fluorescent labeling. Glycan attachment was confirmed by subjecting total cellular protein from *E. coli* BW25113 waaC:Kan expressing the *C. jejuni* CjaA protein from plasmid pCjaA transformed with either pACYC-pgl or pACYC-pglmut (Wacker et al., "N-linked Glycosylation in *Campylobacter jejuni* and its Functional Transfer into *E. coli*," *Science* 298: 1790-3 (2002), which is hereby incorporated by reference in its entirety) to Western blot analysis followed by probing with hR6P antiserum raised against the bacterial heptasaccharide.

Example 5

*E. coli* GlycoPhage Display System

Figure 8:
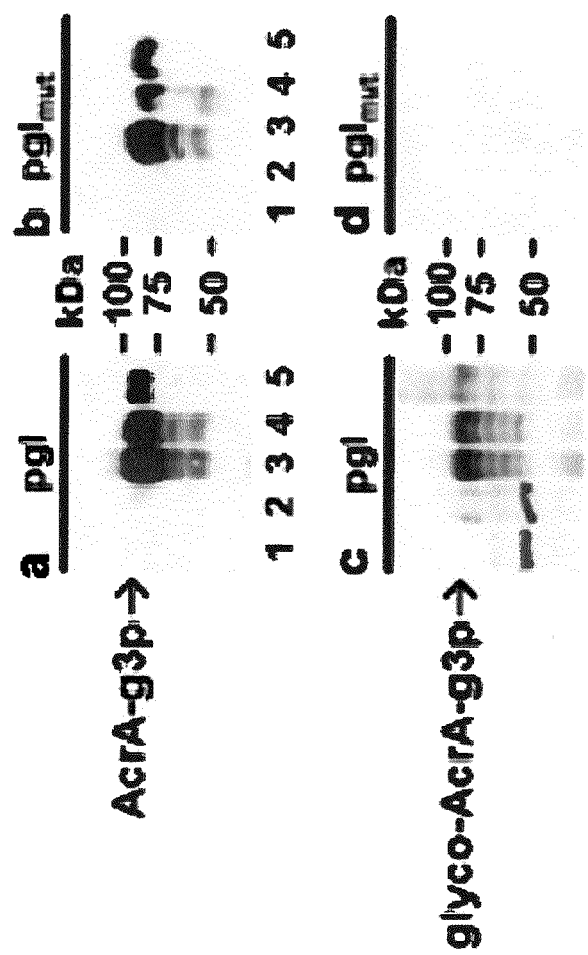
FIGS. 8A-D represent time-dependent expression and glycosylation of AcrA-g3p in pgl+ (FIGS. 8A and 8C) and pgl-mut (FIGS. 8B and 8D) cells visualized by immunodetection. Whole cell lysates were prepared from either non-induced cells (lane 1) or from cells induced with 50 mM arabinose for 1 h (lane 2), 3 h (lane 3), 5 h (lane 4), and 16 h (lane 5). Proteins were separated by 10% SDS-PAGE and transferred to a nitrocellulose membrane. AcrA-g3p and glycosylated AcrA-g3p (glyco-AcrA) were visualized with AcrA-specific antibodies (FIGS. 8A-8B) or with R12 antiserum (FIG. 8C-8D). MW markers are indicated on the right.

Expression of AcrA-g3p from phagemid pAcrA-g3p was performed in *E. coli* TG1 cells that carry either the native (pgl+) or a mutated version (pglmut) of the *C. jejuni* glycosylation locus and the appearance of AcrA-g3p was analyzed in whole cell lysates. Immunoblot analysis with AcrA-specific antiserum showed a signal in cell lysates of both TG1 pgl+ and TG1 pglmut after 3, 5 and 16 h of induction with 50 mM arabinose (FIGS. 8A and 8B, lanes 3 to 5). Anti-AcrA cross-reacting proteins with an apparent molecular mass of about 80 kDa corresponded well to the calculated mass of the AcrA-g3p fusion protein of 80.8 kDa. The same lysates were probed with glycosylation-specific antiserum (R12) that had been raised against *C. jejuni* whole cell extracts and shows a strong preference towards the glycosylated form of AcrA (Wacker et al., "N-linked Glycosylation in *Campylobacter jejuni* and its Functional Transfer into *E. coli*," *Science* 298: 1790-3 (2002), which is hereby incorporated by reference in its entirety) (FIG. 8C). Here, immunoreactive bands with a molecular mass of about 80 kDa can only be detected in whole cell lysates of TG1 pgl+ cells after 3, 5, and 16 h of induction (FIG. 8C, lanes 3 to 5). These data prove that the AcrA-g3p fusion protein was glycosylated by the *C. jejuni* pgl system.

Example 6

Time-Dependent Expression and Glycosylation of AcrA-g3p

*E. coli* TG1 expressed a fusion of *C. jejuni* AcrA to the g3p phage coat protein from a plasmid comprised of the pAra-AcrA-g3p. In pAra-Acra-g3p, the pectate lyase B signal sequence (pelB) was cloned upstream of the acrA coding sequence for Sec-dependent translocation to the periplasm of *E. coli*. Expression of the fusion protein was directed by the arabinose inducible and glucose repressible pBAD promoter. A 24-amino acid linker was juxtaposed between the expressed AcrA and the g3p domain. This linker sequence contained a hexa-histidine tag and an enterokinase cleavage site directly followed by an amber stop codon (UAG), that is transcribed as glutamine in *E. coli* supE strains (e.g., TG1). Inclusion of the phage F1 intergenic region (ori M13) on these vectors allowed for packaging of single-stranded phagemid after superinfection with helper phage. TG1 cells harboring pAra-AcrA-g3p were transformed with either pACYC-pgl or pACYC-pglmut (Wacker et al., "N-linked Glycosylation in *Campylobacter jejuni* and its Functional Transfer into *E. coli*," *Science* 298:1790-3 (2002), which is hereby incorporated by reference in its entirety) and whole cell lysates were prepared from either non-induced cells, or from cells incubated with 50 mM arabinose for 1 h, 3 h, 5 h, and 16 h. Proteins were separated by 10% SDS-PAGE with protein standards, transferred to a nitrocellulose membrane, and visualized with AcrA-specific serum or with R12 antiserum raised against the bacterial heptasaccharide.

Example 7

Quantification of Glycophage Enrichment by SBA Biopanning

Phages produced from TG1 cells harboring pAra-AcrA-g3p and either pACYC-pgl or pACYC-pglmut (Wacker et al., "N-linked Glycosylation in *Campylobacter jejuni* and its Functional Transfer into *E. coli*," *Science* 298:1790-3 (2002), which is hereby incorporated by reference in its entirety) were applied to immobilized soybean agglutinin (SBA) for column purification. The total colony forming units (CFUs) present in each fraction of the SBA panning procedure were determined by infection of fresh TG1 cells and are the means of at least three independent experiments. The number of phages subjected to SBA panning and the resulting CFUs after fresh infection varied by less than 6%. The fractions were: Fraction 1, CFUs applied to the SBA column; fraction 2, SBA flow-through; fractions 3 and 4, PBS washing steps; fraction 5, 6, and 7, washing steps with 30 mM galactose in PBS; fraction 8, 9, and 10, elution steps with 300 mM galactose in PBS. The presence of AcrA was visualized with anti-AcrA serum and the presence of the bacterial heptasaccharide was visualized with R12 antiserum raised against the bacterial glycan such that: Lane 1, raw phage preparation; lane 2, SBA flow-through; lanes 3 and 4, wash fractions with PBS; lanes 5 to 7, wash fractions with 30 mM galactose in PBS; lanes 8 to 10, elution fractions with 300 mM galactose in PBS. In lanes 1 to 4, $1 \times 10^8$ phages were applied to SDSPAGE. In lanes 5 to 10, $3.5 \times 10^7$, $1.2 \times 10^4$, $4.0 \times 10^3$, $1.3 \times 10^6$, $2.5 \times 10^6$, $1.2 \times 10^6$ phages prepared from TG1 cells harboring pAra-AcrA-g3p and pACYC-pgl or $1.5 \times 10^6$, $3.5 \times 10^3$, $3.0 \times 10^3$, $4.5 \times 10^3$, $0.5 \times 10^4$, $1.5 \times 10^3$ phages prepared from TG1 cells harboring pAra-AcrA-g3p and pACYC-pglmut were analyzed, respectively.

Figure 7:
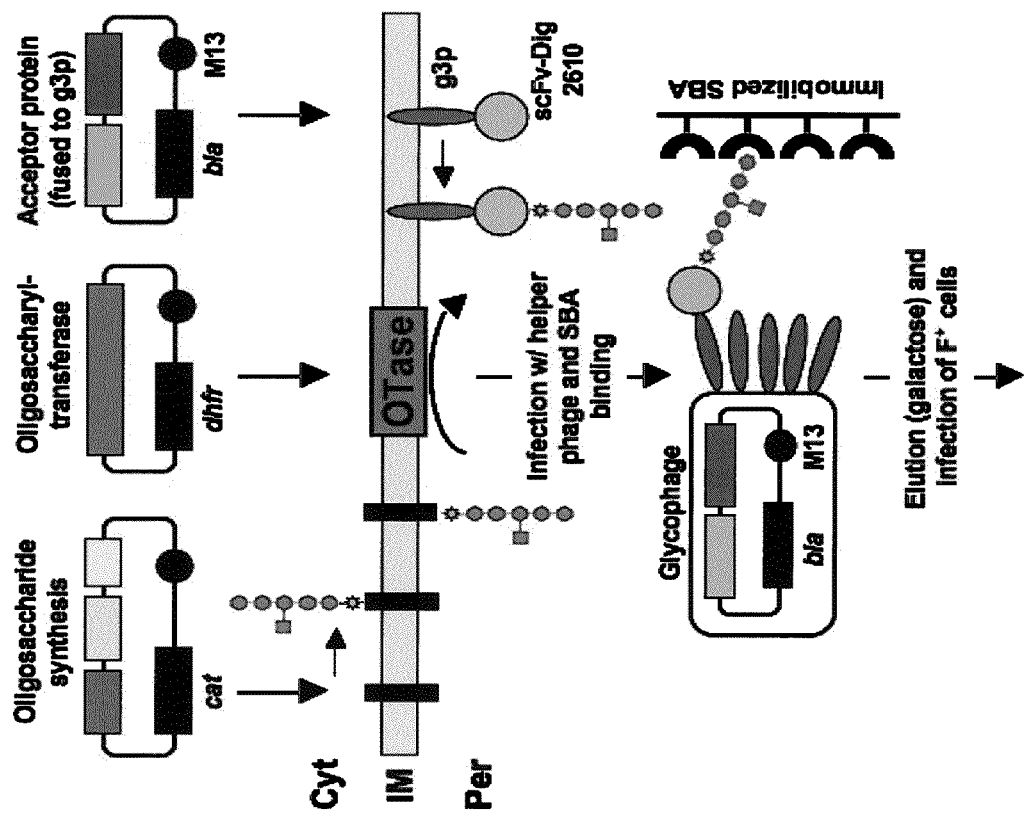
FIG. 7 is a schematic example of the glycophage system in accordance with the present invention. Plasmids or phagemids encoding the proteins for lipid linked oligosaccharide synthesis, for the oligosaccharide transfer (OTase), and for the acceptor scFv-g3p fusion protein are shown. The oligosaccharide is assembled on a lipid carrier, bactoprenylpyrophosphate, at the cytoplasmic site (Cyt) of the plasma membrane (catalyzed by individual glycosyltransferases). The oligosaccharide is then translocated across the inner membrane (IM) to the periplasmic space (Per) and transferred to specific asparagine residues of the acceptor protein by the oligosaccharyltransferase. After infection with helper phage VCSM13, phages that display the glycosylated acceptor protein (glycophage) are bound to immobilized soybean agglutinin (SBA) and eluted with galactose. Glycophages which have been eluted are used to infect *E. coli* (F+) cells selected for the antibiotic resistance present on the phagemid. The glyco-phenotype of the phage can be connected to the genotype of any of the required steps according to the presence of the on M13 and the subsequent packaging of the phagemid into phage particles. Dhfr is dihydrofolate reductase; bla is β-lactamase; cat is chloramphenicol acetyltransferase.
Figure 9A:
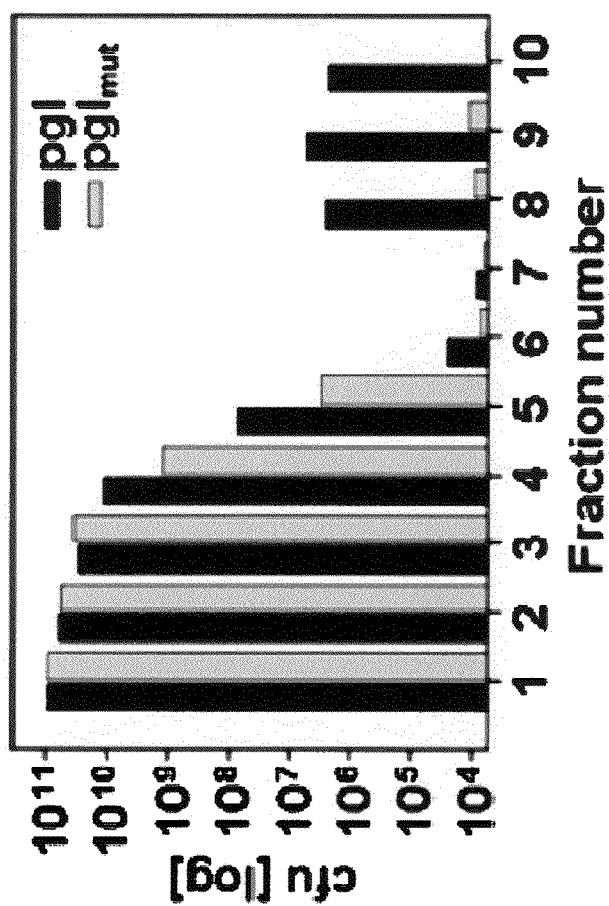
FIG. 9A shows quantification of glycophage enrichment by SBA biopanning. Phages produced from either glycosylation-competent (pgl, black bars) or glycosylation-incompetent (pglmut, grey bars) cells were applied to SBA-column purification. The values that represent the total amount of colony forming units (cfu) present within each fraction of the SBA panning procedure, as determined after infection of TG1 cells, are the means of at least three independent experiments. The amount of phages applied to SBA panning and the resulting cfus after *E. coli* infection varied by less than 6%. Fraction 1, cfu applied to the SBA column; fraction 2, SBA flow-through; fractions 3 and 4, PBS washing steps; fraction 5, 6, and 7, washing steps with 30 mM galactose in PBS; fraction 8, 9, and 10, elution steps with 300 mM galactose in PBS.
Figure 9B:
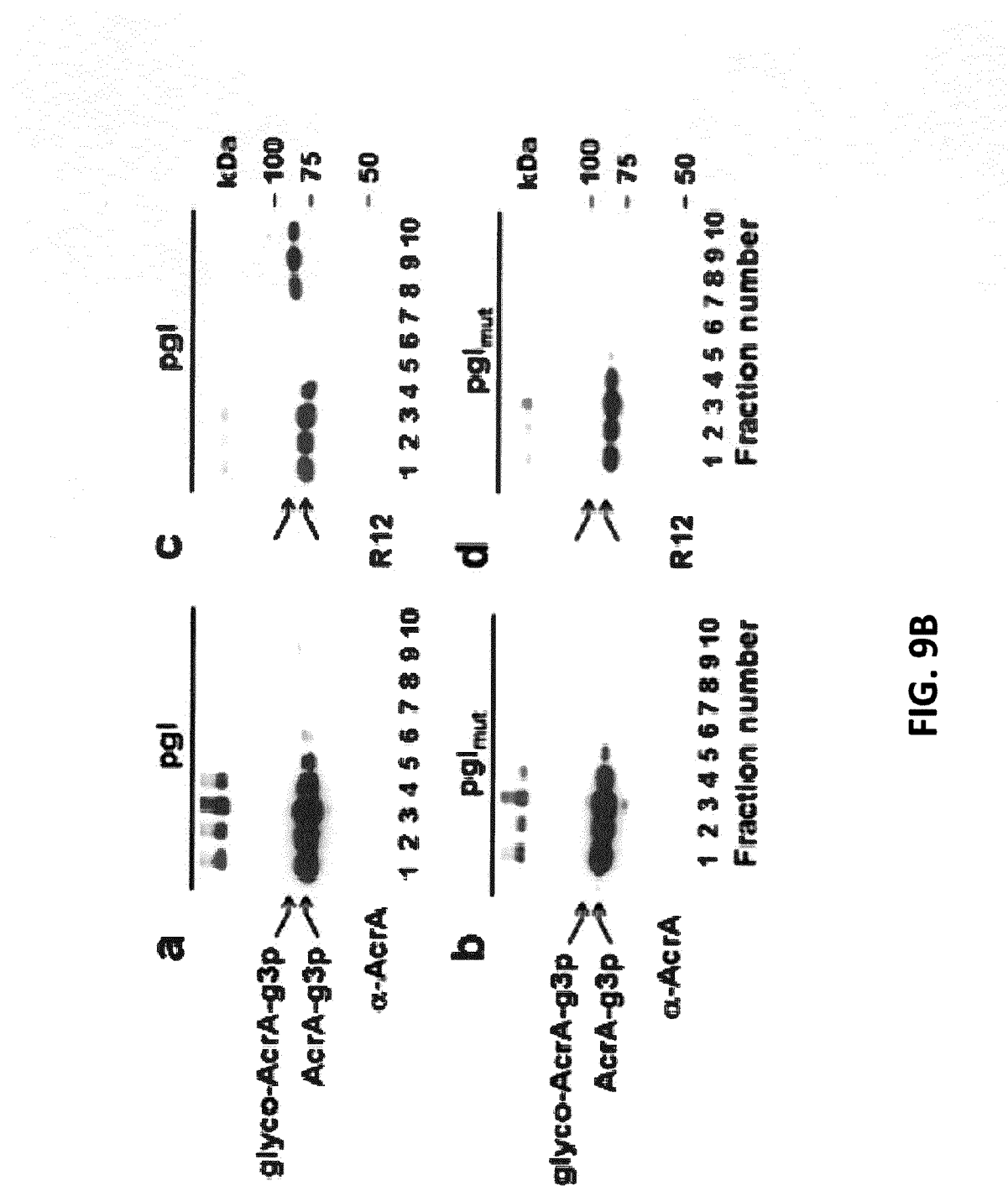
FIG. 9B is a photograph of immunodetection of AcrA-g3p and glycosylated AcrA-g3p (glyco-AcrA-g3p) displayed on phages. Phages were produced from pgl+(panels a, c) or pglmut cells (panels b, d) and applied to SBA panning. The presence of AcrA and glyco-AcrA was visualized with anti-AcrA (panels a, b) or with R12 antiserum (panels c, d). Lane 1, raw phage preparation; lane 2, SBA flow-through; lanes 3 and 4, wash fractions with PBS; lanes 5 to 7, wash fractions with 30 mM galactose in PBS; lanes 8 to 10, elution fractions with 300 mM galactose in PBS. In lanes 1 to 4, $1 \times 10^8$ phages were applied to SDS-PAGE. In lanes 5 to 10, $3.5 \times 10^7$, $1.2 \times 10^4$, $4.0 \times 10^3$, $1.3 \times 10^6$, $2.5 \times 10^6$, $1.2 \times 10^6$ phages prepared from pgl+ (panels a, c) or $1.5 \times 10^6$, $3.5 \times 10^3$, $3.0 \times 10^3$, $4.5 \times 10^3$, $0.5 \times 10^4$, $1.5 \times 10^3$ phages prepared from pglmut cells (panels b, d) were used, respectively. MW markers are indicated on the right. The amount of phages obtained by SBA panning and applied to SDS-PAGE varied by less than ±6%.

Phage titers of $<9.0 \times 10^{11}$ for TG1 pgl+ and $<8.7 \times 10^{11}$ for TG1 pglmut, each expressing pAcrA-g3p, per ml of culture supernatant were obtained. In order to determine whether glycosylated AcrA-g3p fusion protein was present in the phage preparation, an SBA bio-panning procedure was developed that allows specific enrichment of glycophages (FIG. 7). Phage preparations from TG1 pgl+ or TG1 pglmut, each expressing pAcrA-g3p, were mixed with agarose bound SBA, unbound phages were removed by successive washing steps with PBS and PBS containing 30 mM galactose. Galactose binds to SBA with an equilibrium association constant of $2 \times 10^2$ M$^{-1}$ and could therefore be used to compete with the bound oligosaccharide (Swamy et al., "Thermodynamic and Kinetic Studies on Saccharide Binding to Soya-Bean Agglutinin," *Biochem J* 234:515-22 (1986), which is hereby incorporated by reference in its entirety). Similar titers were found in the respective wash fractions for both phage preparations. In contrast, a $10^3$-fold increase in phage titer ($10^3$ to $10^6$ cfu/ml) was observed in the eluate with 300 mM galactose for phages from TG1 pgl+ expressing pAcrAg3p, while the titer stayed at the background level of $10^3$ cfu/ml for phages from TG1 pglmut expressing pAcrA-g3p (FIG. 9A). This PglB-dependent accumulation of SBA-bound phage demonstrates the production of infective glycophage and their specific enrichment by the panning procedure. Next, the presence of glycosylated AcrA-g3p fusion protein in the fractions of both SBA panning experiments was confirmed. Upon immunodetection after SDS-PAGE separation of total phage protein, a signal corresponding to AcrA-g3p was detected with AcrA-specific antibodies (FIGS. 9A and 9B, lane 1). AcrA-g3p specific bands were also present in the flow-through and in the PBS washing steps (FIGS. 9A and 9B, lanes 2, 3, and 4). A clear glycosylation-specific signal was present with the R12 antiserum in the elution fraction when phages produced from TG1 pgl+ expressing pAcrA-g3p were used for panning (FIG. 9B, panel c, lanes 8, 9, and 10). The R12 antiserum shows a high preference to the glycosylated form of AcrA but also reacts with non-glycosylated AcrA when present in high amounts (FIG. 9B, panels c and d, lanes 1 to 4). Importantly, the AcrA fusion protein detected in phage preparations eluted with high galactose concentrations (FIG. 9B, panel c, lanes 8, 9, and 10) migrates slower than the fusion protein detected in the flowthrough (FIG. 9B, panel c, lane 1), which agrees with the glycosylation of the protein. As expected, phages derived from glycosylation deficient strain TG1 pglmut expressing pAcrA-g3p did not display R12 reacting fusion protein (FIG. 9B, panel d, lanes 8, 9, and 10). Therefore, phages produced in the presence of a functional *C. jejuni* pgl operon displayed glycosylated AcrA on the surface and these glycophage were enriched by SBA panning.

To further test the specificity of this method, purified glycophage ($8 \times 10^6$ cfu) produced by TG1 (pgl+, pAcrA-g3p) was mixed with an excess (1 to $10^4$-fold) of aglycosylated phage produced by TG1 (pglmut, pAcrA-g3p) and applied to a single SBA panning step. This experimental setup allowed the differentiation between glycophage and aglycosylated phage by restriction analyses of their phagemids. Glycophage contained the amber stop codon in the AcrA-g3p expression cassette while the aglycosylated phage did not. About 96% ($7.7 \times 10^6 \pm 0.3 \times 10^6$) phages were recovered when only glycophage was applied to SBA panning. When glycophage were mixed with an equal amount or $10^2$ to $10^4$-fold excess of aglycosylated phage, an average of 96% ($7.8 \times 10^6 \pm 0.2 \times 10^6$), 93% ($7.4 \times 10^6 \pm 0.5 \times 10^6$), and 79% ($6.3 \times 10^6 \pm 1.0 \times 10^6$) of phage were bound by SBA, respectively, and subsequently found in the eluate. Applying exclusively aglycosylated phage ($8 \times 10^{10}$) significantly lowered the amount of infectious particles ($3.8 \times 10^4 \pm 0.2 \times 10^4$) that were bound to SBA. To demonstrate that phages in the elution fraction were indeed glycophage, 12 phagemids from each reconstitution were analyzed by EagI-EheI digestion that allowed the differentiation between glycophage and non-glycosylated phage. At least 11/12 phagemids showed the restriction pattern of phagemid pAcrA-g3p that was packed into glycophage produced by TG1 (pgl+, pAcrA-g3p) cells. In the elution fraction where only glycophage was used (positive control), 12/12 phagemids showed the glyco-phagemid specific DNA fragments. These data unequivocally establish that: (i) glycosylated proteins carrying the N-linked heptasaccharide are amenable to multivalent display on filamentous phage; (ii) the glycophage purification procedure works efficiently, enrichment factors as high as $10^4$ were obtained per round of SBA panning, and (iii) glycophage did not lose infectivity even when subjected to two rounds of SBA panning.

Example 8

Expression and Localization of Yeast Glycosyltransferases in *E. coli*

The generation of the $Man_3GlcNAc_2$ oligosaccharide structure requires the functional expression of several eukaryotic glycosyltransferases in *E. coli* and represents a classical example of "pathway engineering" (see FIG. 10B).

WecA-Catalyzed Transfer of First GlcNAc to Lipid Carrier.

Bactoprenylpyrophosphate serves as a carrier for the assembly of an oligosaccharide at the cytoplasmic side of the inner membrane (Feldman et al., "Engineering N-linked Protein Glycosylation With Diverse O Antigen Lipopolysaccharide Structures in *Escherichia coli*," *Proc. Nat'l Acad. Sci. USA* 102:3016-3021 (2005), which is hereby incorporated by reference in its entirety). In *E. coli*, bactoprenol-PP-GlcNAc is generated from bactoprenol-P and UDP-GlcNAc by the WecA protein (Valvano, M. A., "Export of O-specific Lipopolysaccharide," *Frontiers in Bioscience* 8:S452-S471 (2003), which is hereby incorporated by reference in its entirety). Therefore, this endogenous substrate can be used as a starting molecule in an artificial pathway that creates the $Man_3GlcNAc_2$ oligosaccharide. The reducing end GlcNAc residue is essential for the substrate recognition by eukaryotic OSTs (Tai et al., "Substrate Specificity of the Glycosyl Donor for Oligosaccharyl Transferase,"*J Org Chem* 66:6217-28 (2001), which is hereby incorporated by reference in its entirety) but also fulfills the requirements of a prokaryotic OST substrate (Wacker et al., "Substrate Specificity of Bacterial Oligosaccharyltransferase Suggests a Common Transfer Mechanism for the Bacterial and Eukaryotic Systems," *Proc. Nat'l Acad. Sci. USA* 103:7088-7093 (2006), which is hereby incorporated by reference in its entirety).

Example 9

Expression of Yeast Alg13/14 in *E. coli*

The β1,4 GlcNAc transferase for the addition of the second GlcNAc residue has recently been identified in yeast (Bickel et al., "Biosynthesis of Lipid-linked Oligosaccharides in *Saccharomyces cerevisiae*—Alg13p AND Alg14p Form a Complex Required for the Formation of GlcNAc(2)-PP-dolichol, "*J. Biol. Chem.* 280:34500-34506 (2005), which is hereby incorporated by reference in its entirety). This enzyme is a complex of two proteins, encoded by the ALG13 and the ALG14 locus from *Saccharomyces cerevisiae*. Alg14 is an integral membrane protein, whereas Alg13 is peripherally associated with the cytoplasmic side of the ER membrane by virtue of its association with Alg14. The reason for testing ΔdnaJ cells is that inactivation of dnaJ is known to increase membrane protein expression and suppress the severe cytotoxicity associated with their expression (Skretas et al., "Genetic Analysis of G Protein-coupled Receptor Expression in *Escherichia coli*: Inhibitory Role of DnaJ on the Membrane Integration of the Human Central Cannabinoid Receptor," *Biotechnol Bioeng* (2008), which is hereby incorporated by reference in its entirety).

Figure 11:
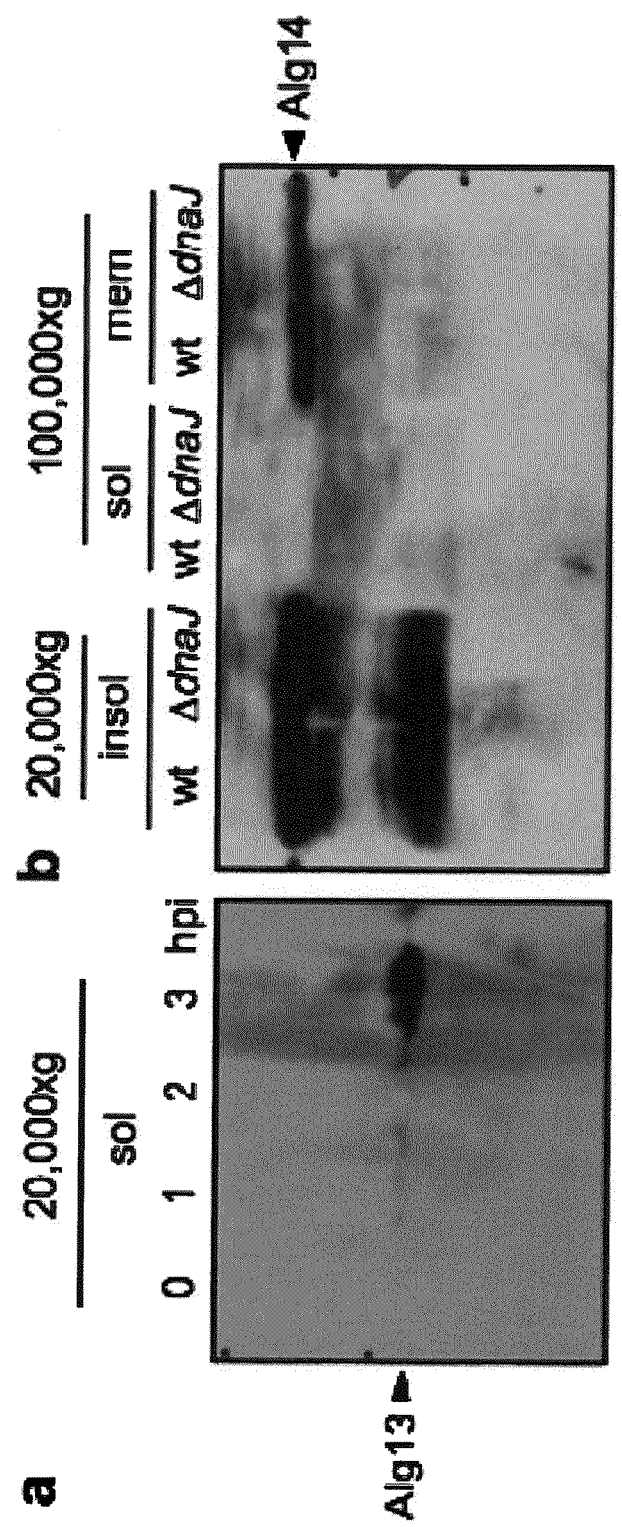
FIGS. 11A-B are photographs of Western blots, depicting expression of Alg13/14 in *E. coli*.

Total protein from MC4100 *E. coli* cells expressing Alg13 appended with a C-terminal 6×HIS tag from plasmid pBAD18-Cm. Alg14 appended with a C-terminal FLAG epitope tag was subject to centrifugation at 20,000×g for 20 mins. The supernatant represents the soluble fraction and the pellet, the insoluble fraction. The soluble fraction was further spun at 100,000×g for 1 hr and the supernatant and pellet were collected as the soluble and membrane fractions, respectively. The soluble cytoplasmic fraction collected 0, 1, 2, and 3 hrs post induction with 0.2% arabionse was probed with anti-6× HIS antibody (Promega) to detect Alg13-6×HIS. Western blot analysis was used to compare fractions isolated from MC4100 and MC4100 ΔdnaJ cells and probed with anti-FLAG antibody to detect Alg14-FLAG collected at 3 hours post induction. Soluble expression of Alg13 in the cytoplasm (FIG. 11A) and correct insertion of Alg14 in the inner membrane (FIG. 11B) were observed.

Next, GlcNAc transferase activity will be tested in extracts derived from transformed *E. coli* cells (Bickel et al., "Biosynthesis of Lipid-linked Oligosaccharides in *Saccharomyces cerevisiae*—Alg13p and Alg14p Form a Complex Required for the Formation of GlcNAc(2)-PP-dolichol," *J. Biol. Chem.* 280:34500-34506 (2005), which is hereby incorporated by reference in its entirety) and the in vivo formation of bactoprenol-PP-GlcNAc$_2$ will be analyzed by labeling the cells with $^3$H-GlcNAc and analysis of glycolipids using standard methods (Bickel et al., "Biosynthesis of Lipid-linked Oligosaccharides in *Saccharomyces cerevisiae*—Alg13p AND Alg14p Form a Complex Required for the Formation of GlcNAc(2)-PP-dolichol," *J. Biol. Chem.,* 280:34500-34506 (2005), which is hereby incorporated by reference in its entirety).

Example 10

Expression of Alg1 and Alg2 in *E. coli*

The process of the present invention further requires the expression of active Alg1 protein, the β1,4 mannosyltransferase, and bifunctional Alg2 mannosyltransferase, catalyzing the addition of both the α1,3 and α1,6 mannose residue to the oligosaccharide. Each of these enzymes has been previously expressed in an active form in *E. coli* (O'Reilly et al., "In vitro Evidence for the Dual Function of Alg2 and Alg11: Essential Mannosyltransferases in N-linked Glycoprotein Biosynthesis," *Biochemistry* 45:9593-603 (2006) and Wilson et al., "Dolichol is Not a Necessary Moiety for Lipid-linked Oligosaccharide Substrates of the Mannosyltransferases Involved in In vitro N-linked-oligosaccharide Assembly," *Biochem J* 310 (Pt 3):909-16 (1995), which are hereby incorporated by reference in their entirety)

Figure 12:
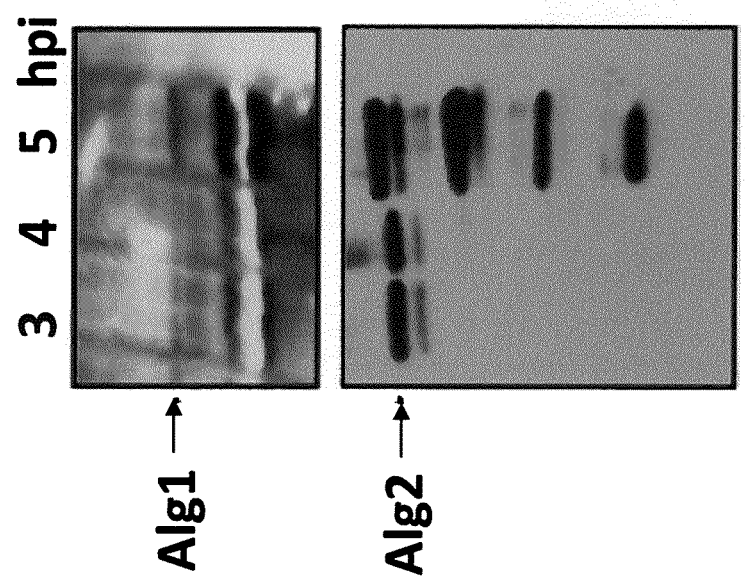
FIG. 12 is a photograph of a Western blot depicting expression of Alg1 and Alg2 in *E. coli*. These Western blots are of membrane fractions from ΔdnaJ cells harvested 3, 4, and 5 hpi. Blots were probed with anti-his antibodies.

Total protein from MC4100 ΔdnaJ *E. coli* cells expressing Alg1 and Alg2 each appended with a C-terminal 6×HIS tag and, the case of Alg2, an N-terminal thioredoxin (TrxA) solubility tag was subject to centrifugation at 20,000×g for 20 mins, the supernatant was collected and further spun at 100,000×g for 1 hr and the pellet from this spin was collected as the membrane fraction. Membrane fractions were harvested from cells at 3, 4 and 5 hours post induction. Blots were probed with anti-6×HIS antibody (Promega). As shown in FIG. 12, each localizes correctly in the inner membrane of *E. coli*.

Next, mannosyltransferase activity will need to be tested in extracts derived from transformed *E. coli* cells according to an established protocol (O'Reilly et al., "In vitro Evidence for the Dual Function of Alg2 and Alg11: Essential Mannosyltransferases in N-linked Glycoprotein Biosynthesis," *Biochemistry* 45:9593-603 (2006) and Schwarz et al., "Deficiency of GDP-Man:GlcNAc2-PP-dolichol Mannosyltransferase Causes Congenital Disorder of Glycosylation Type Ik," *Am J Hum Genet* 74:472-81 (2004), which are hereby incorporated by reference in their entirety).

Prophetic Example 11

Construction of an Artificial Alg Operon

After verification that each enzyme can be functionally expressed in E, coil, a gene cluster encoding all four of the above yeast enzymes will be constructed on a single plasmid backbone. Co-expression of the four Alg enzymes will be performed in wt, ΔdnaJ mutants, and in the strain C41(DE3) that has been previously optimized for membrane protein expression (Miroux et al., "Over-production of Proteins in *Escherichia coli*: Mutant Hosts That Allow Synthesis of Some Membrane Proteins and Globular Proteins at High Levels," *J Mol Biol* 260:289-98 (1996), which is hereby incorporated by reference in its entirety). Applicants expect that co-expression of the four Alg enzymes will result in the in vivo formation of bactoprenol-PP-GlcNAc$_2$Man$_3$. This will be confirmed by metabolic labeling cells with $^3$H-mannose for 30 min at 37° C. Bactoprenol-linked oligosaccharides will be extracted, released, and analyzed by high-performance liquid chromatography (HPLC), as described in Korner et al., "Abnormal Synthesis of Mannose 1-phosphate Derived Carbohydrates in Carbohydrate-deficient Glycoprotein Syndrome Type I Fibroblasts with Phosphomannomutase Deficiency," *Glycobiology* 8:165-71 (1998), which is hereby incorporated by reference in its entirety.

Although preferred embodiments have been depicted and described in detail herein, it will be apparent to those skilled in the relevant art that various modifications, additions, substitutions, and the like can be made without departing from the spirit of the invention and these are therefore, considered to be within the scope of the present invention as defined the claims which follow.

What is claimed:

1. A method for producing an N-linked glycosylated protein comprising:
    providing a recombinant prokaryotic host cell expressing one or more eukaryotic UDP-GlcNAc transferase enzymes, one or more eukaryotic mannosyltransferase enzymes, and a prokaryotic oligosaccharyltransferase enzyme capable of transferring a eukaryotic glycan to an N-glycosylation acceptor site of a protein, said acceptor site comprising N-X-S/T, and
    culturing said host cell under conditions effective to:
       (i) produce a eukaryotic glycan linked to a bactoprenol lipid carrier molecule, and
       (ii) transfer the eukaryotic glycan to the N-glycosylation acceptor site of the protein to produce the N-linked glycosylated protein.

2. The method of claim 1, wherein the one or more UDP-GlcNAc transferase enzymes are selected from an Alg13 enzyme, an Alg14 enzyme, or a combination thereof.

3. The method of claim 1, wherein the one or more mannosyltransferase enzymes are selected from an Alg1 enzyme, an Alg2 enzyme, or a combination thereof.

4. The method of claim 1, wherein the prokaryotic host cell further comprises a flippase activity.

5. The method of claim 1, wherein the N-linked glycosylated protein is a glycosylated antibody comprising:
    an Fv portion which binds to a native antigen and
    an Fc portion which is glycosylated at a conserved asparagine residue.

6. The method of claim 1, wherein the N-linked glycosylated protein is selected from the group consisting of erythropoietins, cytokines, interferons, G-CSF, coagulation factors, factor VIII, factor IX, human protein C, soluble IgE receptor alpha-chain, IgG, IgG fragments, IgM, interleukins, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, alpha-1 antitrypsin, DNase II, alpha-feto proteins, TNF binding protein I (rhTBP-1), transmembrane activator and calcium modulator and cyclophilin ligand interactor (TACI-Ig), follicle stimulating hormone (FSH), GM-CSF, glucagon like protein I (GLP-1), IL-1 receptor agonist, soluble TNF receptor Fc fusion (sTNFr), ATIII, rhThrombin, glucocerebrosidase, Cytotoxic T Lymphocyte associated Antigen 4-Ig (CTLA4-Ig), and serum albumin.

7. The method of claim 1, wherein the prokaryotic host cell further comprises an attenuation, disruption or deletion of competing sugar biosynthesis reactions.

8. The method of claim 1, wherein the eukaryotic glycan comprises $GlcNAc_2$.

9. The method of claim 8, wherein the eukaryotic glycan further comprises at least one mannose residue.

10. The method of claim 8, wherein the eukaryotic glycan comprises $Man_3GlcNAc_2$.

11. The method of claim 1, wherein the eukaryotic glycan is a human glycan.

* * * * *

SEQUENCE LISTING

```
<160> NUMBER OF SEQ ID NOS: 24

<210> SEQ ID NO 1
<211> LENGTH: 609
<212> TYPE: DNA
<213> ORGANISM: Saccharomyces cerevisiae

<400> SEQUENCE: 1
atgggtatta ttgaagaaaa ggctcttttt gttacgtgtg gggcaacggt gccatttcca      60
aagctcgtct catgtgtgct aagcgacgaa ttctgccaag aattgattca atatggattc     120
gtacgtctaa tcattcagtt tgggagaaac tacagttctg aatttgagca tttagtgcaa     180
gaacgcgggg gccaaagaga aagccaaaaa attccaattg accagtttgg ctgtggcgac     240
accgcaagac agtatgtcct gatgaacggg aaattaaagg tgatcgggtt tgacttttcg     300
accaagatgc aaagtattat acgtgattat tcagatttgg tcatatcaca cgctggaacg     360
ggctctatac tagattctct acggttgaat aaaccgttga tagtttgcgt aaacgattct     420
ttgatggata accaccagca gcagatagca gacaagtttg tagagttggg ctacgtatgg     480
tcttgtgcac ccactgaaac aggtttgata gctggtttac gtgcatctca aacagagaaa     540
ctcaaaccat tcccagtttc tcataacccg tcatttgagc gattgctagt tgaaactata     600
tacagctag                                                             609

<210> SEQ ID NO 2
<211> LENGTH: 609
<212> TYPE: DNA
<213> ORGANISM: Artificial
<220> FEATURE:
```

<223> OTHER INFORMATION: codon-optimized Saccharomyces cerevisiae Alg13

<400> SEQUENCE: 2

```
atgggtatca tcgaagaaaa agctctgttc gttacctgcg gtgctaccgt tccgttcccg      60
aaactggttt cttgcgttct gtctgacgaa ttctgccagg aactgatcca gtacggtttc     120
gttcgtctga tcatccagtt cggtcgtaac tactcttctg aattcgaaca cctggttcag     180
gaacgtggtg gtcagcgtga atctcagaaa atcccgatcg accagttcgg ttgcggtgac     240
accgctcgtc agtacgttct gatgaacggt aaactgaaag ttatcggttt cgacttctct     300
accaaaatgc agtctatcat ccgtgactac tctgacctgg ttatctctca cgctggtacc     360
ggttctatcc tggactctct gcgtctgaac aaaccgctga tcgtttgcgt taacgactct     420
ctgatggaca ccaccagca gcagatcgct gacaaattcg ttgaactggg ttacgtttgg     480
tcttgcgctc cgaccgaaac cggtctgatc gctggtctgc gtgcttctca gaccgaaaaa     540
ctgaaaccgt tcccggtttc tcacaacccg tctttcgaac gtctgctggt tgaaaccatc     600
tactcttaa                                                              609
```

<210> SEQ ID NO 3
<211> LENGTH: 714
<212> TYPE: DNA
<213> ORGANISM: Saccharomyces cerevisiae

<400> SEQUENCE: 3

```
atgaaaacgg cctacttggc gtcattggtg ctcatcgtat cgacagcata tgttattagg      60
ttgatagcga ttctgccttt tttccacact caagcaggta cagaaaagga tacgaaagat     120
ggagttaacc tactgaaaat acgaaaatcg tcaagaaac cgctcaagat ttttgtattc     180
ttaggatcgg gaggtcatac tggtgaaatg atccgtcttc tagaaaatta ccaggatctt     240
ttactgggta agtcgattgt gtacttgggt tattctgatg aggcttccag gcaaagattc     300
gcccacttta taaaaaaatt tggtcattgc aaagtaaaat actatgaatt catgaaagct     360
agggaagtta aagcgactct cctacaaagt gtaaagacca tcattggaac gttggtacaa     420
tcttttgtgc acgtgtttag aatcagattt gctatgtgtg ttcccctca tctgttttta     480
ttgaatgggc ctggaacatg ctgtataata tcctttggt tgaaaattat ggaacttctt     540
ttgcccctgt tgggttcctc ccatatagtt tatgtagaat cgctggcaag gattaatact     600
cctagtctga ccggaaaaat attatattgg gtagtggatg aattcattgt ccagtggcaa     660
gaattgaggg acaattattt accaagatcc aagtggttcg gcatccttgt ttaa           714
```

<210> SEQ ID NO 4
<211> LENGTH: 714
<212> TYPE: DNA
<213> ORGANISM: Artificial
<220> FEATURE:
<223> OTHER INFORMATION: codon-optimized Saccharomyces cerevisiae Alg14

<400> SEQUENCE: 4

```
atgaaaaccg cttacctggc ttctctggtt ctgatcgttt ctaccgctta cgttatccgt      60
ctgatcgcta tcctgccgtt cttccacacc caggctggta ccgaaaaaga caccaaagac     120
ggtgttaacc tgctgaaaat ccgtaaatct ctaaaaaac cgctgaaaat cttcgtttc      180
ctgggttctg gtggtcacac cggtgaaatg atccgtctgc tggaaaacta ccaggacctg     240
ctgctgggta atctatcgt ttacctgggt tactctgacg aagcttctcg tcagcgtttc     300
gctcacttca tcaaaaaatt cggtcactgc aaagttaaat actacgaatt catgaaagct     360
```

```
cgtgaagtta aagctaccct gctgcagtct gttaaaacca tcatcggtac cctggttcag    420
tctttcgttc acgttgttcg tatccgtttc gctatgtgcg ttctccgca cctgttcctg     480 ctgaacggtc cgggtacctg ctgcatcatc tctttctggc tgaaaatcat ggaactgctg    540
ctgccgctgc tgggttcttc tcacatcgtt tacgttgaat ctctggctcg tatcaacacc    600
ccgtctctga ccggtaaaat cctgtactgg gttgttgacg aattcatcgt tcagtggcag    660
gaactgcgtg acaactacct gccgcgttct aaatggttcg gtatcctggt ttaa          714

<210> SEQ ID NO 5
<211> LENGTH: 1350
<212> TYPE: DNA
<213> ORGANISM: Saccharomyces cerevisiae

<400> SEQUENCE: 5 atgttttttgg aaattcctcg gtggttactt gccttaataa tattataccct ttccataccg   60 ttagtggttt attatgttat accctacttg ttttatggca acaagtcgac caaaaaaagg    120
atcatcatat ttgtgctggg tgatgtagga cactctccaa ggatatgcta tcacgctata   180
agtttcagta agtaggttg gcaagtcgag ctatgcggtt atgtggagga cactctaccc    240
aaaattattt ccagtgatcc aaatatcacc gtccatcata tgtcaaactt gaaagaaag     300 ggaggcggaa catcagttat atttatggta agaaggtgc tttttcaagt tttaagtatt    360
ttcaaattac tttgggaatt gagaggaagc gattacatac tagttcaaaa tccaccgagc   420
atacccattc ttccgattgc tgtgctatac aagttgaccg ttgtaaact aattattgat    480 tggcacaatc tagcatattc gatattgcaa ctaaaattta aaggaaactt ttaccatcct   540
ttagtgttga tatcttacat ggtagagatg atattcagca aatttgctga ttataacttg   600
actgttactg aagcaatgag gaaatattta attcaaagct ttcacttgaa tccaaagaga   660
tgtgctgttc tctacgaccg cccggcttcc caatttcaac cttggcagg tgacatttct    720 cgtcaaaaag ccctaactac caaagccttt ataaagaatt atattcgcga tgattttgat   780
acagaaaaag gcgataaaat tattgtgact tcaacatcat tcacccctga tgaagatatt   840
ggtattttat aggtgccct aaagatttac gaaaactctt atgtcaaatt tgattcaagt   900
ttgcctaaga tcttgtgttt tataacgggt aaaggaccac taaggagaa atatatgaag   960 caagtagaag aatatgactg gaagcgctgt caaatcgaat ttgtgtggtt gtcagcagag  1020
gattacccaa agttattaca attatgcgat tacggagttt ccctgcatac ttcaagttca   1080
gggttggacc tgccaatgaa aattttagat atgtttggct caggtcttcc tgttattgca  1140
atgaactatc cagtgcttga cgaattagta caacacaatg taaatgggtt aaaatttgtt  1200
gatagaaggg agcttcatga atctctgatt tttgctatga agatgctga tttataccaa   1260 aaattgaaga aaatgtaac gcaggaagct gagaacagat ggcaatcaaa ttgggaacga  1320
acaatgagag atttgaagct aattcattga                                    1350

<210> SEQ ID NO 6
<211> LENGTH: 1350
<212> TYPE: DNA
<213> ORGANISM: Artificial
<220> FEATURE:
<223> OTHER INFORMATION: codon-optimized Saccharomyces cerevisiae Alg1

<400> SEQUENCE: 6
atgttcctgg aaatcccgcg ttggctgctg gctctgatca tcctgtacct gtctatcccg    60
```

-continued

```
ctggttgttt actacgttat cccgtacctg ttctacggta caaatctac caaaaaacgt      120
atcatcatct tcgttctggg tgacgttggt cactctccgc gtatctgcta ccacgctatc     180
tctttctcta aactgggttg gcaggttgaa ctgtgcggtt acgttgaaga caccctgccg     240
aaaatcatct cttctgaccc gaacatcacc gttcaccaca tgtctaacct gaaacgtaaa     300
ggtggtggta cctctgttat cttcatggtt aaaaaagttc tgttccaggt tctgtctatc     360
ttcaaactgc tgtgggaact gcgtggttct gactacatcc tggttcagaa cccgccgtct    420
atcccgatcc tgccgatcgc tgttctgtac aaactgaccg gttgcaaact gatcatcgac     480
tggcacaacc tggcttactc tatcctgcag ctgaaattca aggtaacttc taccacccg      540
ctggttctga tctcttacat ggttgaaatg atcttctcta aattcgctga ctacaacctg     600
accgttaccg aagctatgcg taaatacctg atccagtctt tccacctgaa cccgaaacgt     660
tgcgctgttc tgtacgaccg tccggcttct cagttccagc cgctggctgg tgacatctct     720
cgtcagaaag ctctgaccac caaagctttc atcaaaaact acatccgtga cgacttcgac     780
accgaaaaag gtgacaaaat catcgttacc tctacctctt tcaccccgga cgaagacatc     840
ggtatcctgc tgggtgctct gaaaatctac gaaaactctt acgttaaatt cgactcttct     900
ctgccgaaaa tcctgtgctt catcaccggt aaaggtccgc tgaaagaaaa atacatgaaa     960
caggttgaag aatacgactg gaaacgttgc cagatcgaat tcgtttggct gtctgctgaa    1020
gactacccga aactgctgca gctgtgcgac tacggtgttt ctctgcacac ctcttcttct    1080
ggtctggacc tgccgatgaa aatcctggac atgttcggtt ctggtctgcc ggttatcgct    1140
atgaactacc cggttctgga cgaactggtt cagcacaacg ttaacggtct gaaattcgtt    1200
gaccgtcgtg aactgcacga atctctgatc ttcgctatga agacgctga cctgtaccag     1260
aaactgaaaa aaacgttac ccaggaagct gaaaaccgtt ggcagtctaa ctgggaacgt    1320
accatgcgtg acctgaaact gatccactaa                                     1350
```

<210> SEQ ID NO 7
<211> LENGTH: 1512
<212> TYPE: DNA
<213> ORGANISM: Saccharomyces cerevisiae

<400> SEQUENCE: 7

```
atgattgaaa aggataaaag aacgattgct tttattcatc cagacctagg tattgggggc      60
gctgaaaggt tagtcgtcga tgcagcatta ggtctacagc aacaaggaca tagtgtaatc     120
atctatacta gtcactgtga taatcacat tgtttcgaag aagttaaaaa cggccaatta     180
aaagtcgaag tttatggtga ttttttaccg acaaactttt tgggtcgttt ttttattgtt     240
ttcgcaacaa ttagacagct ttatttagtt attcaattga tcctacagaa aaaagtgaat    300
gcgtaccaat taattatcat tgatcaactg tctacatgta ttccgcttct gcatatcttt     360
agttctgcca ctttgatgtt ttattgtcat ttccccgacc aattattggc tcaaagagct    420
gggctattga agaaaatata cagactacca tttgacttaa tagaacagtt ttccgtgagt     480
gctgccgata ctgttgtggt aaattcaaat ttcactaaga atacgttcca ccaaacgttc     540
aagtatttat ccaatgatcc agacgtcatt tatccatgcg tggatttatc aacaatcgaa    600
attgaagata ttgacaagaa atttttcaaa acagtgttta acgaaggcga tagattttac     660
ctaagtataa atcgtttttga gaaaaaaaag gatgttgcgc tggctataaa ggcttttgcg    720
ttatctgaag atcaaatcaa tgacaacgtt aagttagtta tttgcggtgg ttatgacgag    780
agggttgcag aaaatgtgga gtacttgaag gaactacagt ctctggccga tgaatacgaa    840
```

```
ttatcccata caaccatata ctaccaagaa ataaagcgcg tctccgattt agagtcattc    900
aaaaccaata atagtaaaat tatatttta acttccattt catcatctct gaaagaatta     960
ctgctcgaaa gaaccgaaat gttattgtat acaccagcat atgagcactt tggtattgtt   1020
cctttagaag ccatgaaatt aggtaagcct gtactagcag taaacaatgg aggtcctttg   1080
gagactatca aatcttacgt tgctggtgaa aatgaaagtt ctgccactgg gtggctaaaa   1140
cctgccgtcc ctattcaatg ggctactgca attgatgaaa gcagaaagat cttgcagaac   1200
ggttctgtga actttgagag gaatggcccg ctaagagtca gaaatactt ttctagggaa    1260 gcaatgactc agtcatttga agaaaacgtc gagaaagtca tatggaaaga aaaaaagtat   1320
tatccttggg aaatattcgg tatttcattc tctaatttta ttttgcatat ggcatttata   1380
aaaattctac ccaataatcc atggcccttc ctatttatgg ccactttat ggtattatat    1440 tttaagaact acttatgggg aatttactgg gcatttgtat tcgctctctc ctacccttat   1500
gaagaaatat aa                                                       1512

<210> SEQ ID NO 8
<211> LENGTH: 1512
<212> TYPE: DNA
<213> ORGANISM: Artificial
<220> FEATURE:
<223> OTHER INFORMATION: codon-optimized Saccharomyces cerevisiae Alg2

<400> SEQUENCE: 8
atgatcgaaa agacaaacg taccatcgct ttcatccacc cggacctggg tatcggtggt      60
gctgaacgtc tggttgttga cgctgctctg gtctgcagc agcagggtca ctctgttatc     120
atctacacct ctcactgcga caatctcac tgcttcgaag aagttaaaaa cggtcagctg     180
aaagttgaag tttacggtga cttcctgccg accaacttcc tgggtcgttt cttcatcgtt   240
ttcgctacca tccgtcagct gtacctggtt atccagctga cctgcagaa aaaagttaac    300 gcttaccagc tgatcatcat cgaccagctg tctacctgca tcccgctgct gcacatcttc   360
tcttctgcta ccctgatgtt ctactgccac ttcccggacc agctgctggc tcagcgtgct   420
ggtctgctga aaaaaatcta ccgtctgccg ttcgacctga tcaacagtt ctctgttttct    480 gctgctgaca ccgttgttgt taactctaac ttcaccaaaa acaccttcca ccagaccttc   540
aaatacctgt ctaacgaccc ggacgttatc tacccgtgcg ttgacctgtc taccatcgaa   600
atcgaagaca tcgacaaaaa attcttcaaa accgttttca cgaaggtga ccgtttctac    660 ctgtctatca accgtttcga aaaaaaaaaa gacgttgctc tggctatcaa gctttcgct    720 ctgtctgaag accagatcaa cgacaacgtt aaactggtta ctgcggtgg ttacgacgaa   780 cgtgttgctg aaaacgttga atacctgaaa gaactgcagt ctctggctga cgaatacgaa   840
ctgtctcaca ccaccatcta ctaccaggaa atcaaacgtg tttctgaccct ggaatctttc   900 aaaaccaaca actctaaaat catcttcctg acctctatct cttcttctct gaagaactg    960 ctgctggaac gtaccgaaat gctgctgtac accccggctt acgaacactt cggtatcgtt   1020
ccgctggaag ctatgaaact gggtaaaccg ttctggctg ttaacaacgg tggtcctgctg   1080 gaaccatca aatcttacgt tgctggtgaa acgaatctt ctgctaccgg ttggctgaaa    1140
ccggctgttc cgatccagtg ggctaccgct atcgacgaat ctcgtaaaat cctgcagaac   1200
ggttctgtta acttcgaacg taacggtccg ctgcgtgtta aaaatactt ctctcgtgaa    1260 gctatgaccc agtctttcga agaaaacgtt gaaaagtta tctggaaaga aaaaaaatac   1320
```

-continued

```
tacccgtggg aaatcttcgg tatctctttc tctaacttca tcctgcacat ggctttcatc    1380
aaaatcctgc cgaacaaccc gtggccgttc ctgttcatgg ctaccttcat ggttctgtac    1440
ttcaaaaact acctgtgggg tatctactgg gctttcgttt tcgctctgtc ttacccgtac    1500
gaagaaatct aa                                                        1512
```

<210> SEQ ID NO 9
<211> LENGTH: 1725
<212> TYPE: DNA
<213> ORGANISM: Saccharomyces cerevisiae

<400> SEQUENCE: 9

```
atggcgaaaa aaaactcaca attgccctct actagtgagc agatcttgga aaggtccaca     60
acaggagcta ccttcctcat gatgggccaa ctttttcacca aactggtaac gttcatacta    120
aataatttgt tgatcaggtt tctgtcgccc agaattttcg gtatcacggc ctttctagaa    180
tttatacagg gcacagtgtt attttttagc agagatgcga ttcgtctgtc gacgttgaga    240
atctcagact ccggtaatgg aataatcgat gatgacgacg aggaggagta ccaggaaact    300
cattacaagt ctaaagtttt gcaaaccgca gtcaattttg cttacattcc gttttggatc    360
gggtttccac tgtccattgg tcttatcgcc tggcagtaca gaaacatcaa cgcgtatttc    420
atcactcttc cattcttcag gtggtcgatt tttcttatct ggctgagtat catcgtggag    480
ctgttaagcg agccattctt catcgtcaac cagtttatgt tgaactatgc cgcaaggtca    540
agatttgaaa gcatcgcggt gactacagga tgtattgtca attttatagt tgtttatgcc    600
gttcagcaat cccgctaccc aatgggggtt gtcacatcgg acattgacaa agaaggcatc    660
gccatattgg catttgcctt gggaaagtta gcacattcga tcaccctgct agcatgttac    720
tactgggact atctcaagaa tttcaaacca agaaattgt tcagtaccag gctaacgaag    780
ataaaaacgc gtgaaaataa cgaattgaag aaaggctacc caaagagcac atcttatttt    840
ttccaaaacg acattttaca gcacttcaaa aaagtttatt ttcaactatg ttttaagcat    900
ttgttgacag agggtgataa gttgattatc aattctttat gtactgtgga agaacaaggc    960
atttacgctc tattgtcgaa ctatggatcg ctactaacaa gattattatt tgcgccgatc    1020
gaagaatctc tgcggttatt tttggcccgt ttattatcct cgcataaccc taaaaattta    1080
aaactatcta ttgaagtcct ggtgaattta acaaggtttt acatatactt atcgttaatg    1140
atcattgtat ttgggcctgc caattcatcc tttttattgc agttcttgat ggctcgaaaa    1200
tggtccacta cttccgtttt ggacactata agagtctact gcttttacat cccattttta    1260
tcgcttaatg gtattttga agcttttttc cagagtgtag ccactggtga ccaaattttg    1320
aaacattcat attttatgat ggcctttcct ggtattttcc tgctcaattc ctggcttctt    1380
attgaaaaac tcaaactatc aatcgaaggc ttgatattga gtaacatcat taacatggtg    1440
ttgagaatat tgtattgtgg agttttcttg aataaatttc atagggaact gtttacagat    1500
tcctcttttt tcttcaattt taaggatttc aaaacagtta ttattgctgg ctcaacgatc    1560
tgtctacttg actggtggtt tattgggtac gttaaaaatt tacaacaatt tgttgttaac    1620
gtattattcg caatgggatt gttagcgtta atttttggtca aggagcgcca aaccatacaa    1680
tcttttatta acaagagggc ggtttccaat tctaaagatg tataa                    1725
```

<210> SEQ ID NO 10
<211> LENGTH: 1725
<212> TYPE: DNA
<213> ORGANISM: Artificial
<220> FEATURE:
<223> OTHER INFORMATION: codon-optimized Saccharomyces cerevisiae Rft1

<400> SEQUENCE: 10

```
atggctaaaa aaaactctca gctgccgtct acctctgaac agatcctgga acgttctacc      60
accggtgcta ccttcctgat gatgggtcag ctgttcacca aactggttac cttcatcctg     120
aacaacctgc tgatccgttt cctgtctccg cgtatcttcg gtatcaccgc tttcctggaa     180
ttcatccagg gtaccgttct gttcttctct cgtgacgcta ccgtctgtc tacccctgcgt     240
atctctgact ctggtaacgg tatcatcgac gacgacgacg aagaagaata ccaggaaacc     300
cactacaaat ctaaagttct gcagaccgct gttaacttcg cttacatccc gttctggatc     360
ggtttcccgc tgtctatcgg tctgatcgct tggcagtacc gtaacatcaa cgcttacttc     420
atcaccctgc cgttcttccg ttggtctatc ttcctgatct ggctgtctat catcgttgaa     480
ctgctgtctg aaccgttctt catcgttaac cagttcatgc tgaactacgc tgctcgttct     540
cgtttcgaat ctatcgctgt taccaccggt tgcatcgtta acttcatcgt tgtttacgct     600
gttcagcagt ctcgttaccc gatgggtgtt gttacctctg acatcgacaa agaaggtatc     660
gctatcctgg cttttcgctct gggtaaactg gctcactcta tcaccctgct ggcttgctac     720
tactgggact acctgaaaaa cttcaaaccg aaaaaactgt ctctacccg tctgaccaaa     780
atcaaaaccc gtgaaaacaa cgaactgaaa aaggttacc cgaaatctac ctcttacttc     840
ttccagaacg acatcctgca gcacttcaaa aagtttact tccagctgtg cttcaaacac     900
ctgctgaccg aaggtgacaa actgatcatc aactctctgt gcaccgttga agaacagggt     960
atctacgctc tgctgtctaa ctacggttct ctgctgaccc gtctgctgtt cgctccgatc    1020
gaagaatctc tgcgtctgtt cctggctcgt ctgctgtctt ctcacaaccc gaaaaacctg    1080
aaactgtcta tcgaagttct ggttaacctg accgtttct acatctacct gtctctgatg    1140
atcatcgttt tcggtccggc taactcttct ttcctgctgc agttcctgat cggttctaaa    1200
tggtctacca cctctgttct ggacaccatc cgtgtttact gcttctacat cccgttcctg    1260
tctctgaacg gtatcttcga agctttcttc cagtctgttg ctaccggtga ccagatcctg    1320
aaacactctt acttcatgat ggcttttctct ggtatcttcc tgctgaactc ttggctgctg    1380
atcgaaaaac tgaaactgtc tatcgaaggt ctgatcctgt ctaacatcat caacatggtt    1440
ctgcgtatcc tgtactgcgg tgttttcctg aacaaattcc accgtgaact gttcaccgac    1500
tcttcttttct tcttcaactt caaagacttc aaaaccgtta tcatcgctgg ttctaccatc    1560
tgcctgctgg actggtggtt catcggttac gttaaaaacc tgcagcagtt cgttgttaac    1620
gttctgttcg ctatgggtct gctggctctg atcctggtta agaacgtca gaccatccag    1680
tctttcatca caaacgtgc tgtttctaac tctaaagacg tttaa                     1725
```

<210> SEQ ID NO 11
<211> LENGTH: 2157
<212> TYPE: DNA
<213> ORGANISM: Saccharomyces cerevisiae

<400> SEQUENCE: 11

```
atgggatccg accggtcgtg tgttttgtct gtgtttcaga ccatcctcaa gctcgtcatc      60
ttcgtggcga ttttttgggc tgccatatca tcacgtttgt ttgcagtcat caaatttgag     120
tctattatcc atgaattcga cccctggttc aattataggg ctaccaaata tctcgtcaac     180
aattcgtttt acaagttttt gaactggttt gacgaccgta cctggtaccc cctcggaagg     240
```

```
gttactggag ggactttata tcctggtttg atgacgacta gtgcgttcat ctggcacgcc      300
ctgcgcaact ggttgggctt gcccattgac atcagaaacg tttgtgtgct atttgcgcca      360
ctattttctg gggtcaccgc ctgggcgact tacgaattta cgaaagagat taaagatgcc      420
agcgctgggc ttttggctgc tggttttata gccattgtcc ccggttatat atctagatca      480 gtggcgggt cctacgataa tgaggccatt gccattacac tattaatggt cactttcatg      540
ttttggatta aggcccaaaa gactggctct atcatgcacg caacgtgtgc agctttattc      600
tacttctaca tggtgtcggc ttggggtgga tacgtgttca tcaccaactt gatcccactc      660
catgtctttt tgctgatttt gatgggcaga tattcgtcca aactgtattc tgcctacacc      720
acttggtacg ctattggaac tgttgcatcc atgcagatcc catttgtcgg tttcctacct      780
atcaggtcta acgaccacat ggccgcattg ggtgttttcg gtttgattca gattgtcgcc      840
ttcggtgact tcgtgaaggg ccaaatcagc acagctaagt ttaaagtcat catgatggtt      900
tctctgtttt tgatcttggt ccttggtgtg gtcggacttt ctgccttgac ctatatgggg      960
ttgattgccc cttggactgg tagatttat tcgttatggg ataccaacta cgcaaagatc     1020
cacattccta tcattgcctc cgtttccgaa catcaacccg tttcgtggcc cgctttcttc     1080
tttgataccc acttttgat ctggctattc cccgccggtg tattcctact attcctcgac     1140
ttgaaagacg agcacgtttt tgtcatcgct tactccgttc tgtgttcgta ctttgccggt     1200
gttatggtta gattgatgtt gactttgaca ccagtcatct gtgtgtccgc cgccgtcgca     1260
ttgtccaaga tatttgacat ctacctggat ttcaagacaa gtgaccgcaa atacgccatc     1320
aaacctgcgg cactactggc caaattgatt gtttccggat cattcatctt ttatttgtat     1380
cttttcgtct tccattctac ttgggtaaca agaactgcat actcttctcc ttctgttgtt     1440
ttgccatcac aaaccccaga tggtaaattg gcgttgatcg acgacttcag ggaagcgtac     1500
tattggttaa gaatgaactc tgatgaggac agtaaggttg cagcgtggtg ggattacggt     1560
taccaaattg gtggcatggc agacagaacc acttttagtcg ataacaacac gtggaacaat     1620
actcacatcg ccatcgttgg taaagccatg gcttcccctg aagagaaatc ttacgaaatt     1680
ctaaaagagc atgatgtcga ttatgtcttg gtcatctttg gtggtctaat tgggtttggt     1740
ggtgatgaca tcaacaaatt cttgtggatg atcagaatta gcgagggaat ctggccagaa     1800
gagataaaag agcgtgattt ctataccgca gagggagaat acagagtaga tgcaagggct     1860
tctgagacca tgaggaactc gctactttac aagatgtcct acaaagattt cccacaatta     1920
ttcaatggtg gccaagccac tgacagagtg cgtcaacaaa tgatcacacc attagacgtc     1980
ccaccattag actacttcga cgaagttttt acttccgaaa actggatggt tagaatatat     2040
caattgaaga aggatgatgc ccaaggtaga actttgaggg acgttggtga gttaaccagg     2100
tcttctacga aaaccagaag gtccataaag agacctgaat taggcttgag agtctaa       2157

<210> SEQ ID NO 12
<211> LENGTH: 2157
<212> TYPE: DNA
<213> ORGANISM: Artificial
<220> FEATURE:
<223> OTHER INFORMATION: codon-optimized Saccharomyces cerevisiae STT3

<400> SEQUENCE: 12
atgggttctg accgttcttg cgttctgtct gttttccaga ccatcctgaa actggttatc       60
ttcgttgcta tcttcggtgc tgctatctct tctcgtctgt tcgctgttat caaattcgaa      120
tctatcatcc acgaattcga cccgtggttc aactaccgtg ctaccaaata cctggttaac      180
```

```
aactctttct acaaattcct gaactggttc gacgaccgta cctggtaccc gctgggtcgt        240
gttaccggtg gtaccctgta cccgggtctg atgaccacct ctgctttcat ctggcacgct        300
ctgcgtaact ggctgggtct gccgatcgac atccgtaacg tttgcgttct gttcgctccg        360
ctgttctctg gtgttaccgc ttgggctacc tacgaattca ccaaagaaat caaagacgct        420
tctgctggtc tgctggctgc tggtttcatc gctatcgttc cgggttacat ctctcgttct        480
gttgctggtt cttacgacaa cgaagctatc gctatcaccc tgctgatggt taccttcatg        540
ttctggatca aagctcagaa accggttct atcatgcacg ctacctgcgc tgctctgttc        600
tacttctaca tggtttctgc ttggggtggt tacgttttca tcaccaacct gatcccgctg        660
cacgttttcc tgctgatcct gatgggtcgt tactcttcta aactgtactc tgcttacacc        720
acctggtacg ctatcggtac cgttgcttct atgcagatcc cgttcgttgg tttcctgccg        780
atccgttcta acgaccacat ggctgctctg gtgttttcg gtctgatcca gatcgttgct        840
ttcggtgact cgttaaagg tcagatctct accgctaaat caaagttat catgatggtt        900 tctctgttcc tgatcctggt tctgggtgtt gttggtctgt ctgctctgac tacatgggt         960 ctgatcgctc cgtggaccgg tcgtttctac tctctgtggg acaccaacta cgctaaaatc       1020
cacatcccga tcatcgcttc tgtttctgaa caccagccgg tttcttggcc ggctttcttc       1080
ttcgacaccc acttcctgat ctggctgttc ccggctggtg ttttcctgct gttcctggac       1140
ctgaaagacg aacacgtttt cgttatcgct tactctgttc tgtgctctta cttcgctggt       1200
gttatggttc gtctgatgct gaccctgacc ccggttatct gcgtttctgc tgctgttgct       1260
ctgtctaaaa tcttcgacat ctacctggac ttcaaaacct ctgaccgtaa atacgctatc       1320
aaaccggctg ctctgctggc taaactgatc gtttctggtt ctttcatctt ctacctgtac       1380
ctgttcgttt tccactctac ctgggttacc cgtaccgctt actcttctcc gtctgttgtt       1440
ctgccgtctc agaccccgga cggtaaactg ctctgatcg acgacttccg tgaagcttac       1500
tactggctgc gtatgaactc tgacgaagac tctaaagttg ctgcttggtg ggactacggt       1560
taccagatcg gtggtatggc tgaccgtacc accctggttg acaacaacac ctggaacaac       1620
acccacatcg ctatcgttgg taaagctatg gcttctccgg aagaaaaatc ttacgaaatc       1680
ctgaaagaac acgacgttga ctacgttctg gttatcttcg gtggtctgat cggtttcggt       1740
ggtgacgaca tcaacaaatt cctgtggatg atccgtatct ctgaaggtat ctggccggaa       1800
gaaatcaaag aacgtgactt ctacaccgct gaaggtgaat accgtgttga cgctcgtgct       1860
tctgaaacca tgcgtaactc tctgctgtac aaaatgtctt acaaagactt cccgcagctg       1920
ttcaacggtg tcaggctac cgaccgtgtt cgtcagcaga tgatcacccc gctggacgtt       1980
ccgccgctgg actacttcga cgaagttttc acctctgaaa actggatggt tcgtatctac       2040
cagctgaaaa aagacgacgc tcagggtcgt accctgcgtg acgttggtga actgacccgt       2100
tcttctacca aaacccgtcg ttctatcaaa cgtccggaac tgggtctgcg tgtttaa         2157
```

<210> SEQ ID NO 13
<211> LENGTH: 78
<212> TYPE: DNA
<213> ORGANISM: Artificial
<220> FEATURE:
<223> OTHER INFORMATION: glycosylation tag

<400> SEQUENCE: 13

```
gatcagaacg cgaccggcgg tgaccaaaat gccacaggtg gcgatcaaaa cgccaccggc         60
```
ggtgaccaga atgcgaca                                                        78

<210> SEQ ID NO 14
<211> LENGTH: 5
<212> TYPE: PRT
<213> ORGANISM: Artificial
<220> FEATURE:
<223> OTHER INFORMATION: glycosylation motif

<400> SEQUENCE: 14

Asp Gln Asn Ala Thr
1               5

<210> SEQ ID NO 15
<211> LENGTH: 41
<212> TYPE: DNA
<213> ORGANISM: Artificial
<220> FEATURE:
<223> OTHER INFORMATION: primer

<400> SEQUENCE: 15
gacaaagccg cgggaggagg attacaacag cacgtaccgt g                              41

<210> SEQ ID NO 16
<211> LENGTH: 30
<212> TYPE: PRT
<213> ORGANISM: Artificial
<220> FEATURE:
<223> OTHER INFORMATION: glycosylation tag
<220> FEATURE:
<221> NAME/KEY: PEPTIDE
<222> LOCATION: (4)..(4)
<223> OTHER INFORMATION: X at position 4 is any amino acid other than
      proline
<220> FEATURE:
<221> NAME/KEY: PEPTIDE
<222> LOCATION: (6)..(6)
<223> OTHER INFORMATION: X at position 6 is any amino acid other than
      proline
<220> FEATURE:
<221> NAME/KEY: PEPTIDE
<222> LOCATION: (11)..(11)
<223> OTHER INFORMATION: X at position 11 is any amino acid other than
      proline
<220> FEATURE:
<221> NAME/KEY: PEPTIDE
<222> LOCATION: (13)..(13)
<223> OTHER INFORMATION: X at position 13 is any amino acid other than
      proline
<220> FEATURE:
<221> NAME/KEY: PEPTIDE
<222> LOCATION: (18)..(18)
<223> OTHER INFORMATION: X at position 18 is any amino acid other than
      proline
<220> FEATURE:
<221> NAME/KEY: PEPTIDE
<222> LOCATION: (20)..(20)
<223> OTHER INFORMATION: X at position 20 is any amino acid other than
      proline
<220> FEATURE:
<221> NAME/KEY: PEPTIDE
<222> LOCATION: (25)..(25)
<223> OTHER INFORMATION: X at position 25 is any amino acid other than
      proline
<220> FEATURE:
<221> NAME/KEY: PEPTIDE
<222> LOCATION: (27)..(27)
<223> OTHER INFORMATION: X at position 27 is any amino acid other than
      proline

<400> SEQUENCE: 16

Leu Glu Asp Xaa Asn Xaa Thr Gly Gly Asp Xaa Asn Xaa Thr Gly Gly
1               5                   10                  15

```
Asp Xaa Asn Xaa Thr Gly Gly Asp Xaa Asn Xaa Thr Val Asp
            20                  25                  30
```

<210> SEQ ID NO 17
<211> LENGTH: 5
<212> TYPE: PRT
<213> ORGANISM: Artificial
<220> FEATURE:
<223> OTHER INFORMATION: glycosylation motif
<220> FEATURE:
<221> NAME/KEY: PEPTIDE
<222> LOCATION: (2)..(2)
<223> OTHER INFORMATION: X at position 2 is any amino acid other than
      proline
<220> FEATURE:
<221> NAME/KEY: PEPTIDE
<222> LOCATION: (4)..(4)
<223> OTHER INFORMATION: X at position 4 is any amino acid other than
      proline

<400> SEQUENCE: 17

```
Asp Xaa Asn Xaa Thr
1               5
```

<210> SEQ ID NO 18
<211> LENGTH: 41
<212> TYPE: DNA
<213> ORGANISM: Artificial
<220> FEATURE:
<223> OTHER INFORMATION: primer

<400> SEQUENCE: 18
cacggtacgt gctgttgtaa tcctcctccc gcggctttgt c                           41

<210> SEQ ID NO 19
<211> LENGTH: 449
<212> TYPE: PRT
<213> ORGANISM: Saccharomyces cerevisiae

<400> SEQUENCE: 19

```
Met Phe Leu Glu Ile Pro Arg Trp Leu Leu Ala Leu Ile Ile Leu Tyr
1               5                   10                  15

Leu Ser Ile Pro Leu Val Val Tyr Tyr Val Ile Pro Tyr Leu Phe Tyr
                20                  25                  30

Gly Asn Lys Ser Thr Lys Lys Arg Ile Ile Ile Phe Val Leu Gly Asp
            35                  40                  45

Val Gly His Ser Pro Arg Ile Cys Tyr His Ala Ile Ser Phe Ser Lys
        50                  55                  60

Leu Gly Trp Gln Val Glu Leu Cys Gly Tyr Val Glu Asp Thr Leu Pro
65                  70                  75                  80

Lys Ile Ile Ser Ser Asp Pro Asn Ile Thr Val His His Met Ser Asn
                85                  90                  95

Leu Lys Arg Lys Gly Gly Gly Thr Ser Val Ile Phe Met Val Lys Lys
            100                 105                 110

Val Leu Phe Gln Val Leu Ser Ile Phe Lys Leu Leu Trp Glu Leu Arg
        115                 120                 125

Gly Ser Asp Tyr Ile Leu Val Gln Asn Pro Pro Ser Ile Pro Ile Leu
    130                 135                 140

Pro Ile Ala Val Leu Tyr Lys Leu Thr Gly Cys Lys Leu Ile Ile Asp
145                 150                 155                 160

Trp His Asn Leu Ala Tyr Ser Ile Leu Gln Leu Lys Phe Lys Gly Asn
                165                 170                 175
```

```
Phe Tyr His Pro Leu Val Leu Ile Ser Tyr Met Val Glu Met Ile Phe
                180                 185                 190

Ser Lys Phe Ala Asp Tyr Asn Leu Thr Val Thr Glu Ala Met Arg Lys
            195                 200                 205

Tyr Leu Ile Gln Ser Phe His Leu Asn Pro Lys Arg Cys Ala Val Leu
        210                 215                 220

Tyr Asp Arg Pro Ala Ser Gln Phe Gln Pro Leu Ala Gly Asp Ile Ser
225                 230                 235                 240

Arg Gln Lys Ala Leu Thr Thr Lys Ala Phe Ile Lys Asn Tyr Ile Arg
                245                 250                 255

Asp Asp Phe Asp Thr Glu Lys Gly Asp Lys Ile Ile Val Thr Ser Thr
            260                 265                 270

Ser Phe Thr Pro Asp Glu Asp Ile Gly Ile Leu Leu Gly Ala Leu Lys
        275                 280                 285

Ile Tyr Glu Asn Ser Tyr Val Lys Phe Asp Ser Ser Leu Pro Lys Ile
        290                 295                 300

Leu Cys Phe Ile Thr Gly Lys Gly Pro Leu Lys Glu Lys Tyr Met Lys
305                 310                 315                 320

Gln Val Glu Glu Tyr Asp Trp Lys Arg Cys Gln Ile Glu Phe Val Trp
                325                 330                 335

Leu Ser Ala Glu Asp Tyr Pro Lys Leu Leu Gln Leu Cys Asp Tyr Gly
            340                 345                 350

Val Ser Leu His Thr Ser Ser Ser Gly Leu Asp Leu Pro Met Lys Ile
        355                 360                 365

Leu Asp Met Phe Gly Ser Gly Leu Pro Val Ile Ala Met Asn Tyr Pro
370                 375                 380

Val Leu Asp Glu Leu Val Gln His Asn Val Asn Gly Leu Lys Phe Val
385                 390                 395                 400

Asp Arg Arg Glu Leu His Glu Ser Leu Ile Phe Ala Met Lys Asp Ala
            405                 410                 415

Asp Leu Tyr Gln Lys Leu Lys Lys Asn Val Thr Gln Glu Ala Glu Asn
        420                 425                 430

Arg Trp Gln Ser Asn Trp Glu Arg Thr Met Arg Asp Leu Lys Leu Ile
            435                 440                 445

His

<210> SEQ ID NO 20
<211> LENGTH: 503
<212> TYPE: PRT
<213> ORGANISM: Saccharomyces cerevisiae

<400> SEQUENCE: 20

Met Ile Glu Lys Asp Lys Arg Thr Ile Ala Phe Ile His Pro Asp Leu
1               5                   10                  15

Gly Ile Gly Gly Ala Glu Arg Leu Val Val Asp Ala Ala Leu Gly Leu
            20                  25                  30

Gln Gln Gln Gly His Ser Val Ile Ile Tyr Thr Ser His Cys Asp Lys
        35                  40                  45

Ser His Cys Phe Glu Glu Val Lys Asn Gly Leu Lys Val Glu Val
    50                  55                  60

Tyr Gly Asp Phe Leu Pro Thr Asn Phe Leu Gly Arg Phe Phe Ile Val
65                  70                  75                  80

Phe Ala Thr Ile Arg Gln Leu Tyr Leu Val Ile Gln Leu Ile Leu Gln
                85                  90                  95
```

```
Lys Lys Val Asn Ala Tyr Gln Leu Ile Ile Ile Asp Gln Leu Ser Thr
            100                 105                 110

Cys Ile Pro Leu Leu His Ile Phe Ser Ser Ala Thr Leu Met Phe Tyr
            115                 120                 125

Cys His Phe Pro Asp Gln Leu Leu Ala Gln Arg Ala Gly Leu Leu Lys
            130                 135                 140

Lys Ile Tyr Arg Leu Pro Phe Asp Leu Ile Glu Gln Phe Ser Val Ser
145                 150                 155                 160

Ala Ala Asp Thr Val Val Asn Ser Asn Phe Thr Lys Asn Thr Phe
                    165                 170                 175

His Gln Thr Phe Lys Tyr Leu Ser Asn Asp Pro Asp Val Ile Tyr Pro
            180                 185                 190

Cys Val Asp Leu Ser Thr Ile Glu Ile Glu Asp Ile Asp Lys Lys Phe
            195                 200                 205

Phe Lys Thr Val Phe Asn Glu Gly Asp Arg Phe Tyr Leu Ser Ile Asn
    210                 215                 220

Arg Phe Glu Lys Lys Lys Asp Val Ala Leu Ala Ile Lys Ala Phe Ala
225                 230                 235                 240

Leu Ser Glu Asp Gln Ile Asn Asp Asn Val Lys Leu Val Ile Cys Gly
                    245                 250                 255

Gly Tyr Asp Glu Arg Val Ala Glu Asn Val Glu Tyr Leu Lys Glu Leu
            260                 265                 270

Gln Ser Leu Ala Asp Glu Tyr Glu Leu Ser His Thr Thr Ile Tyr Tyr
            275                 280                 285

Gln Glu Ile Lys Arg Val Ser Asp Leu Glu Ser Phe Lys Thr Asn Asn
            290                 295                 300

Ser Lys Ile Ile Phe Leu Thr Ser Ile Ser Ser Leu Lys Glu Leu
305                 310                 315                 320

Leu Leu Glu Arg Thr Glu Met Leu Leu Tyr Thr Pro Ala Tyr Glu His
                    325                 330                 335

Phe Gly Ile Val Pro Leu Glu Ala Met Lys Leu Gly Lys Pro Val Leu
            340                 345                 350

Ala Val Asn Asn Gly Gly Pro Leu Glu Thr Ile Lys Ser Tyr Val Ala
            355                 360                 365

Gly Glu Asn Glu Ser Ser Ala Thr Gly Trp Leu Lys Pro Ala Val Pro
            370                 375                 380

Ile Gln Trp Ala Thr Ala Ile Asp Glu Ser Arg Lys Ile Leu Gln Asn
385                 390                 395                 400

Gly Ser Val Asn Phe Glu Arg Asn Gly Pro Leu Arg Val Lys Lys Tyr
                    405                 410                 415

Phe Ser Arg Glu Ala Met Thr Gln Ser Phe Glu Glu Asn Val Glu Lys
            420                 425                 430

Val Ile Trp Lys Glu Lys Lys Tyr Tyr Pro Trp Glu Ile Phe Gly Ile
            435                 440                 445

Ser Phe Ser Asn Phe Ile Leu His Met Ala Phe Ile Lys Ile Leu Pro
            450                 455                 460

Asn Asn Pro Trp Pro Phe Leu Phe Met Ala Thr Phe Met Val Leu Tyr
465                 470                 475                 480

Phe Lys Asn Tyr Leu Trp Gly Ile Tyr Trp Ala Phe Val Phe Ala Leu
                    485                 490                 495

Ser Tyr Pro Tyr Glu Glu Ile
            500
```

<210> SEQ ID NO 21
<211> LENGTH: 202
<212> TYPE: PRT
<213> ORGANISM: Saccharomyces cerevisiae

<400> SEQUENCE: 21

Met Gly Ile Ile Glu Glu Lys Ala Leu Phe Val Thr Cys Gly Ala Thr
1               5                   10                  15

Val Pro Phe Pro Lys Leu Val Ser Cys Val Leu Ser Asp Glu Phe Cys
            20                  25                  30

Gln Glu Leu Ile Gln Tyr Gly Phe Val Arg Leu Ile Ile Gln Phe Gly
        35                  40                  45

Arg Asn Tyr Ser Ser Glu Phe Glu His Leu Val Gln Glu Arg Gly Gly
    50                  55                  60

Gln Arg Glu Ser Gln Lys Ile Pro Ile Asp Gln Phe Gly Cys Gly Asp
65                  70                  75                  80

Thr Ala Arg Gln Tyr Val Leu Met Asn Gly Lys Leu Lys Val Ile Gly
                85                  90                  95

Phe Asp Phe Ser Thr Lys Met Gln Ser Ile Ile Arg Asp Tyr Ser Asp
            100                 105                 110

Leu Val Ile Ser His Ala Gly Thr Gly Ser Ile Leu Asp Ser Leu Arg
        115                 120                 125

Leu Asn Lys Pro Leu Ile Val Cys Val Asn Asp Ser Leu Met Asp Asn
    130                 135                 140

His Gln Gln Gln Ile Ala Asp Lys Phe Val Glu Leu Gly Tyr Val Trp
145                 150                 155                 160

Ser Cys Ala Pro Thr Glu Thr Gly Leu Ile Ala Gly Leu Arg Ala Ser
                165                 170                 175

Gln Thr Glu Lys Leu Lys Pro Phe Pro Val Ser His Asn Pro Ser Phe
            180                 185                 190

Glu Arg Leu Leu Val Gly Thr Ile Tyr Ser
        195                 200

<210> SEQ ID NO 22
<211> LENGTH: 237
<212> TYPE: PRT
<213> ORGANISM: Saccharomyces cerevisiae

<400> SEQUENCE: 22

Met Lys Thr Ala Tyr Leu Ala Ser Leu Val Leu Ile Val Ser Thr Ala
1               5                   10                  15

Tyr Val Ile Arg Leu Ile Ala Ile Leu Pro Phe Phe His Thr Gln Ala
            20                  25                  30

Gly Thr Glu Lys Asp Thr Lys Asp Gly Val Asn Leu Leu Lys Ile Arg
        35                  40                  45

Lys Ser Ser Lys Lys Pro Leu Lys Ile Phe Val Phe Leu Gly Ser Gly
    50                  55                  60

Gly His Thr Gly Glu Met Ile Arg Leu Leu Glu Asn Tyr Gln Asp Leu
65                  70                  75                  80

Leu Leu Gly Lys Ser Ile Val Tyr Leu Gly Tyr Ser Asp Glu Ala Ser
                85                  90                  95

Arg Gln Arg Phe Ala His Phe Ile Lys Lys Phe Gly His Cys Lys Val
            100                 105                 110

Lys Tyr Tyr Glu Phe Met Lys Ala Arg Glu Val Lys Ala Thr Leu Leu
        115                 120                 125

```
Gln Ser Val Lys Thr Ile Ile Gly Thr Leu Val Gln Ser Phe Val His
        130                 135                 140

Val Val Arg Ile Arg Phe Ala Met Cys Gly Ser Pro His Leu Phe Leu
145                 150                 155                 160

Leu Asn Gly Pro Gly Thr Cys Cys Ile Ile Ser Phe Trp Leu Lys Ile
                165                 170                 175

Met Glu Leu Leu Leu Pro Leu Leu Gly Ser Ser His Ile Val Tyr Val
                180                 185                 190

Glu Ser Leu Ala Arg Ile Asn Thr Pro Ser Leu Thr Gly Lys Ile Leu
                195                 200                 205

Tyr Trp Val Val Asp Glu Phe Ile Val Gln Trp Gln Glu Leu Arg Asp
210                 215                 220

Asn Tyr Leu Pro Arg Ser Lys Trp Phe Gly Ile Leu Val
225                 230                 235

<210> SEQ ID NO 23
<211> LENGTH: 574
<212> TYPE: PRT
<213> ORGANISM: Saccharomyces cerevisiae

<400> SEQUENCE: 23

Met Ala Lys Lys Asn Ser Gln Leu Pro Ser Thr Ser Glu Gln Ile Leu
1               5                   10                  15

Glu Arg Ser Thr Thr Gly Ala Thr Phe Leu Met Met Gly Gln Leu Phe
                20                  25                  30

Thr Lys Leu Val Thr Phe Ile Leu Asn Asn Leu Leu Ile Arg Phe Leu
            35                  40                  45

Ser Pro Arg Ile Phe Gly Ile Thr Ala Phe Leu Glu Phe Ile Gln Gly
50                  55                  60

Thr Val Leu Phe Phe Ser Arg Asp Ala Ile Arg Leu Ser Thr Leu Arg
65                  70                  75                  80

Ile Ser Asp Ser Gly Asn Gly Ile Ile Asp Asp Asp Glu Glu Glu
                85                  90                  95

Tyr Gln Glu Thr His Tyr Lys Ser Lys Val Leu Gln Thr Ala Val Asn
                100                 105                 110

Phe Ala Tyr Ile Pro Phe Trp Ile Gly Phe Pro Leu Ser Ile Gly Leu
            115                 120                 125

Ile Ala Trp Gln Tyr Arg Asn Ile Asn Ala Tyr Phe Ile Thr Leu Pro
130                 135                 140

Phe Phe Arg Trp Ser Ile Phe Leu Ile Trp Leu Ser Ile Ile Val Glu
145                 150                 155                 160

Leu Leu Ser Glu Pro Phe Phe Ile Val Asn Gln Phe Met Leu Asn Tyr
                165                 170                 175

Ala Ala Arg Ser Arg Phe Glu Ser Ile Ala Val Thr Thr Gly Cys Ile
                180                 185                 190

Val Asn Phe Ile Val Val Tyr Ala Val Gln Gln Ser Arg Tyr Pro Met
            195                 200                 205

Gly Val Val Thr Ser Asp Ile Asp Lys Glu Gly Ile Ala Ile Leu Ala
210                 215                 220

Phe Ala Leu Gly Lys Leu Ala His Ser Ile Thr Leu Leu Ala Cys Tyr
225                 230                 235                 240

Tyr Trp Asp Tyr Leu Lys Asn Phe Lys Pro Lys Lys Leu Phe Ser Thr
                245                 250                 255

Arg Leu Thr Lys Ile Lys Thr Arg Glu Asn Asn Glu Leu Lys Lys Gly
            260                 265                 270
```

```
Tyr Pro Lys Ser Thr Ser Tyr Phe Phe Gln Asn Asp Ile Leu Gln His
            275                 280                 285

Phe Lys Lys Val Tyr Phe Gln Leu Cys Phe Lys His Leu Leu Thr Glu
        290                 295                 300

Gly Asp Lys Leu Ile Ile Asn Ser Leu Cys Thr Val Glu Glu Gln Gly
305                 310                 315                 320

Ile Tyr Ala Leu Leu Ser Asn Tyr Gly Ser Leu Leu Thr Arg Leu Leu
                325                 330                 335

Phe Ala Pro Ile Glu Glu Ser Leu Arg Leu Phe Leu Ala Arg Leu Leu
            340                 345                 350

Ser Ser His Asn Pro Lys Asn Leu Lys Leu Ser Ile Glu Val Leu Val
                355                 360                 365

Asn Leu Thr Arg Phe Tyr Ile Tyr Leu Ser Leu Met Ile Ile Val Phe
        370                 375                 380

Gly Pro Ala Asn Ser Ser Phe Leu Leu Gln Phe Leu Ile Gly Ser Lys
385                 390                 395                 400

Trp Ser Thr Thr Ser Val Leu Asp Thr Ile Arg Val Tyr Cys Phe Tyr
                405                 410                 415

Ile Pro Phe Leu Ser Leu Asn Gly Ile Phe Glu Ala Phe Phe Gln Ser
            420                 425                 430

Val Ala Thr Gly Asp Gln Ile Leu Lys His Ser Tyr Phe Met Met Ala
        435                 440                 445

Phe Ser Gly Ile Phe Leu Leu Asn Ser Trp Leu Leu Ile Glu Lys Leu
    450                 455                 460

Lys Leu Ser Ile Glu Gly Leu Ile Leu Ser Asn Ile Ile Asn Met Val
465                 470                 475                 480

Leu Arg Ile Leu Tyr Cys Gly Val Phe Leu Asn Lys Phe His Arg Glu
                485                 490                 495

Leu Phe Thr Asp Ser Ser Phe Phe Asn Phe Lys Asp Phe Lys Thr
            500                 505                 510

Val Ile Ile Ala Gly Ser Thr Ile Cys Leu Leu Asp Trp Trp Phe Ile
        515                 520                 525

Gly Tyr Val Lys Asn Leu Gln Gln Phe Val Val Asn Val Leu Phe Ala
    530                 535                 540

Met Gly Leu Leu Ala Leu Ile Leu Val Lys Glu Arg Gln Thr Ile Gln
545                 550                 555                 560

Ser Phe Ile Asn Lys Arg Ala Val Ser Asn Ser Lys Asp Val
                565                 570

<210> SEQ ID NO 24
<211> LENGTH: 718
<212> TYPE: PRT
<213> ORGANISM: Saccharomyces cerevisiae

<400> SEQUENCE: 24

Met Gly Ser Asp Arg Ser Cys Val Leu Ser Val Phe Gln Thr Ile Leu
1               5                   10                  15

Lys Leu Val Ile Phe Val Ala Ile Phe Gly Ala Ala Ile Ser Ser Arg
            20                  25                  30

Leu Phe Ala Val Ile Lys Phe Glu Ser Ile Ile His Glu Phe Asp Pro
        35                  40                  45

Trp Phe Asn Tyr Arg Ala Thr Lys Tyr Leu Val Asn Asn Ser Phe Tyr
    50                  55                  60

Lys Phe Leu Asn Trp Phe Asp Asp Arg Thr Trp Tyr Pro Leu Gly Arg
```

```
            65                  70                  75                  80
Val Thr Gly Gly Thr Leu Tyr Pro Gly Leu Met Thr Thr Ser Ala Phe
                    85                  90                  95

Ile Trp His Ala Leu Arg Asn Trp Leu Gly Leu Pro Ile Asp Ile Arg
                100                 105                 110

Asn Val Cys Val Leu Phe Ala Pro Leu Phe Ser Gly Val Thr Ala Trp
                115                 120                 125

Ala Thr Tyr Glu Phe Thr Lys Glu Ile Lys Asp Ala Ser Ala Gly Leu
                130                 135                 140

Leu Ala Ala Gly Phe Ile Ala Ile Val Pro Gly Tyr Ile Ser Arg Ser
145                 150                 155                 160

Val Ala Gly Ser Tyr Asp Asn Glu Ala Ile Ala Ile Thr Leu Leu Met
                165                 170                 175

Val Thr Phe Met Phe Trp Ile Lys Ala Gln Lys Thr Gly Ser Ile Met
                180                 185                 190

His Ala Thr Cys Ala Ala Leu Phe Tyr Phe Met Val Ser Ala Trp
                195                 200                 205

Gly Gly Tyr Val Phe Ile Thr Asn Leu Ile Pro Leu His Val Phe Leu
                210                 215                 220

Leu Ile Leu Met Gly Arg Tyr Ser Ser Lys Leu Tyr Ser Ala Tyr Thr
225                 230                 235                 240

Thr Trp Tyr Ala Ile Gly Thr Val Ala Ser Met Gln Ile Pro Phe Val
                245                 250                 255

Gly Phe Leu Pro Ile Arg Ser Asn Asp His Met Ala Ala Leu Gly Val
                260                 265                 270

Phe Gly Leu Ile Gln Ile Val Ala Phe Gly Asp Phe Val Lys Gly Gln
                275                 280                 285

Ile Ser Thr Ala Lys Phe Lys Val Ile Met Met Val Ser Leu Phe Leu
                290                 295                 300

Ile Leu Val Leu Gly Val Val Gly Leu Ser Ala Leu Thr Tyr Met Gly
305                 310                 315                 320

Leu Ile Ala Pro Trp Thr Gly Arg Phe Tyr Ser Leu Trp Asp Thr Asn
                325                 330                 335

Tyr Ala Lys Ile His Ile Pro Ile Ile Ala Ser Val Ser Glu His Gln
                340                 345                 350

Pro Val Ser Trp Pro Ala Phe Phe Asp Thr His Phe Leu Ile Trp
                355                 360                 365

Leu Phe Pro Ala Gly Val Phe Leu Leu Phe Leu Asp Leu Lys Asp Glu
                370                 375                 380

His Val Phe Val Ile Ala Tyr Ser Val Leu Cys Ser Tyr Phe Ala Gly
385                 390                 395                 400

Val Met Val Arg Leu Met Leu Thr Leu Thr Pro Val Ile Cys Val Ser
                405                 410                 415

Ala Ala Val Ala Leu Ser Lys Ile Phe Asp Ile Tyr Leu Asp Phe Lys
                420                 425                 430

Thr Ser Asp Arg Lys Tyr Ala Ile Lys Pro Ala Ala Leu Leu Ala Lys
                435                 440                 445

Leu Ile Val Ser Gly Ser Phe Ile Phe Tyr Leu Tyr Leu Phe Val Phe
                450                 455                 460

His Ser Thr Trp Val Thr Arg Thr Ala Tyr Ser Ser Pro Ser Val Val
465                 470                 475                 480

Leu Pro Ser Gln Thr Pro Asp Gly Lys Leu Ala Leu Ile Asp Asp Phe
                485                 490                 495
```

-continued

```
Arg Glu Ala Tyr Tyr Trp Leu Arg Met Asn Ser Asp Glu Asp Ser Lys
            500                 505                 510
Val Ala Ala Trp Trp Asp Tyr Gly Tyr Gln Ile Gly Gly Met Ala Asp
            515                 520                 525
Arg Thr Thr Leu Val Asp Asn Asn Thr Trp Asn Asn Thr His Ile Ala
            530                 535                 540
Ile Val Gly Lys Ala Met Ala Ser Pro Glu Glu Lys Ser Tyr Glu Ile
545                 550                 555                 560
Leu Lys Glu His Asp Val Asp Tyr Val Leu Val Ile Phe Gly Gly Leu
                565                 570                 575
Ile Gly Phe Gly Gly Asp Asp Ile Asn Lys Phe Leu Trp Met Ile Arg
            580                 585                 590
Ile Ser Glu Gly Ile Trp Pro Glu Glu Ile Lys Glu Arg Asp Phe Tyr
            595                 600                 605
Thr Ala Glu Gly Glu Tyr Arg Val Asp Ala Arg Ala Ser Glu Thr Met
            610                 615                 620
Arg Asn Ser Leu Leu Tyr Lys Met Ser Tyr Lys Asp Phe Pro Gln Leu
625                 630                 635                 640
Phe Asn Gly Gly Gln Ala Thr Asp Arg Val Arg Gln Gln Met Ile Thr
                645                 650                 655
Pro Leu Asp Val Pro Pro Leu Asp Tyr Phe Asp Glu Val Phe Thr Ser
                660                 665                 670
Glu Asn Trp Met Val Arg Ile Tyr Gln Leu Lys Lys Asp Asp Ala Gln
            675                 680                 685
Gly Arg Thr Leu Arg Asp Val Gly Glu Leu Thr Arg Ser Ser Thr Lys
            690                 695                 700
Thr Arg Arg Ser Ile Lys Arg Pro Glu Leu Gly Leu Arg Val
705                 710                 715
```